US007264941B1

(12) United States Patent
Birkelund et al.

(10) Patent No.: US 7,264,941 B1
(45) Date of Patent: Sep. 4, 2007

(54) **SURFACE EXPOSED PROTEINS FROM *CHLAMYDIA PNEUMONIAE***

(76) Inventors: Svend Birkelund, Søtoften 26, DK-8250 Egå (DK); Gunna Christiansen, Søtoften 26, DK-8250 Egå (DK); Anna-Sofie Hebsgaard Pedersen, Vestergade 26C, 2.th., DK-8600 Silkeborg (DK); Per Mygind, Cort Adelers Gade 17, 1. tv., DK-8200 Århus N (DK); Katrine Knudsen, Lundingsgade 33, lejlighed 407, DK-8000 Århus C (DK)

( * ) Notice: Subject to any disclaimer, the term of this patent is extended or adjusted under 35 U.S.C. 154(b) by 0 days.

(21) Appl. No.: 09/446,677

(22) PCT Filed: Jun. 19, 1998

(86) PCT No.: PCT/DK98/00266

§ 371 (c)(1),
(2), (4) Date: Mar. 24, 2000

(87) PCT Pub. No.: WO98/58953

PCT Pub. Date: Dec. 30, 1998

(30) Foreign Application Priority Data

Jun. 23, 1997 (DK) .................................... 0744/97

(51) Int. Cl.
*G01N 33/554* (2006.01)
(52) U.S. Cl. .................... 435/7.32; 424/185.1; 530/350
(58) Field of Classification Search ............. 424/190.1, 424/263.1; 435/6, 19.1
See application file for complete search history.

(56) References Cited

U.S. PATENT DOCUMENTS 6,248,329 B1 * 6/2001 Chandrashekar et al. ........................ 424/191.1

FOREIGN PATENT DOCUMENTS

EP          0699 688 A2 *  3/1995
EP          0784059         7/1997

OTHER PUBLICATIONS

Melgosa et al. "Outer membrane complex proteins of *Chlamydia pneumoniae*", FEMSMicrobiology Letters, vol. 112, No. 2, pp. 199-204, 1993.*
Van De Loo et al., "An oleate 12-hydroxy from Ricinus communis . . .", Proc. Natl. Acad. Sci. vol. 92, pp. 6743-6747, 1995.*
Broun, P. et al, "Catalytic Plasticity of Fatty Acid . . . " Science, vol. 282, No. 13, pp. 1315-1317, 1998.*
Rudinger al. "Peptide Hormones", Published by University Park Press, Blaltimore. Jun. 1976.*
Salgaller et al. Cancer Immuno. Immunother. 39: 105-116, 1994.*
Rudikoff et al. "Single amino acid substitution altering antigen-binding specificity", Proc. Natl. Acad. Sci. vol. 79, pp. 1979-1983, Mar. 1982.*
Jameson et al. "The antigenic index : a novel algorithm for predicting antigenic determinants" CABIOS, vol. 4 No. 1, pp. 181-186 1988.*
Herbert et al eds, The Dictionary of Immunology, Academic Press Inc., Fourth Edition, 1995, pp. 58-59 and 90.*
The Dictionary of Immunology, Herbert et al eds, Academic Press, 1995.*
Feng et al (Infection and Immunity, 64(1):363-365, 1996).*
Ellis, R.W. (Chapter 29 of "VACCINES" [Plotkin, S.A. et al. (eds) published by W. B. Saunders company (Philadelphia) in 1988, especially p. 571, 2nd full paragarph].*
Caldwell, H.D., et al., "Purification and Partial Characterization of the Major Outer Membrane Protein of *Chlamydia trachomatis*," *Infect. and Immun.* 31:1161-1176 (1981).
Campbell, L.A., et al., "Detection of *Chlamydia pneumoniae* by Polymerase Chain Reaction," *Journal of Clinical Microbiology* 30(2):434-439 (1992).
Christiansen, G., et al., "A Review of *Chlamydia pneumoniae*" *European Microbiology* 1:24-29 (1992).
Christiansen, G., et al., "Analysis of the *Chlamydia pneumoniae* Surface" Proceedings of the eight International symposium on Human Infections, Eds., Orfila et al, pp. 173-176, (1994).
Grayston, J.T., et al., "*Chlamydia pneumoniae* sp. nov. for *Chlamydia* sp. Strain TWAR," *International Journal of Systematic Bacteriology* 39(1):88-90 (1989).
Grayston, J.T., et al., "A New *Chlamydia psittaci* Strain, TWAR, Isolated in Acute Respiratory Tract Infections," *The New England Journal of Medicine* 315(3):161-168 (1986).
Kuo, C.C., et al., "*Chlamydia pneumoniae* (TWAR)," *Clinical Microbiology Reviews* 8(4):451-461 (1995).
Longbottom, D., et al., "Identification of a Multigene Family Coding for the 90 kDa Proteins of the Ovine Abortion Subtype of *Chlamydia psittaci*," *FEMS Letters* 142:277-281 (1996).
Melgosa, M.P., et al., "Outer Membrane Complex Proteins of *Chlamydia pneumoniae*," *FEMS Letters* 112:199-204 (1993).
Campbell, L.A., et al., "Serological Response to *Chlamydia pneumoniae* Infection," *Journal of Clinical Microbiology* 28(6):1261-1264 (1990).
Halme, S., et al., "Characterization of *Chlamydia pneumoniae* Antigens Using Human T Cell Clones," *Scandinavian Journal of Immunology* 45:378-384 (1997).
Miyashita, N., et al., "Establishment of a Particle-Counting Method for Purified Elementary Bodies of *Chlamydiae* and Evaluation of Sensitivities of the IDEIA Chlamydia Kit and DNA Probe by Using the Purified Elementary Bodies," *Journal of Clinical Microbiology* 30(11):2911-2916 (1992).

(Continued)

*Primary Examiner*—Patricia A. Duffy
(74) *Attorney, Agent, or Firm*—Iver P. Cooper

(57) ABSTRACT

The invention relates to the identification of members of a gene family from the human respiratory pathogen *Chlamydia pneumoniae*, encoding surface exposed membrane proteins of a size of approximately 89-101 kDa, preferably about 89.6-100.3 kDa and about 56.1 kDa. The invention relates to the novel DNA sequences, the deduced amino acid sequences of the corresponding proteins and the use of the DNA sequences and the proteins in diagnosis of infections caused by *C. pneumoniae*, in pathology, in epidemiology, and as vaccine components.

4 Claims, 21 Drawing Sheets

OTHER PUBLICATIONS

Figures 1A, 1B:
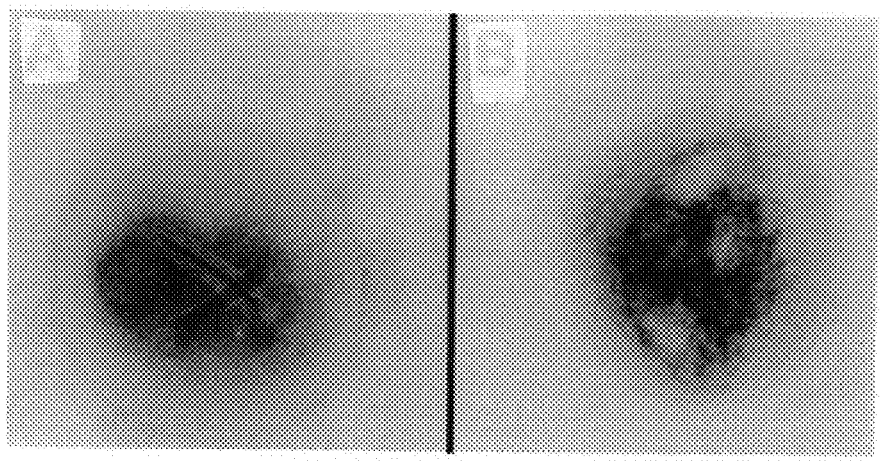

Wang, S.P., et al., "Immunologic Relationship Between Genital TRIC, Lymphogranuloma Venereum, and Related Organisms in a New Microtiter Indirect Immunofluroescence Test," *American Journal of Opthalmology* 70:367-374 (1970).

Freund, E.A., et al., "Identification of Mycoplasma," p. 377-434 in Norris, I., et al., "Methods in Microbiology" 13 A.P. Inc. London (1979).

Campbell, et al., *Structural and Antigenic Analysis of Chlamydia pneumoniae*, Infection and Immunity, vol. 58, No. 1, pp. 93-97, Jan. 1990.

Christiansen, et al., *Molecular Biology of the Chlamydia pneumoniae Surface XP-002088986*, Scand. J. Infectious Diseases, supplement 104, pp. 5-10, 1997.

Kanamoto, et al., *Antigent Characterization of Chlamydia pneumoniae Isolated in Hiroshima, Japan*, Microbiology and Immunology, vol. 37, No. 6, pp. 495-498, 1993.

* cited by examiner

SURFACE EXPOSED PROTEINS FROM *CHLAMYDIA PNEUMONIAE*

This is a U.S.C. 371 of Application No. PCT/DK98/00266, filed Jun. 19, 1998 and claims priority to Danish application No. 0744/97, filed on Jun. 23, 1997.

The present invention relates to the identification of members of a gene family from the human respiratory pathogen *Chlamydia pneumoniae*, encoding surface exposed membrane proteins of a size of approximately 89-101 kDa and of 56-57 kDa, preferably about 89.6-100.3 kDa and about 56.1 kDa. The invention relates to the novel DNA sequences, the deduced amino acid sequences of the corresponding proteins and the use of the DNA sequences and the proteins in diagnosis of infections caused by *C. pneumoniae*, in pathology, in epidemiology, and as vaccine components.

GENERAL BACKGROUND

*C. pneumoniae* is an obligate intracellular bacteria (Christiansen and Birkelund (1992); Grayston et al. (1986)). It has a cell wall structure as Gram negative bacteria with an outer membrane, a periplasmic space, and a cytoplasmic membrane. It is possible to purify the outer membrane from Gram negative bacteria with the detergent sarkosyl. This fraction is named the 'outer membrane complex (OMC)' (Caldwell et al. (1981)). The COMC (*Chlamydia* outer membrane complex) of *C. pneumoniae* contains four groups of proteins: A high molecular weight protein 98 kDa as determined by SDS-PAGE, a double band of the cysteine rich outer membrane protein 2 (Omp2) protein of 62/60 kDa, the major outer membrane protein (MOMP) of 38 kDa, and the low-molecular weight lipo-protein Omp3 of 12 kDa. The Omp2/Omp3 and MOMP proteins are present in COMC from all *Chlamydia* species, and these genes have been cloned from both *C. trachomatis*, *C. psittaci* and *C. pneumoniae*. However, the gene encoding 98 kDa protein from *C. pneumoniae* COMC have not been characterized or cloned.

The current state of *C. pneumoniae* serology and detection

*C. pneumoniae* is an obligate intra-cellular bacteria belonging to the genus *Chlamydia* which can be divided into four species: *C. trachomatis*, *C. pneumoniae*, *C. psittaci* and *C.pecorum*. Common for the four species is their obligate intra cellular growth, and that they have a biphasic life cycle, with an extracellular infectious particle (the elementary body, EB), and an intercellular replicating form (the reticulate body, RB). In addition the *Chlamydia* species are characterized by a common lipopolysaccharide (LPS) epitope that is highly immunogenic in human infection. *C. trachomatis* is causing the human ocular infection (trachoma) and genital infections. *C. psittaci* is a variable group of animal pathogens where the avian strains can occasionally infect humans and give rise to a severe pneumonia (ornithosis). The first *C. pneumoniae* isolate was obtained from an eye infection, but it was classified as a non-typable *Chlamydia*. Under an epidemic outbreak of pneumonia in Finland it was realized that the patients had a positive reaction in the *Chlamydia* genus specific test, (the lygranum test), and the patients showed a titre increase to the untyped *Chlamydia* isolates. Similar isolates were obtained in an outbreak of upper respiratory tract infections in Seattle, and the *Chlamydia* isolates were classified as a new species, *Chlamydia pneumoniae* (Grayston et al. (1989)). In addition, *C. pneumoniae* is suggested to be involved in the development of atherosclerotic lesions and for initiating bronchial asthma (Kuo et al. (1995)). These two conditions are thought to be caused by either chronic infections, by a hypersensitivity reaction, or both.

Diagnosis of *Chlamydia pneumoniae* infections

Diagnosis of acute respiratory tract infection with *C. pneumoniae* is difficult. Cultivation of *C. pneumoniae* from patient samples is insensitive, even when proper tissue culture cells are selected for the isolation. A *C. pneumoniae* specific polymerase chain reaction (PCR) has been developed by Campbell et al.(1992).

Even though *Chlamydia pneumoniae* has in several studies been detected by this PCR it is debated whether this method is suitable for detection under all clinical situations. The reason for this is, that the cells carrying *Chlamydia pneumoniae* in acute respiratory infections have not been determined, and that a chronic carrier state is expected but it is unknown in which organs and cells they are present. Furthermore, the PCR test is difficult to perform due to the low yield of these bacteria and due to the presence of inhibitory substances in the patient samples. Therefore, it will be of great value to develop sensitive and specific sero-diagnostics for detecting both acute and chronic infections. Sero-diagnosis of *Chlamydia* infections is currently based on either genus specific tests as the Lygranum test and ELISA, measuring the antibodies to LPS, or the more species specific tests where antibodies to purified EBs are measured by microimmuno fluorescence (Micro-IF)(Wang et al. (1970)). However, the micro-IF method is read by microscopy, and in order to ensure correct readings the result must be compared to the results with *C. trachomatis* used as antigen due to the cross-reacting antibodies to the common LPS epitope. Thus, there exists in the art an urgent need for development of reliable methods for species specific diagnosis of *Chlamydia pneumoniae*, as has been expressed in Kuo et al. (1995); ". . . a rapid reliable laboratory test of infection for the clinical laboratory is a major need in the field". Furthermore, the possible involvement of *C. pneumoniae* in atherosclerosis and bronchial asthma clearly warrants the development of an effective vaccine.

DETAILED DISCLOSURE OF THE INVENTION

The present invention aims at providing means for efficient diagnosis of infections with *Chlamydia pneumoniae* as well as the development of effective vaccines against infection with this microorganism. The invention thus relates to species specific diagnostic tests for infection in a mammal, such as a human, with *Chlamydia pneumoniae*, said tests being based on the detection of antibodies against surface exposed membrane proteins of a size of approximately 89-101 kDa and of 56-57 kDa, preferably of about 89.6-100.3 kDa and about 56.1 kDa (the range in size of the deduced amino acid sequences was from 100.3 to 89.6 except for Omp13 SEQ ID NO:20 with the size of 56.1 kDa), or the detection of nucleic acid fragments encoding such proteins or variants or subsequences thereof. The invention further relates to the amino acid sequences of proteins according to the invention, to variants and subsequences thereof, and to nucleic acid fragments encoding these proteins or variants or subsequences thereof. The present invention further relates to antibodies against proteins according to the invention. The invention also relates to the use of isolated nucleic acid fragments and isolated proteins according to the invention in diagnosis of *Chlamydia pneumoniae* and vaccines against *Chlamydia pneumoniae*.

Prior to the disclosure of the present invention only a very limited number of genes from *C. pneumoniae* had been sequenced. These were primarily the genes encoding known *C. trachomatis* homologues: MOMP, Omp2, Omp3, Kdo-transferase, the heat shock protein genes GroEl/Es and DnaK, a ribonuclease P homologue and a gene encoding a 76 kDa protein of unknown function. The reason why so few genes have been cloned to date is the very low yield of *C. pneumoniae* which can be obtained after purification from the host cells. After such purification the DNA must be purified from the EBs, and at this step the *C. pneumoniae* DNA can easily be contaminated with host cell DNA. In addition to these inherent difficulties, it is exceedingly difficult to cultivate *C. pneumoniae* and use DNA technology to produce expression libraries with very low amounts (few μg of DNA. It has been known since 1993 (Melgosa et al., 1993, that a 98 kDa protein is present in OMC from *C. pneumoniae*. Even though the protein bands of 98 kDa was mentioned to be part of the OMC of *C. pneumoniae* by Melgosa, the gene sequences and thus the deduced amino acid sequences have not been determined. Only bands originating from *Chlamydia pneumoniae* proteins in general separated by SDS-PAGE are describe therein.

However, the gene encoding this protein has not been determined before the present invention. Only a very weak or no reaction with patient sera can be observed to the 98 kDa protein (Campbell et al. 1990) and prior to the work of the present inventors it has not been recognized that the 89-101 kDa proteins are surface exposed or that they in fact is immunogenic (see below). In this report it is described that a number of human serum samples reacts with a *C. pneumoniae* protein that in SDS-PAGE migrate as 98 kDa. The protein was not further characterized and it is therefore not in conflict with the present application.

Campbell et al. (1990) described that sera from four patients from which *Chlamydia pneumonia* was isolated reacted with bands of 98 kDa in immunoblotting using whole-cell lysates. They also showed that no proteins with similar molecular weights were recognised by serum samples in either *Chlamydia trachomatis* or *Chlamydia psittaci* and they therefore suggest that the protein present in the 98 kDa band could be used as a potential diagnostic tool for the recognition of *Chlamydia pneumoniae* infection. The protein content within the 98 kDa region was not further charactertised and its localisation within the *Chlamydia* was not shown.

Halme et al. (1997) described the presence of human T-cell epitopes in *C. pneumoniae* proteins of 92-98 kDa. The proteins were eluted from SDS-PAGE of total *chlamydia* proteins but the identity of the proteins were not determined.

Use of antibodies to screen expression libraries is a well known method to clone fragments of genes encoding anticenic parts of proteins. However, since patient sera do not show a significant reaction with the 98 kDa protein it has not been possible to use patient serum to clone the proteins.

It was known that monoclonal antibodies generated by the inventors reacted with conformational epitopes on the surface of *C. pneumoniae* and that they also reacted with *C. pneumoniae* OMC by immuno-electron microscopy (Christiansen et al. 1994). Furthermore, the 98 kDa protein is the only unknown protein from the *C. pneumoniae* OMC (Melgosa et al. 1993). The present inventors chose to take an unconventional step in order to clone the gene encoding the hitherto unknown 98 kDa protein: *C. pneumoniae* OMC was purified and the highly immunogenic conformational epitopes were destroyed by SDS-treatment of the antigen before immunization. Thereby an antibody (PAB 150) to less immunogenic linear epitopes was obtained. This provided the possibility to obtain an antiserum which could detect the protein, and it was shown that a gene family encoding the 89-101 kDa and 56 proteins according to the invention could be detected in colony blotting of recombinant *E. coli*.

Mice infected with *C. pneumoniae* generate antibodies to the proteins identified by the inventors and named Omp4-15 (SEQ ID NOs:2, 4, 6, 8, 10, 12, 14, 16, 18, 20, 22, 24), but do not recognize the SDS treated heat denatured antigens normally used for SDS-PAGE and immunoblotting. However, a strong reaction was seen if the antigen was not heat denatured. It is therefore highly likely that if a similar reaction is seen in connection with human infections the antigens of the present invention will be of invaluable use in sero-diagnostic tests and may very likely be used as a vaccine for the prevention of infections.

By generating antibodies against COMC from *C. pneumoniae* a polyclonal antibody (PAB 150) was obtained which reacted with all the proteins. This antibody was used to identify the genes encoding the 89.6-101.3 kDa and 56.1 kDa proteins in an expression library of *C. pneumoniae* DNA. A problem in connection with the present invention was that a family comprising a number of similar genes were found in *C. pneumoniae*. Therefore, a large number of different clones were required to identify clusters of fragments. Only because the rabbit antibody generated by the use of SDS-denatured antigens contained antibodies to a high number of different epitopes positioned on different members of the protein family did the inventors succeed in cloning and sequencing four of the genes. One gene was fully sequenced, a second was sequenced except for the distal part and shorter fragments of two additional genes were obtained by this procedure. To obtain the DNA sequence of the additional genes and to search for more members of the gene family long range PCR with primers derived from the sequenced genes, and primers from the genes already published in the database were used. This approach gave rise to the detection of additional eight genes belonging to this family. The genes were situated in two gene clusters: Omp12,11,10,5,4,13 and 14 (SEQ ID NOs:17, 15, 13, 3, 1, 19, 21) in one cluster and Omp6,7,8,9 and 15 (SEQ ID Nos:5, 7, 9, 11, 23) in the second. Full sequence was obtained from Omp4,5,6,7,8,9,10,11 and 13 (SEQ ID NOs:1, 3, 5, 7, 9, 11, 13, 15, 19), and partial sequence of Omp12,14 (SEQ ID NOS:17, 21). Omp13 (SEQ ID NO:19) was a truncated gene of 1545 nucleotides. The rest of the full length genes were from 2526 (Omp7) (SEO ID NO:7) to 2838 (Omp15) (SEQ ID NO:23) nucleotides. The deduced amino acid sequences revealed putative polypeptides of 89.6 to 100.3 kDa, except for Omp13 (SEQ ID NO:20) of 56.1 kDa. Alignment of the deduced amino acid sequences showed a maximum identity of 49% (Omp5/Omp9) (SEQ ID NO:4)/(SEQ ID NO:12) when all the sequences were compared. Except for Omp13 (SEQ ID NO:20), the lowest homology was to Omp7 (SEQ ID NO:8) with no more than 34% identity to any of the other amino acid sequences. The scores for Omp13 (SEQ ID NO:20) was from 29-32% to all the other sequences.

In the present context SEQ ID Nos. 1 and 2 correspond to Omp4, SEQ ID Nos 3 and 4 correspond to Omp5, SEQ ID Nos 5 and 6 correspond to Omp6, SEQ ID Nos 7 and 8 correspond to Omp7, SEQ ID Nos 9 and 10 correspond to Omp8, SEQ ID Nos 11 and 12 correspond to Omp9, SEQ ID Nos 13 and 14 corresponds to Omp10, SEQ ID Nos 15 and 16 corresponds to Omp11, SEQ ID Nos 17 and 18 corresponds to Omp12, SEQ ID Nos 19 and 20 corresponds to Omp13, SEQ ID Nos 21 and 22 corresponds to Omp14, and SEQ ID Nos 23 and 24 corresponds to Omp15.

The estimated size of the Omp proteins of the present invention are listed in the following. Omp 4 (SEQ ID NO:2) has a size of 98.9 kDa, Omp5 (SEQ ID NO:4) has an estimated size of 97.2 kDa, Omp6 (SEQ ID NO:6) has an estimated size of 100.3 kDa, Omp7 (SEQ ID NO:8) has an estimated size of 89.7 kDa, Omp8 (SEQ ID NO:10) has an estimated size of 90.0 kDa, Omp9 (SEQ ID NO:12) has an estimated size of 96.7 kDa, Omp10 (SEQ ID NO:14) has an estimated size of 98.4 kDa, Omp11 (SEQ ID NO:16) has an estimated size of 97.6 kDa, Omp13 (SEQ ID NO:20) has an estimated size of 56.1 kDa, Omp 12 and 14 (SEQ ID NO:18) and (SEQ ID NO:22) being partial.

Furthermore, SEQ ID No 25 is a subsequence of SEQ ID No 3, SEQ ID No 26 is a subsequence of SEQ ID No 4, SEQ ID No 27 is a subsequence of SEQ ID No 5, SEQ ID No 28 is a subsequence of SEQ ID No 6, SEQ ID No 29 is a subsequence of SEQ ID No 7, and SEQ ID No 30 is a subsequence of SEQ ID No 8.

Part of the omp proteins were expressed as fusion proteins, and mice polyclonal monospecific antibodies against the proteins were produced. The antibodies reacted with the surface of *C. pneumoniae* in both immunofluorescence and immunoelectron microscopy. This shows for the first time that the 89-101 kDa and 56-57 kDa protein family in *C. pneumoniae* comprises surface exposed outer membrane proteins. This important finding leads to the realization that members of the 89-101 kDa and 56-57 kDa *C. pneumoniae* protein family are good candidates for the development of a sero diagnostic test for *C. pneumoniae*, as well as the development of a vaccine against infections with *C. pneumoniae* based on using these proteins. Furthermore, the proteins may be used as epidemiological markers, and polyclonal monospecific sera against the proteins can be used to detect *C. pneumoniae* in human tissue or detect *C. pneumoniae* isolates in tissue culture. Also, the genes encoding the 89-101 kDa and 56-57 kDa such as the 89.6-100.3 kDa and 56.1 protein family may be used for the development of a species specific diagnostic test based on nucleic acid detection/amplification.

The full length Omp4 (SEQ ID NO:1) was cloned into an expression vector system that allowed expression of the Omp4 polypeptide (SEQ ID NO:2). This polypeptide was used as antigen for immunization of a rabbit. Since the protein was purified under denaturing condition the antibody did not react with the native surface of *C. pneumoniae*, but it reacted with a 98 kDa protein in immunoblotting where purified *C. pneumoniae* EB was used as antigen. Furthermore, the antibody reacted in paraffin embedded sections of lung tissue from experimentally infected mice.

A broad aspect of the present invention relates to a species specific diagnostic test for infection of a mammal, such as a human, with *Chlamydia pneumoniae*, said test comprising detecting in a patient or preferable in a patient sample the presence of antibodies against proteins from the outer membrane of *Chlamydia pneumoniae*, said proteins being of a molecular weight of 89-101 kDa or 56-57 kDa, or detecting the presence of nucleic acid fragments encoding said outer membrane proteins or fragments thereof.

In the context of the present application, the term "patient sample" should be taken to mean an amount of serum from a patient, such as a human patient, or an amount of plasma from said patient, or an amount of mucosa from said patient, or an amount of tissue from said patient, or an amount of expectorate, forced sputum or a bronchial aspirate, an amount of urine from said patient, or an amount of cerebrospinal fluid from said patient, or an amount of atherosclerotic lesion from said patient, or an amount of mucosal swaps from said patient, or an amount of cells from a tissue culture originating from said patient, or an amount of material which in any way originates from said patient. The in vivo test in a human according to the present invention includes a skin test known in the art such as an intradermal test, e.g similar to a Mantaux test. In certain patients being very sensitive to the test, such as is often the case with children, he test could be non-invasive, such as a superficial test on the skin, e.g. by use of a plaster In the present context, the term 89-101 kDa protein means proteins normally present in the outer membrane of *Chlamydia pneumoniae*, which in SDS-PAGE can be observed as one or more bands with an apparent molecular weight substantially in the range of 89-101 kDa. From the deduced amino acid sequences the molecular size varies from 89.6 to 100.3 kDa.

Within the scope of the present invention are species specific sero-diagnostic tests based on the usage of the genes belonging to the gene family disclosed in the present application.

Preferred embodiments of the present invention relate to species specific diagnostic tests according to the invention, wherein the outer membrane proteins have sequences selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, and SEQ ID NO: 24.

When used in connection with proteins according to the present invention the term "variant" should be understood as a sequence of amino acids which shows a sequence similarity of less than 100% to one of the proteins of the invention. A variant sequence can be of the same size or it can be of a different size as the sequence it is compared to. A variant will typically show a sequence similarity of preferably at least 50%, preferably at least 60%, more preferably at least 70%, such as at least 80%, e.g. at least 90%, 95% or 98%.

The term "sequence similarity" in connection with sequences of proteins of the invention means the percentage of identical and conservatively changed amino acid residues (with respect to both position and type) in the proteins of the invention and an aligned protein of equal of different length. The term "sequence identity" in connection with sequences of proteins of the invention means the percentage of identical amino acid with respect to both position and type in the proteins of the invention and an aligned protein of equal of different length.

Within the scope of the present invention are subsequences of one of the proteins of the invention, meaning a consecutive stretch of amino acid residues taken from SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, or SEQ ID NO: 24. A subsequence will typically comprise at least 100 amino acids, preferably at least 80 amino acids, more preferably at least 70 amino acids, such as 50 amino acids. It might even be as small as 10-50 amino acids, such as 20-40 amino acids, e.g. about 30 amino acids. A subsequence will typically show a sequence homology of at least 50%, preferably at least 60%, more preferably at least 70%, such as at least 80%, e.g. at least 90%, 95% or 98%.

Diagnostic tests according to the invention include immunoassays selected from the group consisting of a direct or indirect EIA such as an ELISA, an immunoblot technique such as a Western blot, a radio immuno assay, and any other non-enzyme linked antibody binding assay or procedure such as a fluorescence, agglutination or precipitation reaction, and nephelometry.

A preferred embodiment of the present invention relates to species specific diagnostic tests according to the invention, said test comprising an ELISA, wherein antibodies against the proteins of the invention or fragments thereof are detected in samples.

A preferred embodiment of the invention, is an ELISA based on detection in samples of antibodies against proteins of the invention. The ELISA may use proteins of the invention, or variants thereof, i.e. the antigen, as coating agent. An ELISA will typically be developed according to standard methods well known in the art, such as methods described in "Antibodies; a laboratory manual", Ed. David Lane Harlow, Cold Spring Habor laboratories (1988), which is hereby incorporated by reference.

Recombinant proteins will be produced using DNA sequences obtained essentially using methods described in the examples below. Such DNA sequences, comprising the entire coding region of each gene in the gene family of the invention, will be cloned into an expression vector from which the deduced protein sequence can be purified. The purified proteins will be analyzed for reactivity in ELISA using both monoclonal and polyclonal antibodies as well as sera from experimentally infected mice and human patient sera.

From the experimentally infected mice sera it is known that non-linear epitopes are recognized predominantly. Thus, it is contemplated that different forms of purification schemes known in the art will be used to analyze for the presence of discontinuous epitopes, and to analyze whether the human immune response is also directed against such epitopes.

Preferred embodiments of the present invention relate to species specific diagnostic tests according to the invention, wherein the nucleic acid fragments have sequences selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, and SEQ ID NO: 23.

In connection with nucleic acid fragments according to the present invention the term "variant" should be understood as a sequence of nucleic acids which shows a sequence homology of less than 100%. A variant sequence can be of the same size or it can be of a different size as the sequence it is compared to. A variant will typically show a sequence homology of at least 50%, preferably at least 60%, more preferably at least 70%, such as at least 80%, e.g. at least 90%, 95% or 98%.

The term "sequence homology" in connection with nucleic acid fragments of the invention means the percentage of matching nucleic acids (with respect to both position and type) in the nucleic acid fragments of the invention and an aligned nucleic acid fragment of equal or different length.

In order to obtain information concerning the general distribution of each of the genes according to the present invention, PCR will be performed for each gene on all available *C. pneumoniae isolates*. This will provide information on the general variability of the genes or nucleic acid fragments of the invention. Variable regions will be sequenced. From patient samples PCR will be used to amplify variable parts of the genes for epidemiology. Non-variable parts will be used for amplification by PCR and analyzed for possible use as a diagnostic test. It is contemplated that if variability is discovered, PCR of variable regions can be used for epidemiology. PCR of non-variable regions can be used as a species specific diagnostic test. Using genes encoding proteins known to be invariable in all known isolates prepared as targets for PCR to genes encoding proteins with unknown function.

Particularly preferred embodiments of the present invention, relate to diagnostic tests according to the invention, wherein detection of nucleic acid fragments is obtained by using nucleic amplification, preferably polymerase chain reaction (PCR).

Within the scope of the present invention is a PCR based test directed at detecting nucleic acid fragments of the invention or variants thereof. A PCR test will typically be developed according to methods well known in the art and will typically comprise a PCR test capable of detecting and differentiating between nucleic acid fragments of the invention. Preferred are quantitative competitive PCR tests or nested PCR tests. The PCR test according to the invention will typically be developed according to methods described in detail in EP B 540 588, EP A 586 112, EP A 643 140 OR EP A 669 401, which are hereby incorporated by reference.

Within the scope of the present invention are variants and subsequences of one of the nucleic acid fragments of the invention, meaning a consecutive stretch of nucleic acids taken from SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 19, SEQ ID NO: 21, or SEQ ID NO: 23. A variant or subsequence will preferably comprise at least 100 nucleic acids, preferably at least 80 nucleic acids, more preferably at least 70 nucleic acids, such as at least 50 nucleic acids. It might even be as small as 10-50 nucleic acids, such as 20-40 nucleic acids, e.g. about 30 nucleic acids. A subsequence will typically show a sequence homology of at least 30%, preferably at least 60%, more preferably at least 70%, such as at least 80%, e.g. at least 90%, 95% or 98%. The shorter the subsequence, the higher the required homology. Accordingly, a subsequence of 100 nucleic acids or lower must show a homology of at least 80%.

A very important aspect of the present invention relates to proteins of the invention derived from *Chlamydia pneumoniae* having amino acid sequences selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, and SEQ ID NO: 24 having a sequence similarity of at least 50%, preferably at least 60%, more preferably at least 70%, such as at least 80%, e.g. at least 90%, 95% or 98% and a similar biological function.

By the term "similar biological function" is meant that the protein shows characteristics similar with the proteins derivable from the membrane proteins of *Chlamydia pneumoniae*. such proteins comprise repeated motifs of GGAI (Gly-Gly-Ala-Ile, amino acids 164-167 of SEQ ID NO:2) (at least 2, preferable at least 3 repeats) and/or conserved positions of tryptophan, (w).

Comparison of the DNA sequences from genes encoding Omp4-15 (SEQ ID NOs:1, 3, 5, 7, 9, 11, 13, 15, 17, 19, 21, 23) shows that the overall similarity between the individual genes ranges between 43-55%. Comparison of the amino acid sequences of Omp4-15 (SEQ ID NOs:2, 4, 6, 8, 10, 12, 14, 16, 18, 20, 22, 24) shows 34-49% identity and 53-64% similarity. The homology is generally scattered along the entire length of the deduced amino acids. However, as seen from FIGS. 8 A-J there are some regions in which the homology is more pronounced. This is seen in the repeated sequence where the sequence GGAI is repeated 4-7 times in the genes. It is interesting that the DNA homology is not conserved for the sequences encoding the four amino acids GGAI (Gly-Gly-Ala-Ile, amino acids 164-167 of SEQ ID NO:2). This may indicate a functional role of this part of the protein and indicates that the repeated structure did not occur by a duplication of the gene. In addition to the four amino acid repeats GGAI (Gly-Gly-Ala-Ile, amino acids 164-167 of SEQ ID NO:2) a region from amino acid 400 to 490 has a higher degree of homology than the rest of the protein, with the conserved sequence FYDPI (Phe-Tyr-Asp-Pro-Ile, amino acids 374-378 of SEQ ID NO:2) occurring in all sequences. As further indication of similarity in function the amino acid tryptophan (W) is perfectly conserved at 4-6 localizations in the C-terminal part of the protein.

Since none of the genes and deduced amino acid sequences of the invention are identical the following is within the scope of the present invention; production of monospecific antibodies, the use of said antibodies for characterizing which C. pneumoniae proteins are expressed, the use of said antibodies for characterizing at which time during developmental life cycle said C. pneumoniae proteins are expressed, and the use of said antibodies for characterizing the precise cellular localization of said C. pneumoniae proteins. Also within the scope of the present invention is the use of monospecific antibodies against proteins of the invention for determining which part of said proteins is surface exposed and how proteins in the C. pneumoniae COMC interact with each other.

Preferred embodiments of the present invention relate to isolated polypeptides which comprise subsequences of the proteins of the invention, said subsequences comprising the sequence GGAI (Gly-Gly-Ala-Ile, amino acids 164-167 of SEQ ID NO:2). Further preferred embodiments of the present invention relate to polypeptides which comprise subsequences of the proteins of the invention, said subsequences comprising the sequence FSGE Phe-Ser-Gly-Glu, amino acids 407-410 of SEQ ID NO:2).

Polypeptides according to the invention will typically be of a length of at least 6 amino acids, preferably at least 15 amino acids, preferably at least 20 amino acids, preferably at least 25 amino acids, preferably at least 30 amino acids, preferably at least 35 amino acids, preferably at least 40 amino acids, preferably at least 45 amino acids, preferably at least 50 amino acids, preferably at least 55 amino acids, preferably at least 100 amino acids.

A very important aspect of the present invention relates to nucleic acid fragments of the invention derived from *Chlamydia pneumoniae*, variants and subsequences thereof.

Another important aspect of the present invention relates to antibodies against the proteins according to the invention, such antibodies including polyclonal monospecific antibodies and monoclonal antibodies against proteins with sequences selected from the group consisting of SEQ ID NO: 2, SEQ ID NO:4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, and SEQ ID NO: 24.

A very important aspect of the present invention relates to diagnostic kits for the diagnosis of infection of a mammal, such as a human, with *Chlamydia pneumoniae*, said kits comprising one or more proteins. with amino acid sequences selected from the group consisting of SEQ ID NO: 2, SEQ ID NO: 4, SEQ ID NO: 6, :SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, and SEQ ID NO: 24.

Another very important aspect of the present invention relates to diagnostic kits for the diagnosis of infection of a mammal, such as a human, with *Chlamydia pneumoniae*, said kits comprising antibodies against a protein with an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, and SEQ ID NO: 24. Antibodies included in a diagnostic kit according to the invention can be polyclonal or monoclonal or a mixture hereof.

Still another very important aspect of the present invention relates to diagnostic kits for the diagnosis of infection of a mammal, such as a human, with *Chlamydia pneumoniae*, said kits comprising one or more nucleic acid fragments with sequences selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, and SEQ ID NO: 23.

An aspect of the present invention relates to a composition for immunizing a mammal, such as a human, against *Chlamydia pneumoniae*, said composition comprising one or more proteins with amino acid sequences selected from the group consisting of SEQ ID NO: 2, SEQ ID NO: 4, SEQ ID NO: 6, SEQ ID NO :8, SEQ ID NO: 10, SEQ ID NO: 12, SEQ ID NO: 14, SEQ ID NO: 16, SEQ ID NO: 18, SEQ ID NO: 20, SEQ ID NO: 22, and SEQ ID NO: 24.

An important role for the proteins of the invention in prevention of infection of a mammal, such as a human, with *C. pneumoniae* is expected. Thus proteins of the invention, including variants and subsequences will be produced, typically by using recombinant techniques; and will then be used as an antigen in immunization of mammals, such as rabbits. Subsequently, the hyper immune sera obtained by the immunization will be analyzed for protection against *C. pneumoniae* infection using a tissue culture assay. In addition it is contemplated that monoclonal antibodies will be produced, typically using standard hybridoma techniques, and analyzed for protection against infection with *C. pneumoniae*.

It is envisioned that particularly interesting and immunogenic epitopes will be found in connection with the proteins of the invention, which will comprise subsequences of said proteins. It is preferred to use isolated polypeptides comprising such subsequences of the proteins of the invention in immunizing a mammal, such as a human, against *chlamydia pneumoniae*.

An important aspect of the present invention relates to the use of proteins with sequences selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, and SEQ ID NO: 24 in diagnosis of infection of a mammal, such as a human, with *Chlamydia pneumoniae*.

A preferred embodiment of the present invention relates to the use of proteins according to the invention in an undenatured form, in diagnosis of infection of a mammal, such as a human, with *Chlamydia pneumoniae*.

A very important aspect of the present invention relates to the use of proteins with sequences selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, and SEQ ID NO: 24, for immunizing a mammal, such as a human, against *Chlamydia pneumoniae*.

A preferred embodiment of the present invention relates to the use of proteins according to the invention in an undenatured form, for immunizing a mammal, such as a human, against *Chlamydia pneumoniae*.

A very important aspect of the present invention relates to the use of nucleic acid fragments with nucleotide sequences selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, and SEQ ID NO: 23 for immunizing a mammal, such as a human, against *Chlamydia pneumoniae*.

It is envisioned that one type of vaccine against *C. pneumoniae* will be developed by using gene-gun vaccination of mice. Typically, different genetic constructs containing nucleic acid fragments, combinations of nucleic acid fragments according to the invention will be used in the gene-gun approach. The mice will then subsequently be analyzed for production of both humoral and cellular immune response and for protection against infection with *C. pneumoniae* after challenge herewith.

In line with this, the invention also relates to the uses of the proteins of the invention as a pharmaceutical (a vaccine) as well as to the uses thereof for the preparation of a vaccine against infections with *Chlamydia pneumoniae*.

Preparation of vaccines which contain protein sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables either as liquid solutions or suspensions; solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like, and combinations thereof. In addition, if desired, the vaccine may contain minor amounts of auxiliary substances such as wetting or emulsifying agents, pH buffering agents, or adjuvants which enhance the effectiveness of the vaccines.

The vaccines are conventionally administered parenterally, by injection, for example, either subcutaneously or intramuscularly. Additional formulations which are suitable for other modes of administration include suppositories and, in some cases, oral formulations. These compositions take the form of solutions, suspensions, tablets, pills, capsules, sustained release formulations or powders and contain 10-95% of active ingredient, preferably 25-70%, and optionally a suitable carrier.

The protein sequences may be formulated into the vaccine as neutral or salt forms known in the art. The vaccines are administered in a manner compatible with the dosage formulation, and in such amount as will be therapeutically effective and immunogenic. The quantity to be administered depends on the subject to be treated. Suitable dosage ranges are of the order of several hundred micrograms active ingredient per vaccination with a preferred range from about 0.1 μg to 1000 μg. The immune response may be enhanced if the vaccine further comprises an adjuvant substance as known in the art. Other possibilities involve the use of immunomodulating substances such as lymphokines (e.g. IFN-γ, IL-2 and IL-12) or synthetic IFN-γ inducers such as poly I:C in combination with the above-mentioned adjuvants.

It is also possible to produce a living vaccine by introducing, into a non-pathogenic microorganism, at least one nucleic acid fragment encoding a protein fragment or protein of the invention, and effecting expression of the protein fragment or the protein on the surface of the microorganism (e.g. in the form of a fusion protein including a membrane anchoring part or in the form of a slightly modified protein or protein fragment carrying a lipidation signal which allows anchoring in the membrane). The skilled person will know how to adapt relevant expression systems for this purpose.

Another part of the invention is based on the fact that recent research have revealed that a DNA fragment cloned in a vector which is non-replicative in eukaryotic cells may be introduced into an animal (including a human being) by e.g. intramuscular injection or percutaneous administration (the so-called "gene gun" approach). The DNA is taken up by e.g. muscle cells and the gene of interest is expressed by a promoter which is functioning in eukaryotes, e.g. a viral promoter, and the gene product thereafter stimulates the immune system. These newly discovered methods are reviewed in Ulmer et al., 1993, which hereby is included by reference.

Thus, a nucleic acid fragment encoding a protein or protein of the invention may be used for effecting in vivo expression of antigens, i.e. the nucleic acid fragments may be used in so-called DNA vaccines. Hence, the invention also relates to a vaccine comprising a nucleic acid fragment encoding a protein fragment or a protein of the invention, the vaccine effecting in vivo expression of antigen by an mammal, such as a human, to whom the vaccine has been administered, the amount of expressed antigen being effective to confer substantially increased resistance to infections with *Chlamydia pneumoniae* in an mammal, such as a human.

The efficacy of such a "DNA vaccine" can possibly be enhanced by administering the gene encoding the expression product together with a DNA fragment encoding a protein which has the capability of modulating an immune response. For instance, a gene encoding lymphokine precursors or lymphokines (e g.IFN-γ, IL-2, or IL-12) could be administered together with the gene encoding the immunogenic protein fragment or protein, either by administering two separate DNA fragments or by administering both DNA fragments included in the same vector. It is also a possibility to administer DNA fragments comprising a multitude of nucleotide sequences which each encode relevant epitopes of the protein fragments and proteins disclosed herein so as to effect a continuous sensitization of the immune system with a broad spectrum of these epitopes.

The following experimental non-limiting examples are intended to illustrate certain features and embodiments of the invention

LEGENDS TO FIGURES

FIG. 1. The figure shows electron microscopy of negative stained purified *C. pneumoniae* EB (A) and purified OMC (B).

Figure 2:
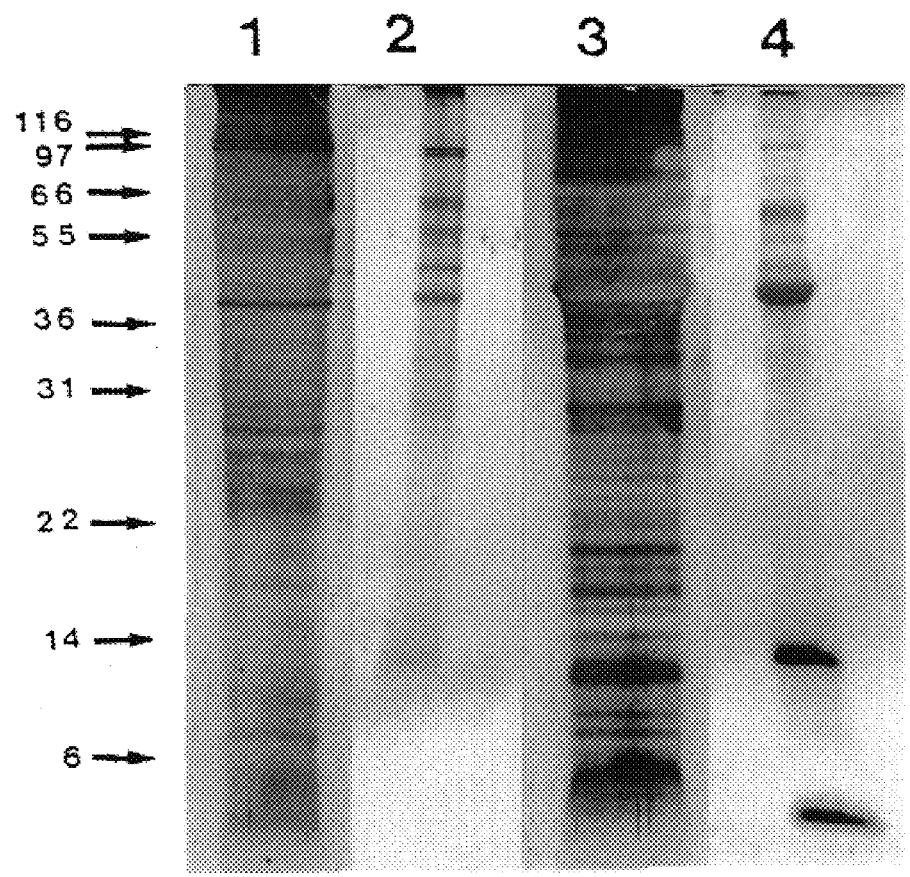

FIG. 2. The figure shows silver stained 15% SDS-PAGE of purified EB and OMC. Lane 1, purified *C. pneumoniae* EB; lane 2, *C. pneumoniae* OMC; lane 3, purified *C. trachomatis* EB; and lane 4 *C. trachomatis* OMC.

Figure 3:
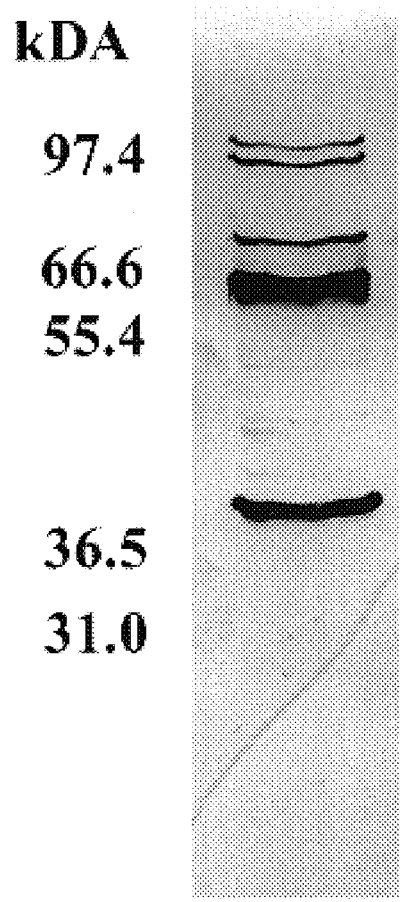

FIG. 3. The figure shows immunoblotting of *C. pneumoniae* EB separated by 10% SDS-PAGE, transferred to nitrocellulose and reacted with rabbit anti *C. pneumoniae* OMC.

Figure 4:
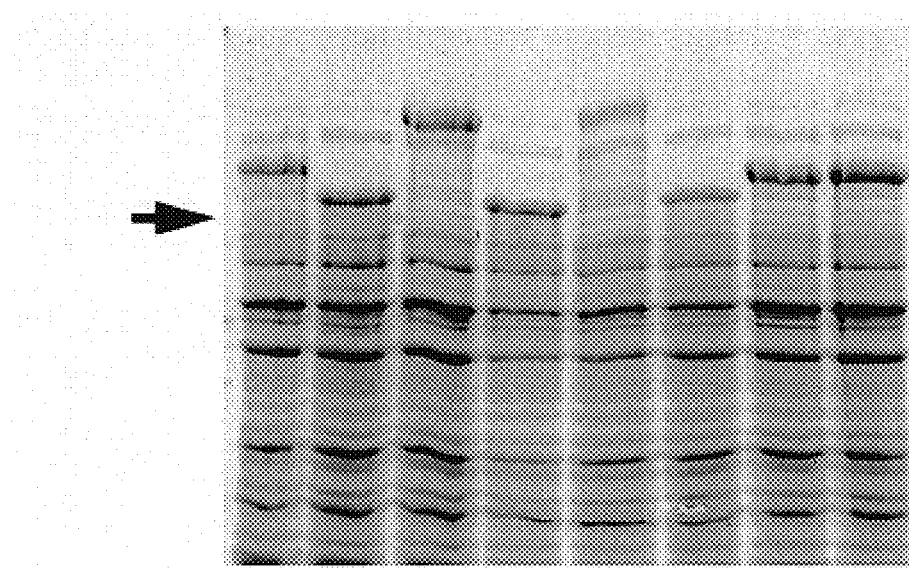

FIG. 4. The figure shows coomassie blue stained 7.5% SDS-PAGE of recombinant pEX that were detected by the rabbit anti *C. pneumoniae* serum. Arrow indicated the localization of the 117 kDa b-galactosidase protein.

Figure 5:
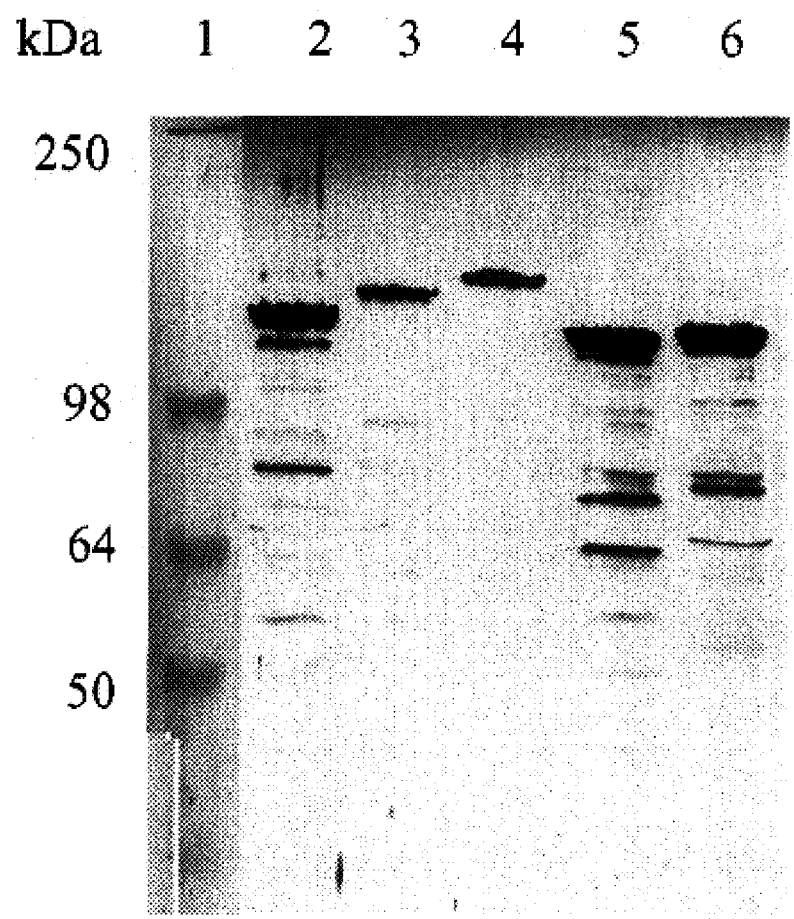

FIG. 5. The figure shows immunoblotting of recombinant pEX colones detected by colony blotting separated by 7.5%. SDS-PAGE and transferred to nitrocellulose and reacted with rabbit anti *C. pneumoniae* OMC. Lane 1, seablue molecular weight standard. Lane 2-6 pEX clones cultivated at 42° C. to induce the production of the b-galactosidase fusion proteins.

Figure 6:
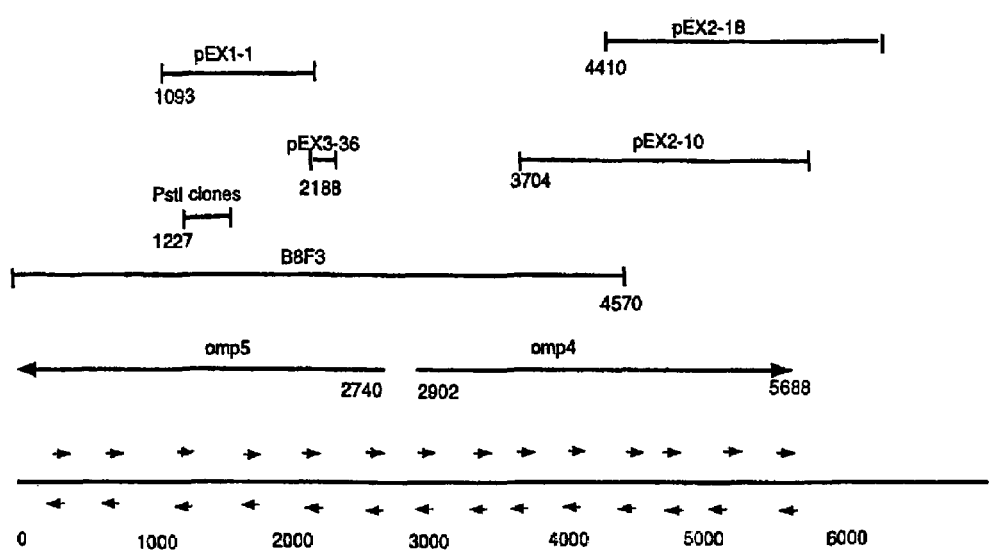

FIG. 6. The figure shows sequencing strategy for Omp4 (SEQ ID NO:1) and Omp5 (SEQ ID NO:3). Arrows indicates primers used for sequencing.

Figure 7:
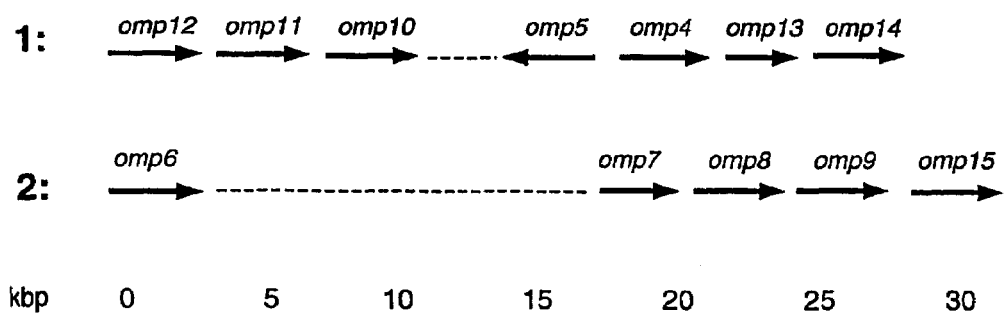

FIG. 7. *C. pneumoniae* omp genes. The genes are arranged in two clusters. In cluster 1 Omp12, 11, 10, 5, 4, 13, and 14 (SEQ ID NOs:17, 15, 13, 3, 1, 19, 21) are found. In cluster 2 are found Omp6, 7, 8, 9, and 15 (SEQ ID NOs:5, 7, 9, 11, 23).

FIGS. 8 A-J. The figure shows alignment of *C. pneumoniae* Omp4-15 (SEQ ID NOs:2, 4, 6, 8, 10, 12, 14, 16, 18, 20, 22, 24), using the program pileup in the GCG package.

Figure 9:
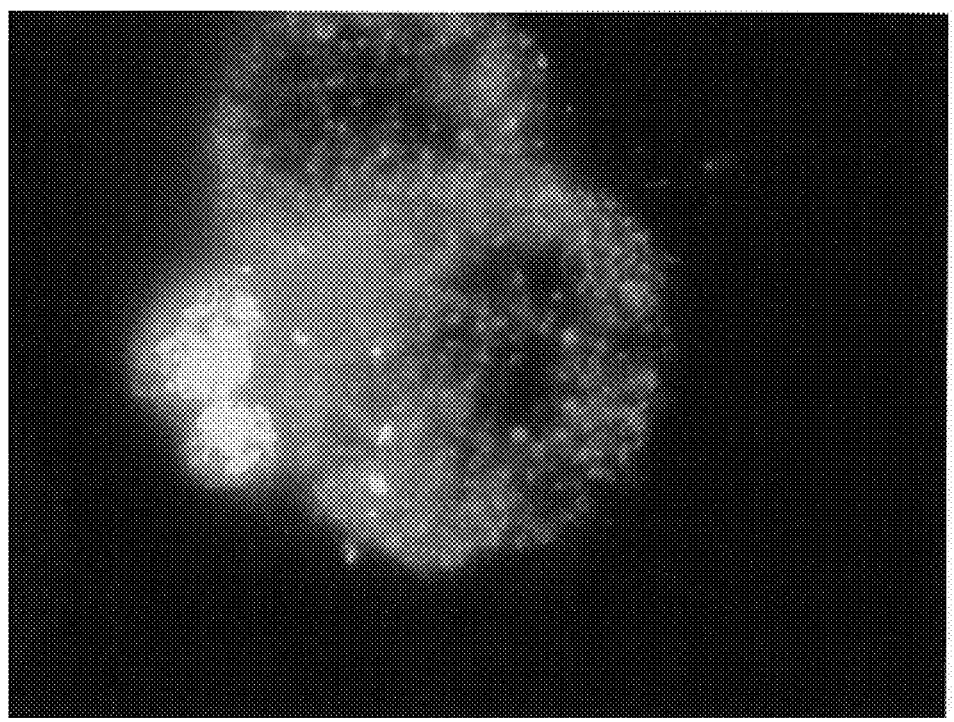

FIG. 9. The figure shows immunofluorescence of *C. pneumoniae* infected HeLa, 72 hrs. after infection, reacted with mouse monospecific anti-serum against pEX3-36 fusion protein. pEX3-36 is a part of the Omp5 gene (SEQ ID NO:3).

Figure 10:
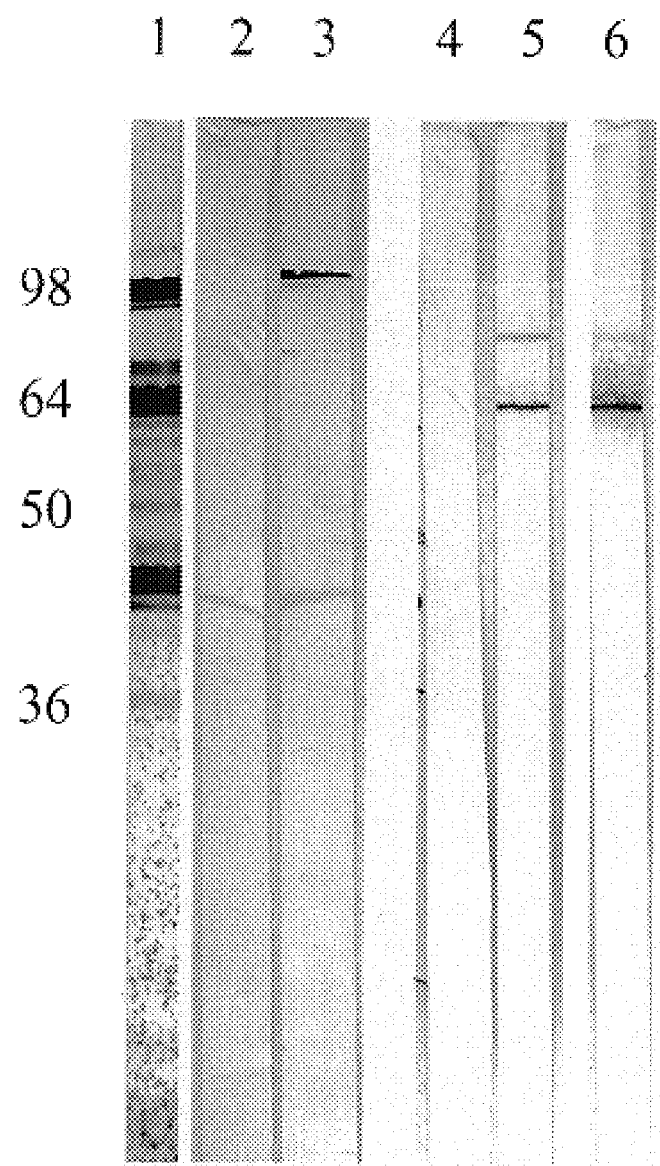

FIG. 10. The figure shows immunoblotting of *C. pneumoniae* EB, lane 1-3 heated to 100° C. in SDS-sample buffer, lane 4-6 unheated. Lane 1 reacted with rabbit anti *C. pneumoniae* OMC; lane 2 and 4 pre-serum; lane 3 and 5 polyclonal rabbit anti pEX1-1 fusion protein; lane 6 MAb 26.1.

Figure 11:
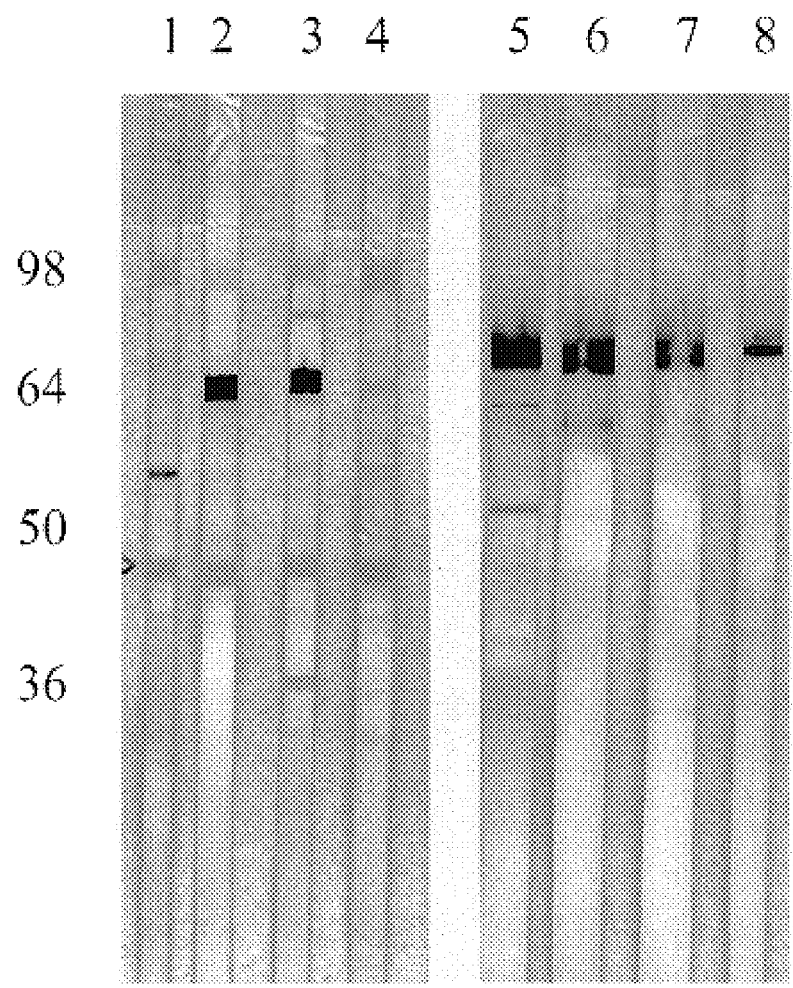

FIG. 11. The figure shows immunoblotting of *C. pneumoniae* EB, lane 1-4 heated to 100° C. in SDS-sample buffer, lane 5-6 unheated. Reacted with serum: from C57-black mice 14 days after infection with $10^7$ CFU of *C. pneumoniae*. Lane 1 and 5 mouse 1; lane 2 and 6 mouse 2; lane 3 and 5 mouse 3; and lane 4 and 8 mouse 4.

Figure 12:
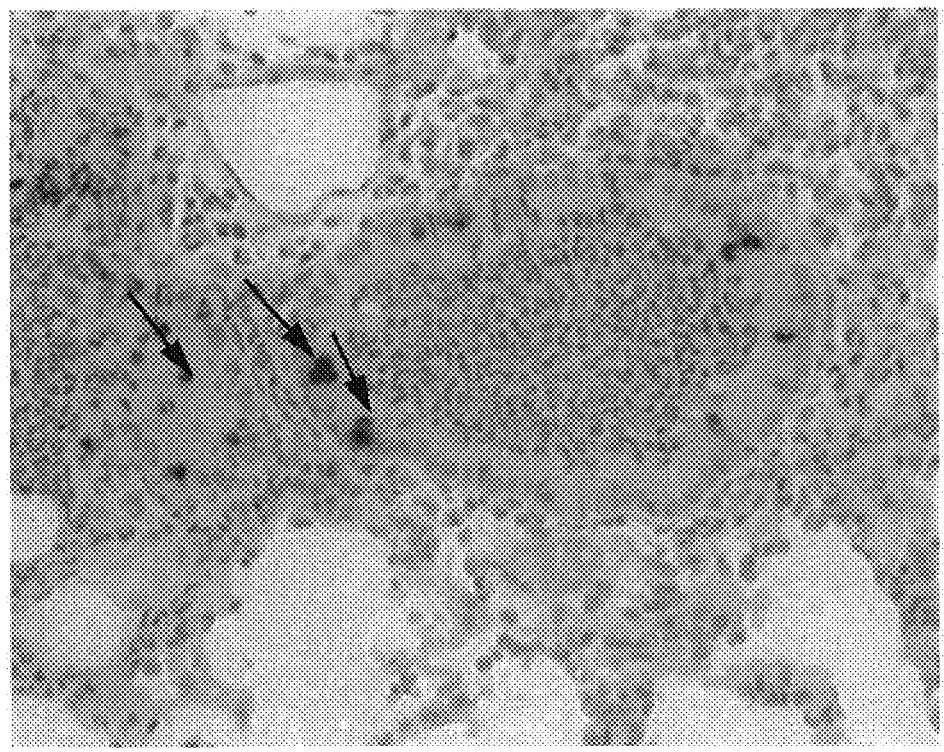

FIG. 12. The figure shows immunohistochemistry analysis of mouse lung tissue with *C. pneumoniae* inclusions present both in the bronchial epithelium and in the lung parenchyma (arrows).

EXAMPLE 1

Cloning of the genes encoding the 98/95 kDa *C. pneumoniae* COMC proteins

Purification of *C. pneumonia* EBs and COMC

*C. pneumoniae* was cultivated in HeLa cells. Cultivation was done according to the specifications of Miyashita and Matsumoto (1992), with the modification that centrifugation of supernatant and of the later precipitate and turbid bottom layer was carried out at 100,000×g. The microorganism attached to the HeLa cells by 30 minutes of centrifugation at 1000×g, after which the cells were incubated in RPMI 1640 medium (Gibco BRL, Germany cat No. 51800-27), containing 5% foetal calf serum (FCS, Gibco BRL, Germany Cat No. 10106.169) gentamicin for two hours at 37° C. in 5% CO2 atmosphere. The medium was changed to medium that in addition contained 1 mg per ml of cycloheximide. After 48 hours of incubation a coverslip was removed from the cultures and the inclusion was tested with an antibody specific for *C. pneumoniae* (MAb 26.1) (Christiansen et al. 1994) and a monoclonal antibody specific for the species *C. trachomatis* (MAb 32.3, Loke diagnostics, Arhus Denmark) to ensure that no contamination with *C. trachomatis* had occurred. The HeLa cells were tested by Hoechst stain for Mycoplasma contamination as well as by culture in BEa and BEg medium (Freund et al., 1979). Also the *C. pneumoniae* stocks were also tested for Mycoplasma contamination by cultivation in BEa and BEg medium. No contamination with *C. trachomatis*, Mycoplasmas or bacteria were detected in cultures or cells. 72 hours post-infection the monolayer was washed in PBS, the cells were loosened in PBS with a rubber policeman, and the *Chlamydia* were liberated from the host cell by sonication. The *C. pneumoniae* EBs and RBs were purified on discontinuous density gradients (Miyashita et al. (1992)). The purity of the *Chlamydia* EBs were verified by negative staining and electronmicroscopy (FIG. 1), only particles of a size of 0.3 to 0.5 mm were detected in agreement with the structure of *C. pneumonia* EBs.

The purified *Chlamydia* EBs were subjected to sarkosyl extraction as described by Caldwell et al (1981) with the modification that a brief sonication was used to suspend the COMC. The purified COMC was tested by electronmicroscopy and negative staining (FIG. 1), where a folded outer membrane complex was seen.

SDS-PAGE analysis of purified EBs and COMC

The proteins from purified EBs and *C. pneumoniae* OMC were separated on 15% SDS-polyacrylamide gel, and the gel was silver stained (FIG. 2), in lane 1 it is seen that the purified EBs contain major proteins of 100/195 kDa and a protein of 38 kDa, in the purified COMC (lane 2) these two protein groups are also dominant. In addition, proteins with a molecular weight of 62/60 kDa, 55 kDa, and 12 kDa have been enriched in the COMC preparation. When the purified *C. pneumoniae* EBs are compared to purified *C. trachomatis* EB (lane 3) it is seen that predominant protein in the *C. trachomatis* EB is the major outer membrane protein (MOMP), and it is also the dominant band in the COMC preparation of *C. trachomatis* (lane 4), and Omp2, of 60/62 kDa as well as Omp3 at 12 kDa are seen in the preparation. However, no major bands with a size of 100/95 kDa are detected as in the *C. pneumoniae* COMC preparation.

Production of rabbit polyclonal antibodies against *C. pneumoniae* COMC

To ensure production of rabbit antibodies that would recognize all the *C. pneumoniae* proteins in immuno-blotting and colony-blotting 10 μg of COMC antigen was dissolved in 20 μl of SDS sample buffer and thereafter divided into 5 vials. The dissolved antigen was further diluted in one ml of PBS and one ml of Freund incomplete adjuvant (Difco laboratories, USA cat. No. 0639-60-6) and injected into the quadriceps muscle of a New Zealand white rabbit. The rabbit was given three times intramuscular injections at an interval of one week, and after further three weeks the dissolved COMC protein, diluted in one ml PBS was injected intravenously, and the procedure was repeated two weeks later. Eleven weeks after the beginning of the immunization, the serum was obtained from the rabbit. Purified *C. pneumoniae* EBs were separated by SDS-PAGE, and the proteins were electrotransferred to nitrocellulose membrane. The membrane was blocked and immunostained with the polyclonal COMC antibody (FIG. 3). The serum recognized proteins with a size of 100/95, 60 and 38 kDa in the EB preparation. This is in agreement with the sizes of the outer membrane proteins.

Cloning of the COMC proteins

Due to the cultivation of *C. pneumoniae* in HeLa cells, contaminating host cell DNA could be present in the EB preparations. Therefore, the purified EB preparations were treated with DNAse to remove contaminating DNA. The *C.* pneumoniae DNA was then purified by CsCl gradient centrifugation. The *C. pneumoniae* DNA was partially digested with Sau3A and the fractions containing DNA fragments with a size of approx. 0.5 to 4kb were cloned into the expression vector-system pEX (Boehringer, Germany cat. No. 1034 766, 1034 774, 1034 782). The pEX vector system has a β-galactosidase gene with multiple cloning sites in the 3' end of the β-galactosidase gene. Expression of the gene is regulated by the PR promoter, so the protein expression can be induced by elevating the temperature from 32 to 42° C. The colonies of recombinant bacteria were transferred to nitrocellulose membranes, and the temperature was increased to 42° C. for, two hours. The bacteria were lysed by placing the nitrocellulose membranes on filters soaked in 5% SDS. The colonies expressing outer membrane proteins were detected with the polyclonal antibody raised against *C. pneumoniae* COMC. The positive clones were cultivated in suspension and induced at 42° C. for two hours. The protein profile of the clones were analysed by SDS-PAGE, and increases in the size of the induced b-galactosidase were observed (FIG. 4). In addition, the proteins were electrotransferred to nitrocellulose membranes, and the reaction with the polyclonal serum against COMC was confirmed (FIG. 5).

Sequencing of positive COMC clones

To characterize the pEX clones, the inserted *C. pneumoniae* DNA was sequenced. The resulting DNA sequences were searched against the prokaryotic sequences in the GenEmbl database. The search identified 6 clones as part of the Omp2 gene, and 2 clones as part of the Omp3 gene, and 2 clones as part of the MOMP gene, indicating that COMC proteins had been successfully cloned. Furthermore, 32 clones were obtained, containing DNA sequences not found in the GenEmbl database. These sequences could, however, be clustered in two contics of 6 and 4 clones, and three clones were identical. In addition 19 clones were found with no overlap to the contics (FIG. 7). To obtain more sequence data for the genes, *C. pneumoniae* DNA. was totally digested with BamHI restriction enzyme, and the fragments were cloned into the vector pBluescript. The ligated DNA was electrotransformed into *E. coli* XL 1-Blue and selected on plates containing Ampicillin. The recombinant bacterial colonies were transferred to a nitrocellulose membrane, and colony hybridisation was performed using the inserts of pEX 1-1 clone as a probe. A clone containing a single BamHI fragment of 4.5 kb was found, and the hybridisation to the probe was confirmed by Southern blotting. The insert of the clone was sequenced bi-directionally using synthetic primers for approx. each 300 bp. The sequence of the BamHI fragment made it possible to join the two contics of pEX clones. Totally, together with the pEX clones it was possible to assemble 6.5 kb DNA sequence, encoding two new COMC proteins. (FIG. 6)

Figure 8A:
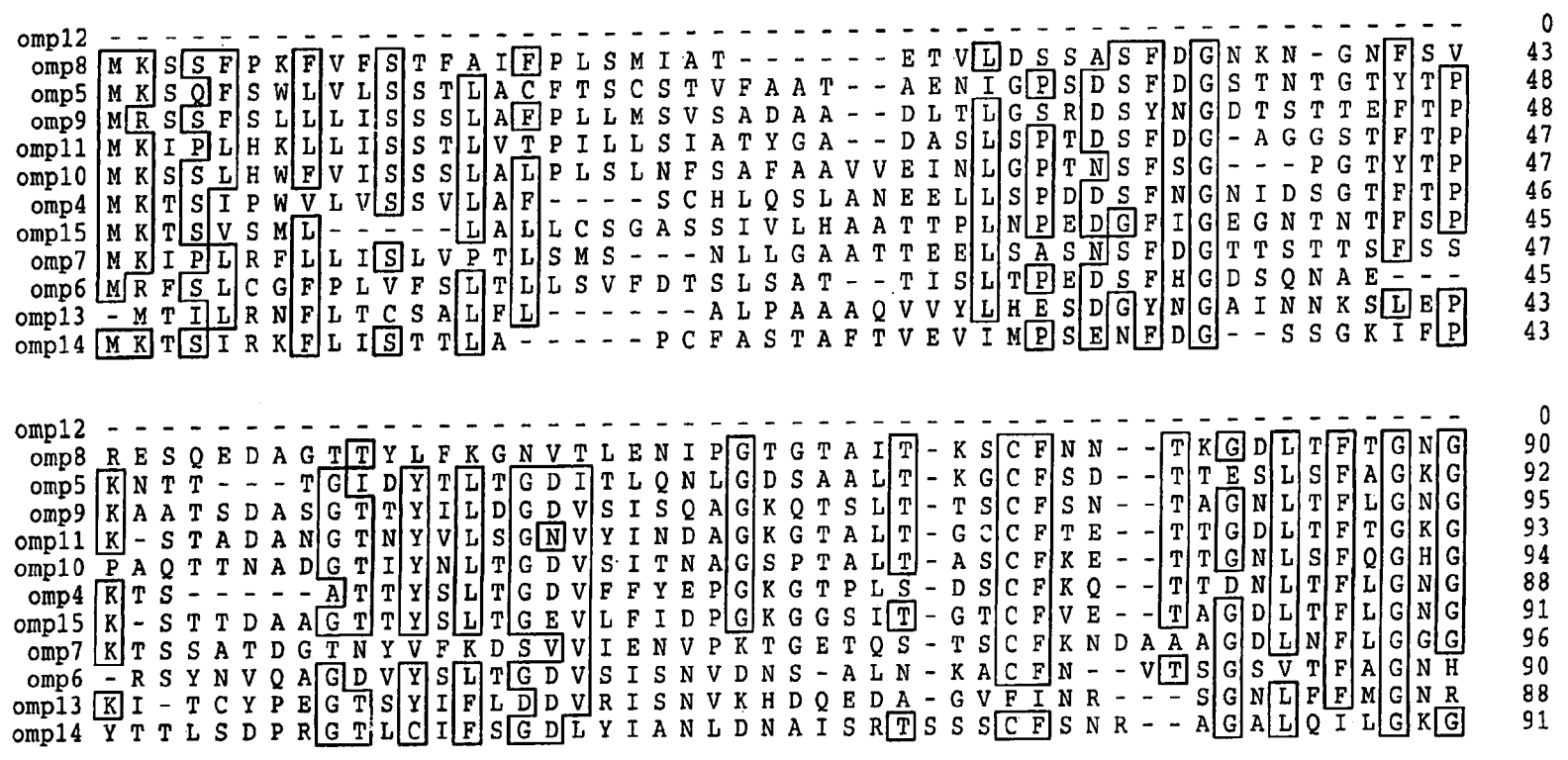
Figure 8B:
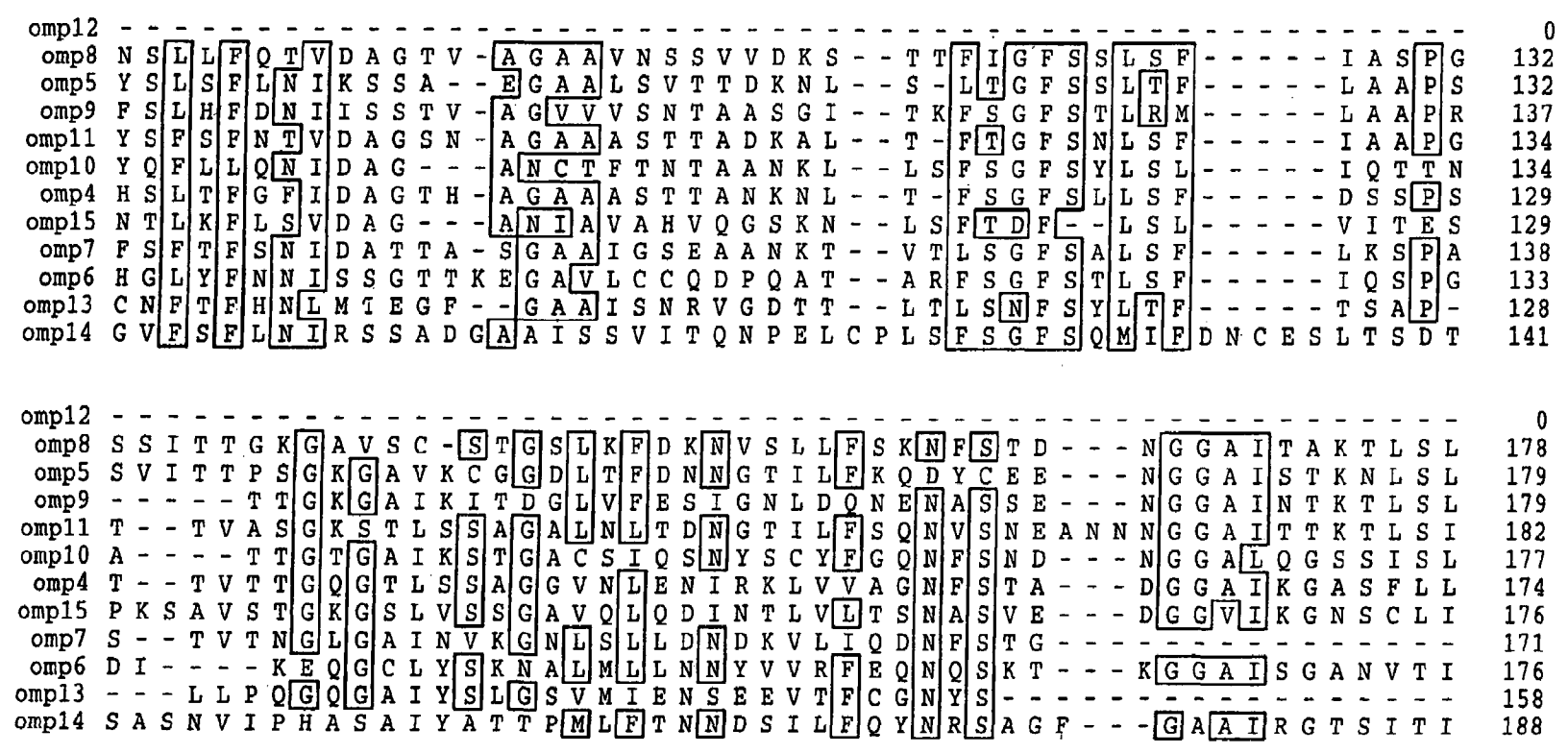
Figure 8C:
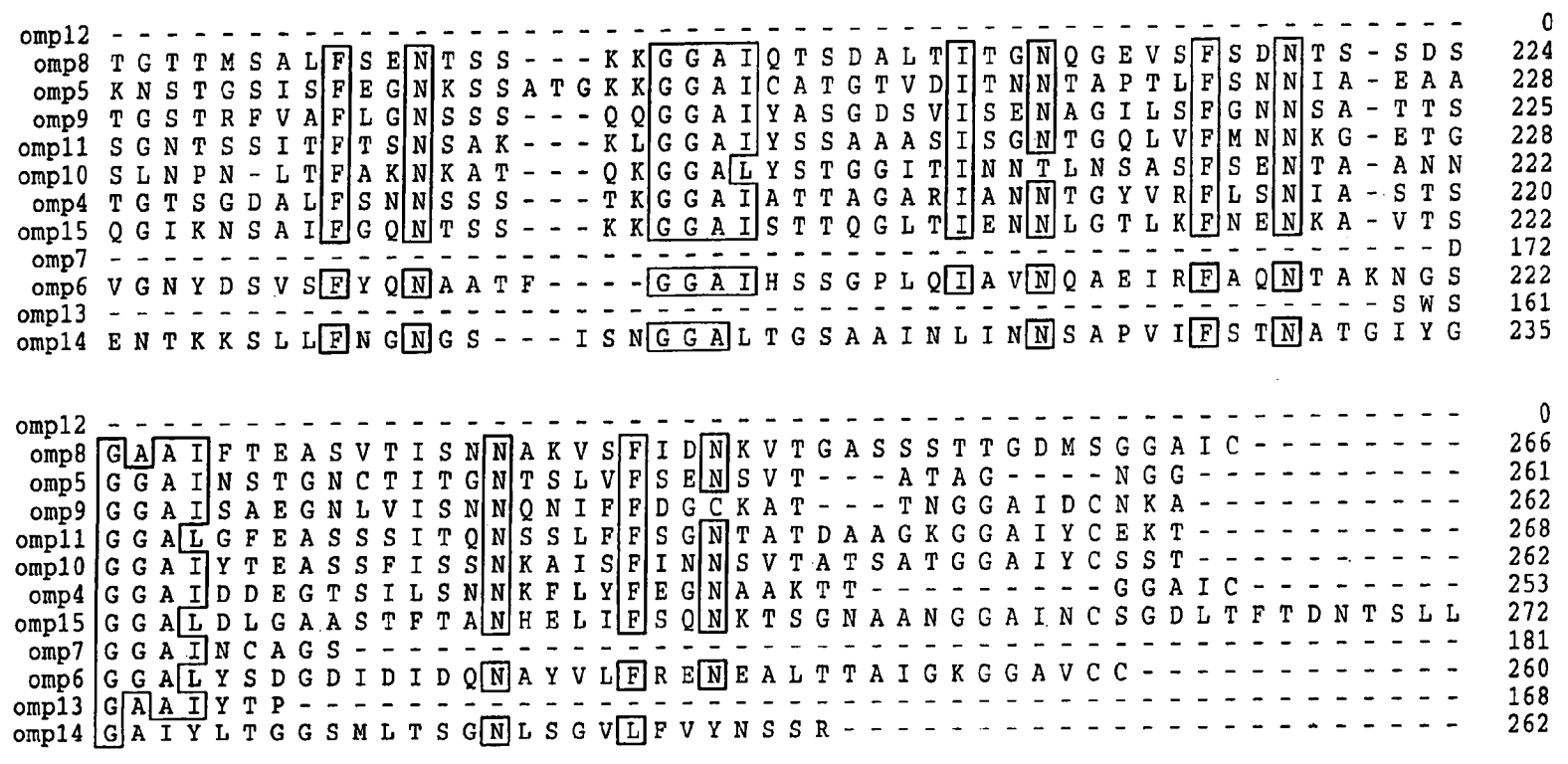
Figure 8D:
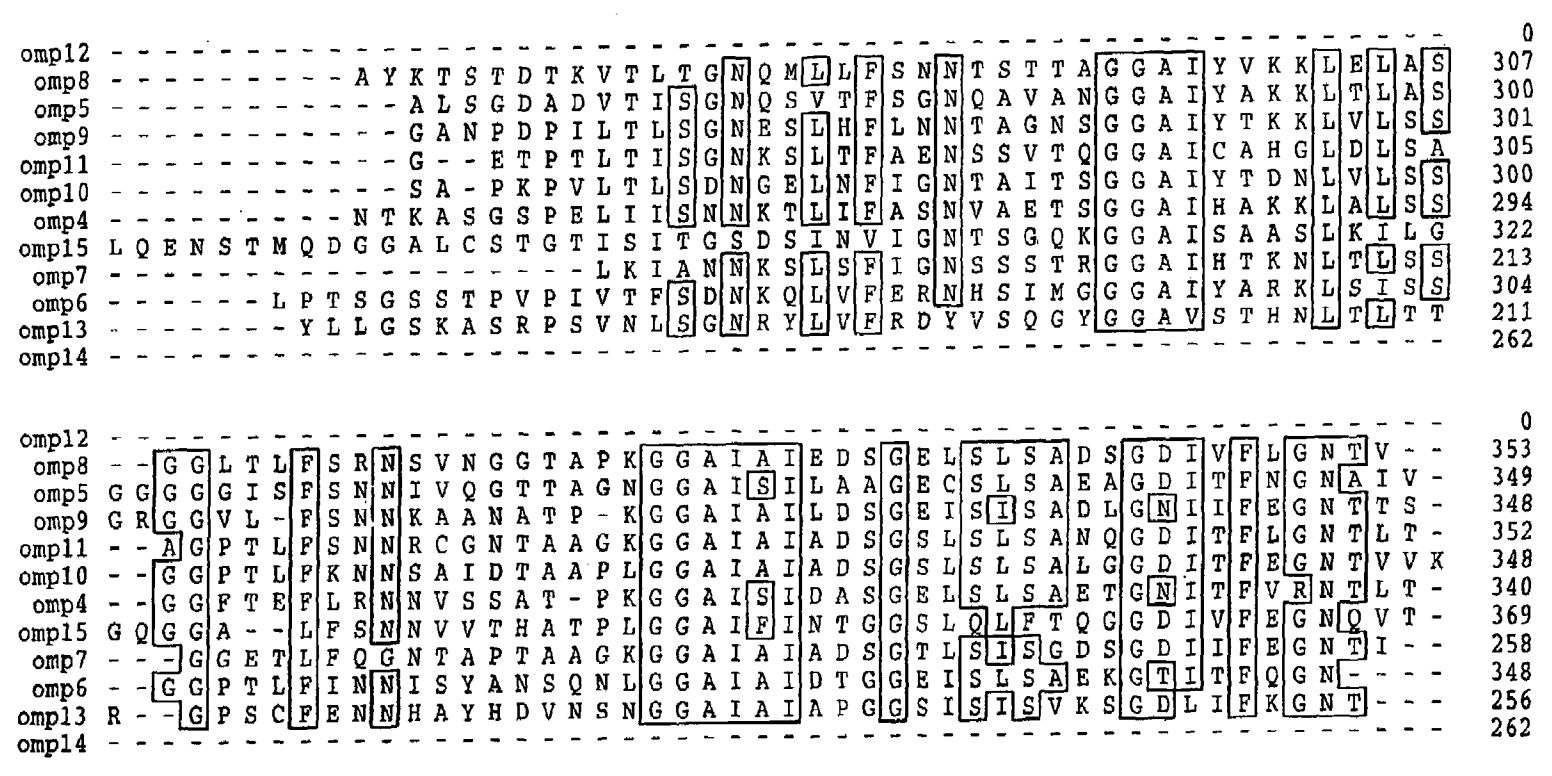
Figure 8E:
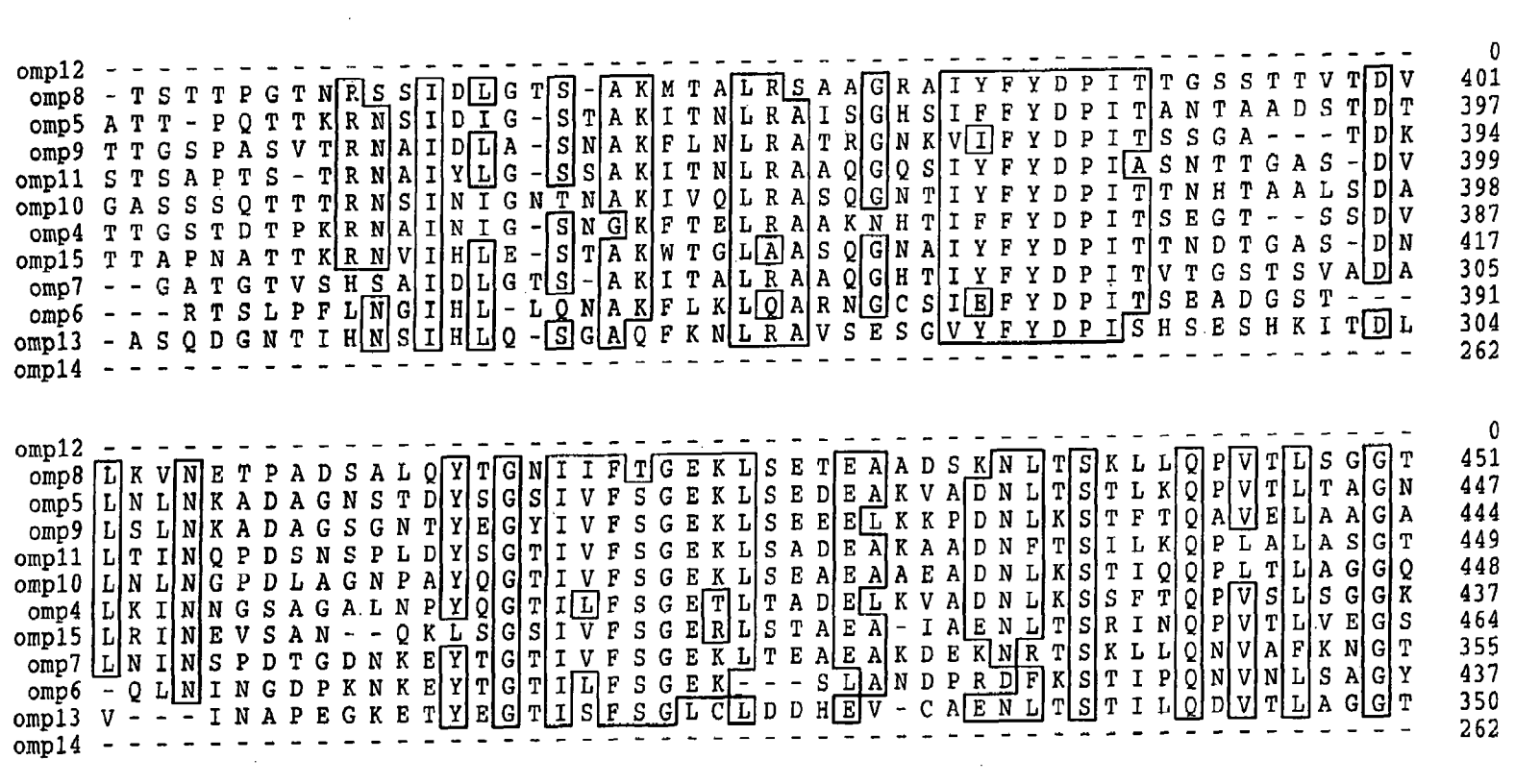
Figure 8F:
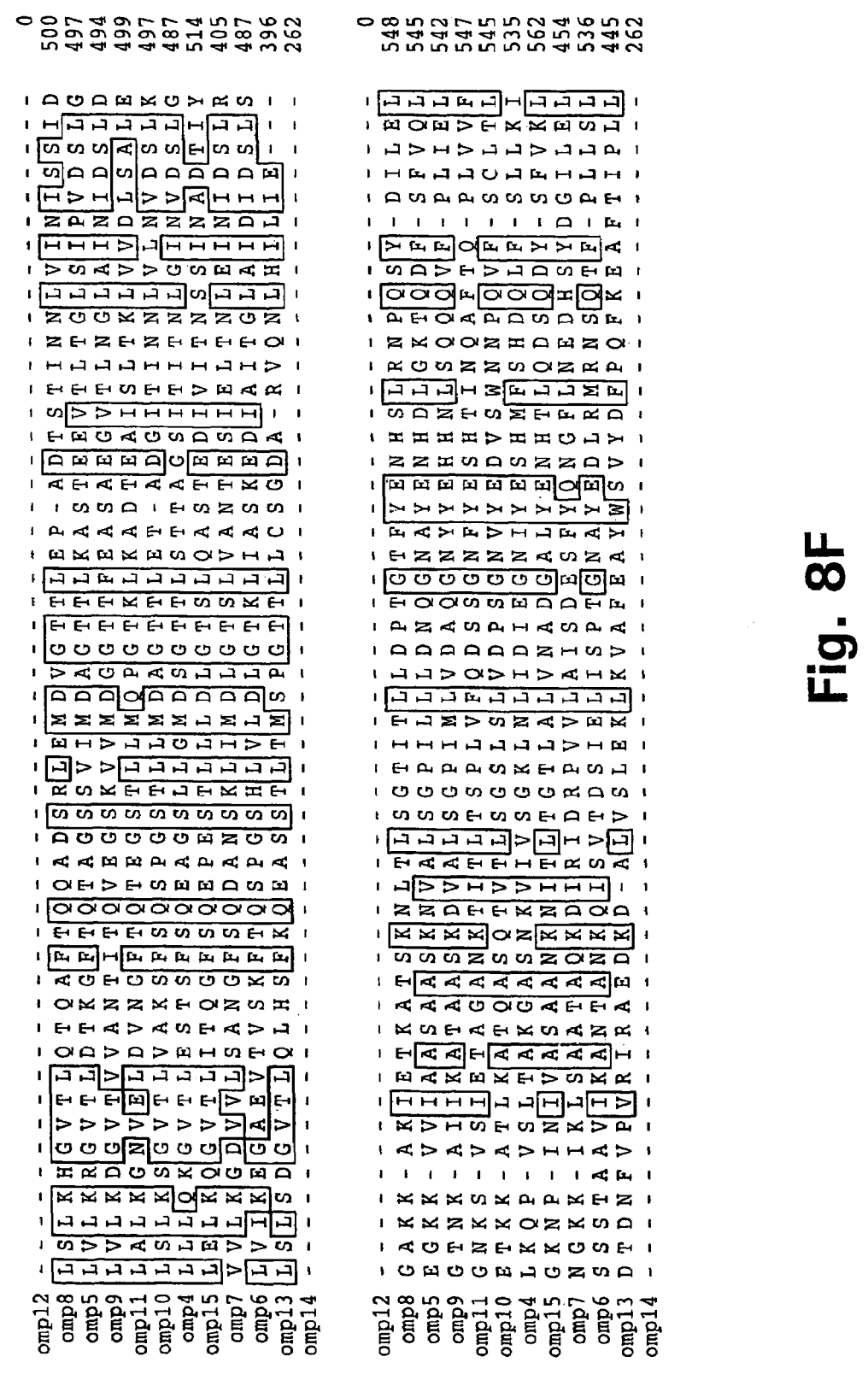
Figure 8G:
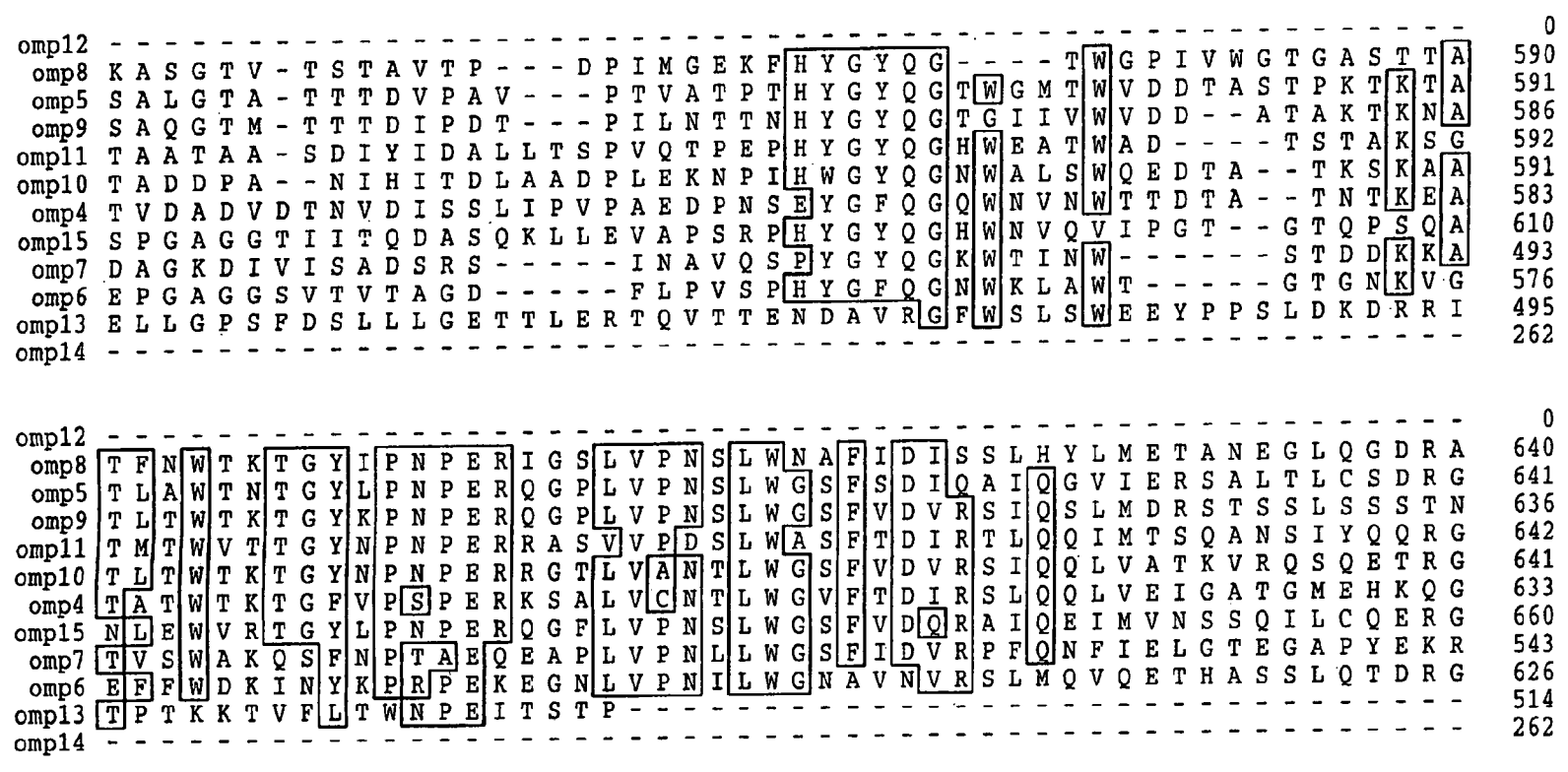
Figure 8H:
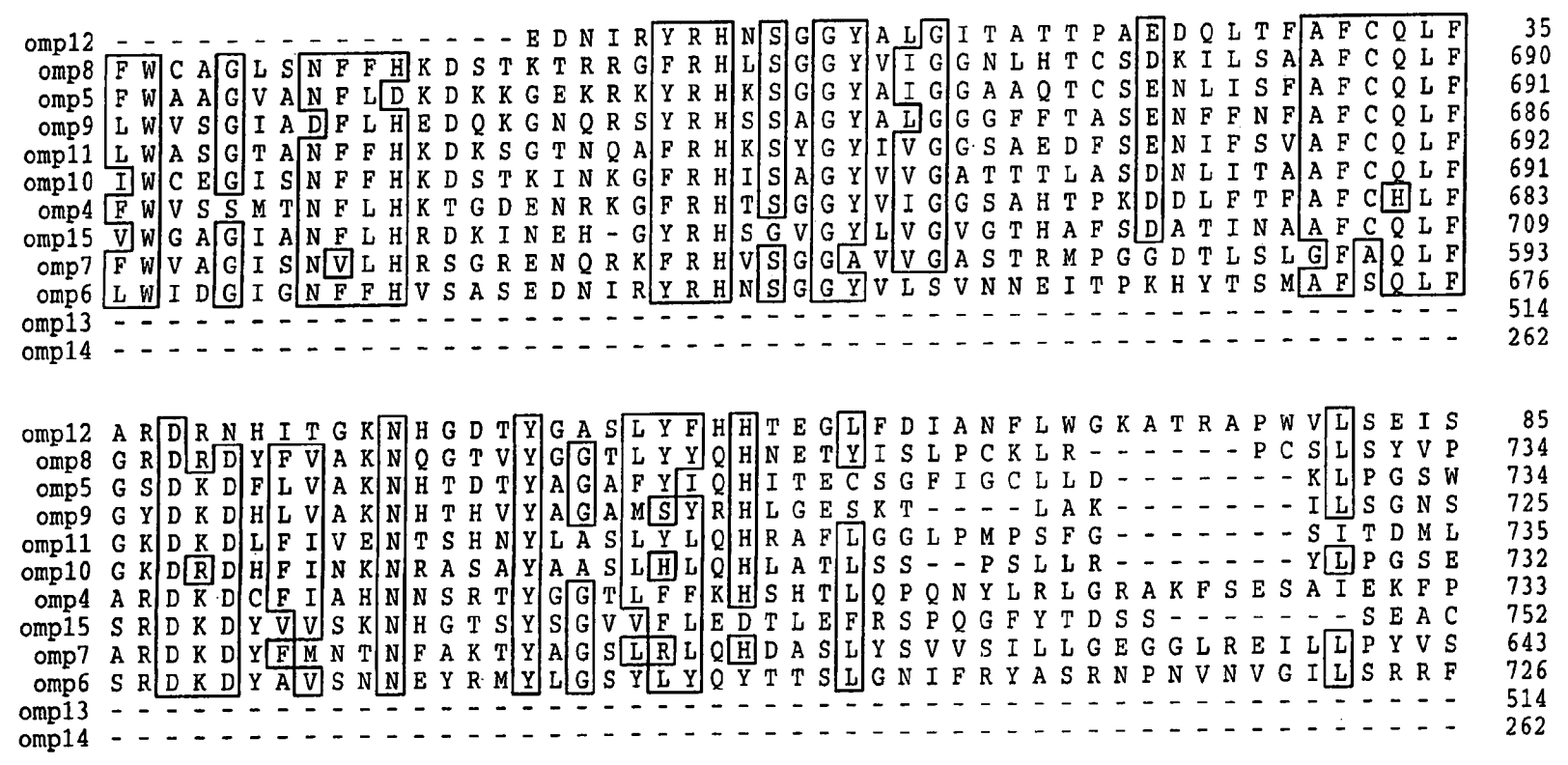
Figure 8J:
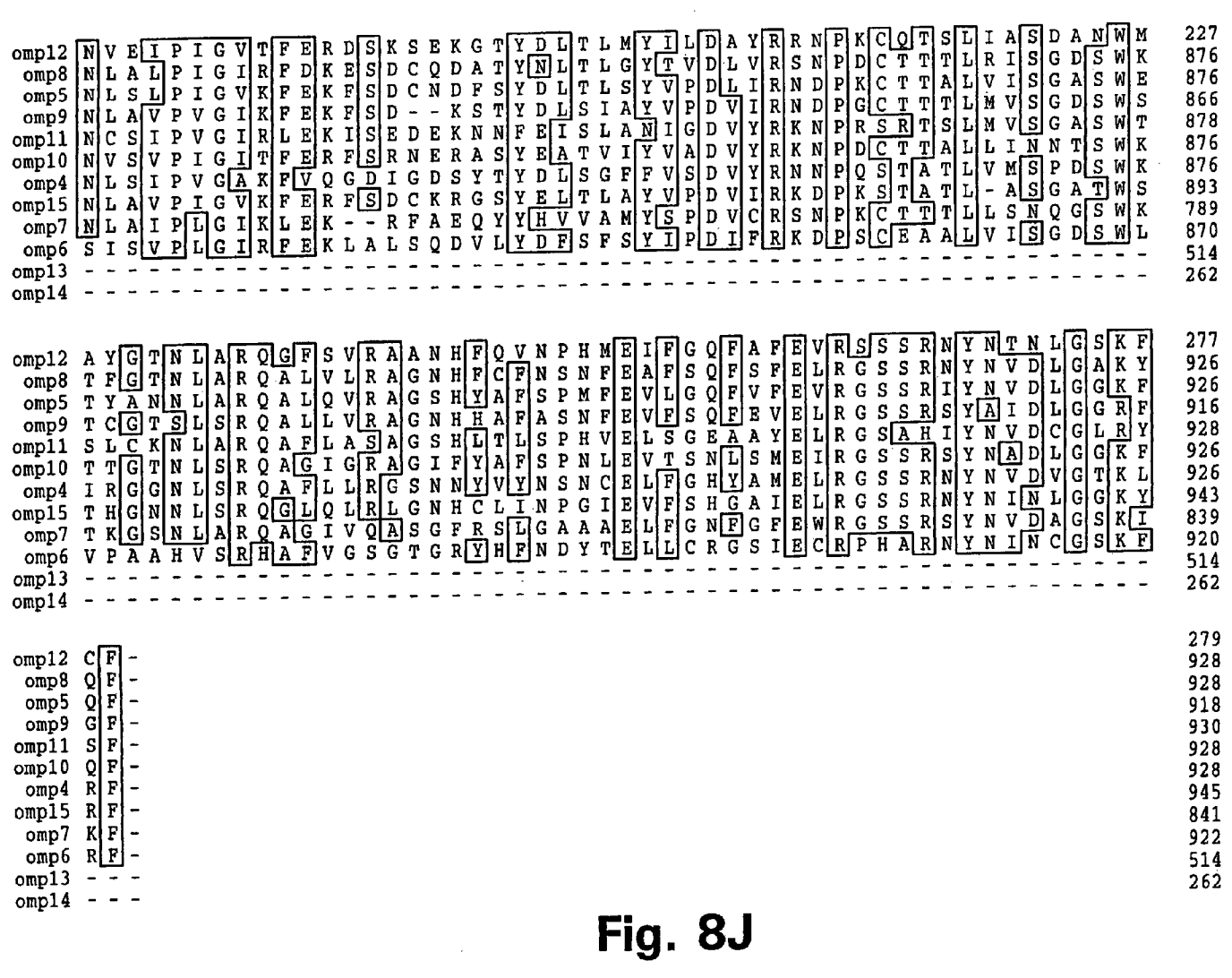

Additional sequences were obtained by PCR performed on purified *C. pneumoniae* DNA with primers both from the known Omp genes and from other known genes. The obtained PCR products were sequenced, The sequence organisation is shown in FIG. 7. Additional 8 Omp genes were detected. The alignment of the deduced amino acid sequences are shown in FIGS. 8A and B.

Analysis of DNA sequence

The DNA sequence encoding the Omp4-15 proteins (SEQ ID NOs:2, 4, 6, 8, 10, 12, 14, 16, 18, 20, 22, 24) with a size of 89.6-100.3 kDa (and for Omp13 (SEQ ID NO:20) : 56.1 kDa) . The Omp4 (SEQ ID NO:1) and Omp5 (SEQ ID NO:3) DNAs were transcribed in opposite directions. Downstream of the coding sequence of the Omp4 gene (SEQ ID NO:1) a possible termination structure was located. The 3' tend of the Omp5 gene (SEQ ID NO:3) was not cloned due to the presence of the BamHI restriction enzyme site positioned within the gene. The amino acid (translated DNA) sequences of Omp4 (SEQ ID NO:2) and Omp5 (SEQ ID NO:4) were compared by use of the gap programme in the GCG package (Wisconsin package, version 8.1-UNIX, August 1995, sequence analysis software package). The two translations had an amino acid identity of 41% (similarity 61%), and a possible cleavage site for signal peptidase 1 was present at amino acid 17 in Omp4 (SEQ ID NO:2) and amino acid 25 in Omp5 (SEQ ID NO:4). When the amino acid sequence encoded by two other pEX clones were compared to the sequence of Omp4 (SEQ ID NO:2) and Omp5 (SEQ ID NO:4) they also had amino acid homology to the genes. It is seen that the two clones have homology to the same area in the Omp4 (SEQ ID NO:2) and Omp5 (SEQ ID NO:4) proteins. Consequently, the pEX clones must have originated from two additional genes. Therefore these genes were named Omp6 (SEQ ID NO:6) and Omp7 (SEQ ID NO:8). Similar analyses were performed with the other genes. In contrast to what was seen for Omp4 (SEQ ID NO:2) and 5 SEQ ID NO:4) none of the other putative omp proteins had a cleavage site for signal peptides.

EXAMPLE 2

Polyclonal monospecific antibodies against pEX fusion proteins and full length recombination+Omp4 (SEQ ID NO:2)

To investigate the topology of the Omp4-7 proteins (SEQ ID NOs:2, 4, 6, 8), representative pEX clones, were selected from each gene. The fusion proteins of β-galactosidase/omp were induced, and the proteins were partially purified as inclusion bodies. Balb/c mice were immunized three times intramuscular with the antigens at an interval of one week, and after six weeks the serum was obtained from the mice. HeLa cells were infected with the *C. pneumoniae*. 72 hours after the infection the mono-layers were fixed with 3.7% formaldehyde. This treatment makes the outer membrane of the *Chlamydia* impermeable for antibodies due to the extensive cross-linking of the outer membrane proteins by the formaldehyde. The HeLa cells were permeabilized with 0.2% Triton X100, the monolayers were washed in PBS, then incubated with 20% (v/v) FCS to inactivate free radicals of the formaldehyde. The mice sera were diluted 1:100 PBS with 20% (v/v) FCS and incubated with the monolayers for half an hour. The monolayers were washed in PBS and secondary FITCH conjugated rabbit anti mouse serum was added for half an hour, and the monolayers were washed and mounted. Several of the antibodies reacted strongly with the EBs in the inclusions (FIG. 9). In spite of the formaldehyde fixation it could not be excluded that the surface of the EB was changed by the treatments, so that the antibodies could get access to the Omp4-7 (SEQ ID NOs:2, 4, 6, 8). Therefore, the reaction was confirmed by immuno-electron microscopy with the antibody raised against clone pEX3-36. Purified EB of *C. pneumoniae* were absorbed to carbon coated nickel grids. After the absorption the grids were washed with PBS and blocked in 0.5% Ovalbumin dissolved in PBS. The antibodies were diluted 1:100 in the same buffer and incubated for 30 minutes. The grids were washed in PBS. Rabbit anti mouse Ig conjugated with 10 nm colloidal gold diluted in PBS containing 1% gelatin was added to the grids for half an hour. The grids were washed in 3×PBS with 1% gelatin and 3 times in PBS, the grids were contrastained with 0.7% phospho tungstic acid. The grids were analysed in a Jeol 1010 electron microscope at 40 kV. It was seen that the gold particles were covering the surface of the purified EB. Because the *C. pneumoniae* EBs were not exposed to any detergent or fixation under either the purification or the reaction with antibodies, these results show that the cloned proteins have surface exposed epitopes.

Polyclonal monospecific antibodies against Omp4 (SEQ ID NO:2)

The Omp4 gene (SEQ ID NO:1) was amplified by PCR with primers that contained LIC-sites, and the PCR product was cloned into the pET-30 LIC vector (Novagen). The histidine tagged fusion protein was expressed by induction of the synthesis by IPTG (isopropyl-beta-D-thiogalacto pvranoside) and purified over a nickel column. The purified Omp4 protein (SEQ ID NO:2) was used for immunization of a rabbit (six times, 8 µg each time).

Use of rabbit polyclonal antibodies to recombinant Omp4 for detection of *Chlamydia pneumoniae* in paraffin embedded sections The lungs of *C. pneumoniae* infected mice were obtained three days after intranasal infection. The tissue samples were fixed in 4% formaldehyde, paraffin embedded, sectioned and deparaffinized prior to staining. The sections were incubated with the rabbit serum diluted 1:200 in TBS (150 mM NaCl, 20 mM Tris pH 7.5) for 30 min at room temperature. After wash two times in TBS the sections were incubated with the secondary antibody (biotinylated goat anti-rabbit antibodies) diluted 1:300 in TBS, followed by two times wash in TBS. The sections were stained with streptavidin-biotin complex (streptABComplex/AP, Dako),for 30 min washed and developed under microscopic inspection with chromagen new fuchsin (Vector laboratories). The sections were counter stained with Hematoxylin and analyzed ny microscopy.

Immuno blotting analysis with hyperimmune monospecific rabbit anti-serum

The insert of pEX1-1 clone was amplified by PCR using primers containing LIC sites. The PCR product could therefore be inserted in the pET-32 LIC vector (Novagen, UK cat No. 69076-1). Thereby the insert sequence of the pEX1-1 clone was expressed in the new vector as a fusion protein, the part of the fusion protein encoded by the pET-32 LIC vector had 6 histidine residues in a row. The expression of the fusion protein was induced in this vector, and the fusion protein could be purified under denaturing condition on a Ni2+ column due to the high affinity of the histidine residues to divalent cations. The purified protein was used for immunization of a New Zealand white rabbit. After 6 times intramuscular and 2 times intravenous immunization the serum was obtained from the rabbit. Purified *C. pneumoniae* EB was dissolved in SDS-sample buffer. Half of the sample was heated to 100° C. in the sample buffer, whereas the other half of the sample was not heated. The samples were separated by SDS-PAGE, and the proteins were transferred to nitrocellulose, the serum was reacted with the strips. With the samples heated to 100° C. the serum recognized a high molecular weight band of approximately 98 kDa. This is in agreement with the predicted size of Omp5 (SEQ ID NO:4), of which the pEX1-1 clone is a part, however, when the antibody was reacted to the strip with unheated EB, the pattern was different. Now a band was seen with a size of 75 kDa, in addition weaker bands were observed above the band (FIG. 10). These data demonstrate that Omp5 (SEQ ID NO:4) needs boiling in SDS-sample buffer to be fully denatured and migrate with a size as predicted from the gene product. When the samples were not boiled, the protein was not fully denatured and less SDS binds to the protein and it has a more globular structure that will migrate faster in the acrylamide gel. The band pattern looked identical to what was obtained with a monoclonal antibody (MAb 26.1) (lane 6), we earlier have described (Christiansen et al., 1994), reacting with the surface of *C. pneumoniae* EB, but the antibody do not react with the fully SDS denatured *C. pneumoniae* EB in immunoblotting.

Experimental infection of C57 black mice

Due to the realization of the altered migration of the Omp4-7 proteins (SEQ ID NOs:2, 4, 6, 8) without boiling, we chose to analyse antibodies against *C. pneumoniae* EBs after an experimental infection of mice. To obtain antibodies from an infection caused by *C. pneumoniae*, C57 black mice were inoculated intranasally with 107 CFI of *C. pneumoniae* under a light ether anaesthesia. After 14 days of infection the serum samples were obtained and the lungs were analysed for pathological changes. In two of the mice a severe pneumonia was observed in the lung sections, and in the third mouse only minor changes were observed. The serum from the mice was diluted 1:100 and reacted with purified EBs dissolved in sample buffer with and without boiling. In the preparations that had been heated to 100° C. the sera from two of the mice reacted strongly with bands of 60/62 kDa and weaker bands of 55 kDa, but no reaction was observed with proteins of the size of Omp4-7 (SEQ ID NOs:2, 4, 6, 8) (FIG. 11). However, when the sera were reacted with the preparation that had not been heated they all had a strong reaction with a broad band of an approximate size of 75 kDa. This is in agreement with the size of the Omp4-7 proteins (SEQ ID NOs:2, 4, 6, 8) in the unheated preparation. Therefore, it could be concluded that the epitopes of the Omp4-7 proteins (SEQ ID NOs:2, 4, 6, 8) recognized by the antibodies after a *C. pneumoniae* infection were discontinuous epitopes because the full denaturation of the antigen completely destroyed the epitopes. The 75 kDa protein observed in unheated samples is not Omp2 (Shown in immunoblotting with an Omp2 specific antibody).

EXAMPLE 3

Comparison of Omp4-7 (SEQ ID NOs:2, 4, 6, 8) of *C. pneumoniae* with putative outer membrane proteins (POMP) of *C. psittaci*

Longbottom et al. (1996) have published partial sequence from 98 to 90 kDa proteins from *C. psittaci*. They have entered the full sequence of 5 genes in this family in the EMBL database. They have named the genes "putative outer membrane proteins" (POMP) since their precise location was not determined. The family is composed of two genes that are completely identical, and two genes with high homology to these genes. They calculated a molecular size of 90 and 91 kDa. The 5th encode a protein of 98 kDa. The sequence of the Omp4-7 proteins (SEQ ID NOs:2, 4, 6, 8) of *C. pneumoniae* were compared to the sequences of the *C. Psittaci* POMP proteins with the programme pileup in the GCG package. The amino acid homologies were in the range of 51-63%. It is seen that the *C. pneumoniae* Omp4-5 proteins (SEQ ID NOs:2, 4) are most related to the 98 kDa POMP protein of *C. psittaci*. Interestingly, the 98 kDa *C. psittaci* POMP protein is more related to the *C. pneumoniae* genes than to the other *C. psittaci* genes. The repeated sequences of GGAI (Gly-Gly-Ala-Ile, amino acids 164-167 of SEQ ID NO:2) were conserved in the 98 kDa POMP protein, but only three GGAI (Gly-Gly-Ala-Ile, amino acids 164-167 of SEQ ID NO:2) repeats were present in the 90 and 91 kDa *C. psittaci* POMP proteins. For *C.psittaci* it has been shown that antibodies to these proteins seem to be protective for the infection.

REFERENCES

1. Caldwell, H. D., J. Kromhout and J. Schachter, Infect. Immun. 31, 1161-1176 (1981).
2. Campbell, L. A., M. P. Melgosa, D. J. Hamilton, C.-C. Kuo and J. T. Grayston, J. Clinical Microbiol., 30, 434-439 (1992).
3. Christiansen, G., and S. Birkelund. Eur. Microbiol. 1:24-29 (1992).
4. Christiansen, G., L. Østergaard, and S. Birkelund. Proceedings of the eight International symposium on Human Infections, Eds. Orfila et al., pp 173-176, (1994).
5. Grayston, J. T., Kuo, C.-C., Campbell, L. A., and Vang, S.-P. Int. J. Syst. Bacteriol. 39, 88-90 (1989).
6. Grayston, J. T., C.-C. Kuo, S.-P. Wang and J. Altman. 1986. N. Engl. J. Med. 315, 161-168 (1986).
7. Kuo, C. C., L. A. Jackson, L. A. Campbell and J. T. Graystone. Clin. Microbiol. Rev. 8, 451-461 (1995)
8. Longbottom, D., M. Russell, G. E Jones, A. Lainson, and A.J. Herring. FEMS Microbiol. Lett. 142, 277-281 (1996).
9. Melgosa, M. P., C.-C. Kuo and L. A. Campbell, FEMS Microbiol. Lett. 112, 199-204 (1993).
10. Campbell, L. A., C.-C kuo, S. P. Wang amd J. T. Grayston. J. Clin. Microbiol. 28, 1261-1264 (1990).
11. Halme, S., P. Saikku and H.-M. Surcel. Scand. J. Immunol. 45, 378-384 (1997).
12. Miyashita, N. and A. Matsumoto. J. Clin. Microbiol. 30, 2911-2916 (1992).
13. Wang, S. P., and J.T. Grayston, Am. J. Ophtalmol. 70, 367-374 (1970).
14. Freund, E. A., H. Ernø and R. M. Lemcke. Identification of mycoplasma, P377-443 in I. Norris and J. R. Bergen; Methods in Microbiology vol 13, A. P. Inc. London 1979)

---

The invention claimed is:

1. An isolated *Chlamydia pneumoniae* protein free of any other chlamydial protein, wherein said isolated protein comprises the amino acid sequence as set forth in SEQ ID NO:2.

2. A composition comprising the protein of claim 1 and a pharmaceutically acceptable carrier.

3. A method of generating an immune response in a mammal comprising administering to the mammal an immunologically effective amount of the protein of claim 1.

4. A method of identifying a *Chlamydia pneumoniae* infection in a mammal, said method comprising:

(a) obtaining a sample comprising antibodies from the mammal, (b) contacting said sample with a diagnostic reagent, said reagent comprising the protein of claim 1 in labeled or immobilized form, (c) detecting binding of antibodies in the sample with the diagnostic reagent, and (d) correlating the presence of binding of said protein with antibodies in said sample with the presence of an infection.

* * * * *

SEQUENCE LISTING (1) GENERAL INFORMATION:

(iii) NUMBER OF SEQUENCES: 30

(2) INFORMATION FOR SEQ ID NO: 1:

(i) SEQUENCE CHARACTERISTICS:
      (A) LENGTH: 3200 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: Coding Sequence
      (B) LOCATION: 205...2988
      (D) OTHER INFORMATION:

(xi) SEQUENCE DESCRIPTION: SEQ ID NO: 1:

```
CAATGTCGAA GAGAGCACTA ACCAGGAAAA TTGCGATTTC ATAAACCCAC TTTATTATTA      60

AATTCTTACT TGCGTCATAT AAAATAGAAA ACTCAGAGAG TCAAGATAAA AATTCTTGAC     120

AGCTGTTTTG TCATCTTTAA CTTGATTTAC TTATTTTGTT TCTATATTGA TGCGAATAGT    180

TCTCTAAAAA ACAAAAGCAT TACC ATG AAG ACT TCG ATT CCT TGG GTT TTA       231
                         Met Lys Thr Ser Ile Pro Trp Val Leu
                           1               5

GTT TCC TCC GTG TTA GCT TTC TCA TGT CAC CTA CAG TCA CTA GCT AAC      279
Val Ser Ser Val Leu Ala Phe Ser Cys His Leu Gln Ser Leu Ala Asn
 10              15                  20                  25

GAG GAA CTT TTA TCA CCT GAT GAT AGC TTT AAT GGA AAT ATC GAT TCA      327
Glu Glu Leu Leu Ser Pro Asp Asp Ser Phe Asn Gly Asn Ile Asp Ser
                30                  35                  40

GGA ACG TTT ACT CCA AAA ACT TCA GCC ACA ACA TAT TCT CTA ACA GGA      375
Gly Thr Phe Thr Pro Lys Thr Ser Ala Thr Thr Tyr Ser Leu Thr Gly
            45                  50                  55

GAT GTC TTC TTT TAC GAG CCT GGA AAA GGC ACT CCC TTA TCT GAC AGT      423
Asp Val Phe Phe Tyr Glu Pro Gly Lys Gly Thr Pro Leu Ser Asp Ser
         60                  65                  70

TGT TTT AAG CAA ACC ACG GAC AAT CTT ACC TTC TTG GGG AAC GGT CAT      471
```

```
        Cys Phe Lys Gln Thr Thr Asp Asn Leu Thr Phe Leu Gly Asn Gly His
             75                  80                  85

AGC TTA ACG TTT GGC TTT ATA GAT GCT GGC ACT CAT GCA GGT GCT GCT        519
Ser Leu Thr Phe Gly Phe Ile Asp Ala Gly Thr His Ala Gly Ala Ala
 90                  95                 100                 105

GCA TCT ACA ACA GCA AAT AAG AAT CTT ACC TTC TCA GGG TTT TCC TTA        567
Ala Ser Thr Thr Ala Asn Lys Asn Leu Thr Phe Ser Gly Phe Ser Leu
                 110                 115                 120

CTG AGT TTT GAT TCC TCT CCT AGC ACA ACG GTT ACT ACA GGT CAG GGA        615
Leu Ser Phe Asp Ser Ser Pro Ser Thr Thr Val Thr Thr Gly Gln Gly
             125                 130                 135

ACG CTT TCC TCA GCA GGA GGC GTA AAT TTA GAA AAT ATT CGT AAA CTT        663
Thr Leu Ser Ser Ala Gly Gly Val Asn Leu Glu Asn Ile Arg Lys Leu
         140                 145                 150

GTA GTT GCT GGG AAT TTT TCT ACT GCA GAT GGT GGA GCT ATC AAA GGA        711
Val Val Ala Gly Asn Phe Ser Thr Ala Asp Gly Gly Ala Ile Lys Gly
     155                 160                 165

GCG TCT TTC CTT TTA ACT GGC ACT TCT GGA GAT GCT CTT TTT AGT AAC        759
Ala Ser Phe Leu Leu Thr Gly Thr Ser Gly Asp Ala Leu Phe Ser Asn
170                 175                 180                 185

AAC TCT TCA TCA ACA AAG GGA GGA GCA ATT GCT ACT ACA GCA GGC GCT        807
Asn Ser Ser Ser Thr Lys Gly Gly Ala Ile Ala Thr Thr Ala Gly Ala
                 190                 195                 200

CGC ATA GCA AAT AAC ACA GGT TAT GTT AGA TTC CTA TCT AAC ATA GCG        855
Arg Ile Ala Asn Asn Thr Gly Tyr Val Arg Phe Leu Ser Asn Ile Ala
             205                 210                 215

TCT ACG TCA GGA GGC GCT ATC GAT GAT GAA GGC ACG TCG ATA CTA TCG        903
Ser Thr Ser Gly Gly Ala Ile Asp Asp Glu Gly Thr Ser Ile Leu Ser
         220                 225                 230

AAC AAC AAA TTT CTA TAT TTT GAA GGG AAT GCA GCG AAA ACT ACT GGC        951
Asn Asn Lys Phe Leu Tyr Phe Glu Gly Asn Ala Ala Lys Thr Thr Gly
     235                 240                 245

GGT GCG ATC TGC AAC ACC AAG GCG AGT GGA TCT CCT GAA CTG ATA ATC        999
Gly Ala Ile Cys Asn Thr Lys Ala Ser Gly Ser Pro Glu Leu Ile Ile
250                 255                 260                 265

TCT AAC AAT AAG ACT CTG ATC TTT GCT TCA AAC GTA GCA GAA ACA AGC       1047
Ser Asn Asn Lys Thr Leu Ile Phe Ala Ser Asn Val Ala Glu Thr Ser
                 270                 275                 280

GGT GGC GCC ATC CAT GCT AAA AAG CTA GCC CTT TCC TCT GGA GGC TTT       1095
Gly Gly Ala Ile His Ala Lys Lys Leu Ala Leu Ser Ser Gly Gly Phe
             285                 290                 295

ACA GAG TTT CTA CGA AAT AAT GTC TCA TCA GCA ACT CCT AAG GGG GGT       1143
Thr Glu Phe Leu Arg Asn Asn Val Ser Ser Ala Thr Pro Lys Gly Gly
         300                 305                 310

GCT ATC AGC ATC GAT GCC TCA GGA GAG CTC AGT CTT TCT GCA GAG ACA       1191
Ala Ile Ser Ile Asp Ala Ser Gly Glu Leu Ser Leu Ser Ala Glu Thr
     315                 320                 325

GGA AAC ATT ACC TTT GTA AGA AAT ACC CTT ACA ACA ACC GGA AGT ACC       1239
Gly Asn Ile Thr Phe Val Arg Asn Thr Leu Thr Thr Thr Gly Ser Thr
330                 335                 340                 345

GAT ACT CCT AAA CGT AAT GCG ATC AAC ATA GGA AGT AAC GGG AAA TTC       1287
Asp Thr Pro Lys Arg Asn Ala Ile Asn Ile Gly Ser Asn Gly Lys Phe
                 350                 355                 360

ACG GAA TTA CGG GCT GCT AAA AAT CAT ACA ATT TTC TTC TAT GAT CCC       1335
Thr Glu Leu Arg Ala Ala Lys Asn His Thr Ile Phe Phe Tyr Asp Pro
             365                 370                 375

ATC ACT TCA GAA GGA ACC TCA TCA GAC GTA TTG AAG ATA AAT AAC GGC       1383
Ile Thr Ser Glu Gly Thr Ser Ser Asp Val Leu Lys Ile Asn Asn Gly
         380                 385                 390
```

```
TCT GCG GGA GCT CTC AAT CCA TAT CAA GGA ACG ATT CTA TTT TCT GGA      1431
Ser Ala Gly Ala Leu Asn Pro Tyr Gln Gly Thr Ile Leu Phe Ser Gly
    395                 400                 405

GAA ACC CTA ACA GCA GAT GAA CTT AAA GTT GCT GAC AAT TTA AAA TCT      1479
Glu Thr Leu Thr Ala Asp Glu Leu Lys Val Ala Asp Asn Leu Lys Ser
410                 415                 420                 425

TCA TTC ACG CAG CCA GTC TCC CTA TCC GGA GGA AAG TTA TTG CTA CAA      1527
Ser Phe Thr Gln Pro Val Ser Leu Ser Gly Gly Lys Leu Leu Leu Gln
                430                 435                 440

AAG GGA GTC ACT TTA GAG AGC ACG AGC TTC TCT CAA GAG GCC GGT TCT      1575
Lys Gly Val Thr Leu Glu Ser Thr Ser Phe Ser Gln Glu Ala Gly Ser
            445                 450                 455

CTC CTC GGC ATG GAT TCA GGA ACG ACA TTA TCA ACT ACA GCT GGG AGT      1623
Leu Leu Gly Met Asp Ser Gly Thr Thr Leu Ser Thr Thr Ala Gly Ser
        460                 465                 470

ATT ACA ATC ACG AAC CTA GGA ATC AAT GTT GAC TCC TTA GGT CTT AAG      1671
Ile Thr Ile Thr Asn Leu Gly Ile Asn Val Asp Ser Leu Gly Leu Lys
    475                 480                 485

CAG CCC GTC AGC CTA ACA GCA AAA GGT GCT TCA AAT AAA GTG ATC GTA      1719
Gln Pro Val Ser Leu Thr Ala Lys Gly Ala Ser Asn Lys Val Ile Val
490                 495                 500                 505

TCT GGG AAG CTC AAC CTG ATT GAT ATT GAA GGG AAC ATT TAT GAA AGT      1767
Ser Gly Lys Leu Asn Leu Ile Asp Ile Glu Gly Asn Ile Tyr Glu Ser
                510                 515                 520

CAT ATG TTC AGC CAT GAC CAG CTC TTC TCT CTA TTA AAA ATC ACG GTT      1815
His Met Phe Ser His Asp Gln Leu Phe Ser Leu Leu Lys Ile Thr Val
            525                 530                 535

GAT GCT GAT GTT GAT ACT AAC GTT GAC ATC AGC AGC CTT ATC CCT GTT      1863
Asp Ala Asp Val Asp Thr Asn Val Asp Ile Ser Ser Leu Ile Pro Val
        540                 545                 550

CCT GCT GAG GAT CCT AAT TCA GAA TAC GGA TTC CAA GGA CAA TGG AAT      1911
Pro Ala Glu Asp Pro Asn Ser Glu Tyr Gly Phe Gln Gly Gln Trp Asn
    555                 560                 565

GTT AAT TGG ACT ACG GAT ACA GCT ACA AAT ACA AAA GAG GCC ACG GCA      1959
Val Asn Trp Thr Thr Asp Thr Ala Thr Asn Thr Lys Glu Ala Thr Ala
570                 575                 580                 585

ACT TGG ACC AAA ACA GGA TTT GTT CCC AGC CCC GAA AGA AAA TCT GCG      2007
Thr Trp Thr Lys Thr Gly Phe Val Pro Ser Pro Glu Arg Lys Ser Ala
                590                 595                 600

TTA GTA TGC AAT ACC CTA TGG GGA GTC TTT ACT GAC ATT CGC TCT CTG      2055
Leu Val Cys Asn Thr Leu Trp Gly Val Phe Thr Asp Ile Arg Ser Leu
            605                 610                 615

CAA CAG CTT GTA GAG ATC GGC GCA ACT GGT ATG GAA CAC AAA CAA GGT      2103
Gln Gln Leu Val Glu Ile Gly Ala Thr Gly Met Glu His Lys Gln Gly
        620                 625                 630

TTC TGG GTT TCC TCC ATG ACG AAC TTC CTG CAT AAG ACT GGA GAT GAA      2151
Phe Trp Val Ser Ser Met Thr Asn Phe Leu His Lys Thr Gly Asp Glu
    635                 640                 645

AAT CGC AAA GGC TTC CGT CAT ACC TCT GGA GGC TAC GTC ATC GGT GGA      2199
Asn Arg Lys Gly Phe Arg His Thr Ser Gly Gly Tyr Val Ile Gly Gly
650                 655                 660                 665

AGT GCT CAC ACT CCT AAA GAC GAC CTA TTT ACC TTT GCG TTC TGC CAT      2247
Ser Ala His Thr Pro Lys Asp Asp Leu Phe Thr Phe Ala Phe Cys His
                670                 675                 680

CTC TTT GCT AGA GAC AAA GAT TGT TTT ATC GCT CAC AAC AAC TCT AGA      2295
Leu Phe Ala Arg Asp Lys Asp Cys Phe Ile Ala His Asn Asn Ser Arg
            685                 690                 695

ACC TAC GGT GGA ACT TTA TTC TTC AAG CAC TCT CAT ACC CTA CAA CCC      2343
Thr Tyr Gly Gly Thr Leu Phe Phe Lys His Ser His Thr Leu Gln Pro
        700                 705                 710
```

```
CAA AAC TAT TTG AGA TTA GGA AGA GCA AAG TTT TCT GAA TCA GCT ATA      2391
Gln Asn Tyr Leu Arg Leu Gly Arg Ala Lys Phe Ser Glu Ser Ala Ile
715                 720                 725

GAA AAA TTC CCT AGG GAA ATT CCC CTA GCC TTG GAT GTC CAA GTT TCG      2439
Glu Lys Phe Pro Arg Glu Ile Pro Leu Ala Leu Asp Val Gln Val Ser
730                 735                 740                 745

TTC AGC CAT TCA GAC AAC CGT ATG GAA ACG CAC TAT ACC TCA TTG CCA      2487
Phe Ser His Ser Asp Asn Arg Met Glu Thr His Tyr Thr Ser Leu Pro
                750                 755                 760

GAA TCC GAA GGT TCT TGG AGC AAC GAG TGT ATA GCT GGT GGT ATC GGC      2535
Glu Ser Glu Gly Ser Trp Ser Asn Glu Cys Ile Ala Gly Gly Ile Gly
            765                 770                 775

CTA GAC CTT CCT TTT GTT CTT TCC AAC CCA CAT CCT CTT TTC AAG ACC      2583
Leu Asp Leu Pro Phe Val Leu Ser Asn Pro His Pro Leu Phe Lys Thr
        780                 785                 790

TTC ATT CCA CAG ATG AAA GTC GAA ATG GTT TAT GTA TCA CAA AAT AGC      2631
Phe Ile Pro Gln Met Lys Val Glu Met Val Tyr Val Ser Gln Asn Ser
    795                 800                 805

TTC TTC GAA AGC TCT AGT GAT GGC CGT GGT TTT AGT ATT GGA AGG CTG      2679
Phe Phe Glu Ser Ser Ser Asp Gly Arg Gly Phe Ser Ile Gly Arg Leu
810                 815                 820                 825

CTT AAC CTC TCG ATT CCT GTG GGT GCG AAA TTC GTG CAG GGG GAT ATC      2727
Leu Asn Leu Ser Ile Pro Val Gly Ala Lys Phe Val Gln Gly Asp Ile
                830                 835                 840

GGA GAT TCC TAC ACC TAT GAT CTC TCA GGA TTC TTT GTT TCC GAT GTC      2775
Gly Asp Ser Tyr Thr Tyr Asp Leu Ser Gly Phe Phe Val Ser Asp Val
            845                 850                 855

TAT CGT AAC AAT CCC CAA TCT ACA GCG ACT CTT GTG ATG AGC CCA GAC      2823
Tyr Arg Asn Asn Pro Gln Ser Thr Ala Thr Leu Val Met Ser Pro Asp
        860                 865                 870

TCT TGG AAA ATT CGC GGT GGC AAT CTT TCA AGA CAG GCA TTT TTA CTG      2871
Ser Trp Lys Ile Arg Gly Gly Asn Leu Ser Arg Gln Ala Phe Leu Leu
    875                 880                 885

AGG GGT AGC AAC AAC TAC GTC TAC AAC TCC AAT TGT GAG CTC TTC GGA      2919
Arg Gly Ser Asn Asn Tyr Val Tyr Asn Ser Asn Cys Glu Leu Phe Gly
890                 895                 900                 905

CAT TAC GCT ATG GAA CTC CGT GGA TCT TCA AGG AAC TAC AAT GTA GAT      2967
His Tyr Ala Met Glu Leu Arg Gly Ser Ser Arg Asn Tyr Asn Val Asp
                910                 915                 920

GTT GGT ACC AAA CTC CGA TTC TAGATTGCTA AAACTCCCTA GTTCTTCTAG GGAG    3022
Val Gly Thr Lys Leu Arg Phe
            925

TTTTCTCATA CTTTTAGGGA AATATTTGCT ATAGGGAATG CTTTCCTTGC AAACTGTAAA    3082

AAATAACATT TGTCCCTCTT CAAAAAAGAT TTCTTTTAAT AATTTCTAGT TATAATTTTA    3142

TTTTAAAAAC AGTTAAATAA TTAATAGACA ATAATCTATT CTTATTGACT TCTTTTTT      3200
```

(2) INFORMATION FOR SEQ ID NO: 2:

(i) SEQUENCE CHARACTERISTICS:
        (A) LENGTH: 928 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO: 2:

Met Lys Thr Ser Ile Pro Trp Val Leu Val Ser Ser Val Leu Ala Phe

-continued

```
  1               5                   10                  15
Ser Cys His Leu Gln Ser Leu Ala Asn Glu Glu Leu Leu Ser Pro Asp
            20                  25                  30

Asp Ser Phe Asn Gly Asn Ile Asp Ser Gly Thr Phe Thr Pro Lys Thr
            35                  40                  45

Ser Ala Thr Thr Tyr Ser Leu Thr Gly Asp Val Phe Phe Tyr Glu Pro
 50                  55                  60

Gly Lys Gly Thr Pro Leu Ser Asp Ser Cys Phe Lys Gln Thr Thr Asp
 65                  70                  75                  80

Asn Leu Thr Phe Leu Gly Asn Gly His Ser Leu Thr Phe Gly Phe Ile
                85                  90                  95

Asp Ala Gly Thr His Ala Gly Ala Ala Ser Thr Thr Ala Asn Lys
                100                 105                 110

Asn Leu Thr Phe Ser Gly Phe Ser Leu Leu Ser Phe Asp Ser Ser Pro
                115                 120                 125

Ser Thr Thr Val Thr Thr Gly Gln Gly Thr Leu Ser Ser Ala Gly Gly
                130                 135                 140

Val Asn Leu Glu Asn Ile Arg Lys Leu Val Val Ala Gly Asn Phe Ser
145                 150                 155                 160

Thr Ala Asp Gly Gly Ala Ile Lys Gly Ala Ser Phe Leu Leu Thr Gly
                165                 170                 175

Thr Ser Gly Asp Ala Leu Phe Ser Asn Asn Ser Ser Thr Lys Gly
                180                 185                 190

Gly Ala Ile Ala Thr Thr Ala Gly Ala Arg Ile Ala Asn Asn Thr Gly
                195                 200                 205

Tyr Val Arg Phe Leu Ser Asn Ile Ala Ser Thr Ser Gly Gly Ala Ile
                210                 215                 220

Asp Asp Glu Gly Thr Ser Ile Leu Ser Asn Asn Lys Phe Leu Tyr Phe
225                 230                 235                 240

Glu Gly Asn Ala Ala Lys Thr Thr Gly Gly Ala Ile Cys Asn Thr Lys
                245                 250                 255

Ala Ser Gly Ser Pro Glu Leu Ile Ile Ser Asn Asn Lys Thr Leu Ile
                260                 265                 270

Phe Ala Ser Asn Val Ala Glu Thr Ser Gly Gly Ala Ile His Ala Lys
                275                 280                 285

Lys Leu Ala Leu Ser Ser Gly Phe Thr Glu Phe Leu Arg Asn Asn
                290                 295                 300

Val Ser Ser Ala Thr Pro Lys Gly Gly Ala Ile Ser Ile Asp Ala Ser
305                 310                 315                 320

Gly Glu Leu Ser Leu Ser Ala Glu Thr Gly Asn Ile Thr Phe Val Arg
                325                 330                 335

Asn Thr Leu Thr Thr Gly Ser Thr Asp Thr Pro Lys Arg Asn Ala
                340                 345                 350

Ile Asn Ile Gly Ser Asn Gly Lys Phe Thr Glu Leu Arg Ala Ala Lys
                355                 360                 365

Asn His Thr Ile Phe Phe Tyr Asp Pro Ile Thr Ser Glu Gly Thr Ser
                370                 375                 380

Ser Asp Val Leu Lys Ile Asn Asn Gly Ser Ala Gly Ala Leu Asn Pro
385                 390                 395                 400

Tyr Gln Gly Thr Ile Leu Phe Ser Gly Glu Thr Leu Thr Ala Asp Glu
                405                 410                 415

Leu Lys Val Ala Asp Asn Leu Lys Ser Ser Phe Thr Gln Pro Val Ser
                420                 425                 430
```

```
Leu Ser Gly Gly Lys Leu Leu Leu Gln Lys Gly Val Thr Leu Glu Ser
            435                 440                 445
Thr Ser Phe Ser Gln Glu Ala Gly Ser Leu Leu Gly Met Asp Ser Gly
        450                 455                 460
Thr Thr Leu Ser Thr Thr Ala Gly Ser Ile Thr Ile Thr Asn Leu Gly
465                 470                 475                 480
Ile Asn Val Asp Ser Leu Gly Leu Lys Gln Pro Val Ser Leu Thr Ala
                485                 490                 495
Lys Gly Ala Ser Asn Lys Val Ile Val Ser Gly Lys Leu Asn Leu Ile
            500                 505                 510
Asp Ile Glu Gly Asn Ile Tyr Glu Ser His Met Phe Ser His Asp Gln
        515                 520                 525
Leu Phe Ser Leu Leu Lys Ile Thr Val Asp Ala Asp Val Asp Thr Asn
        530                 535                 540
Val Asp Ile Ser Ser Leu Ile Pro Val Pro Ala Glu Asp Pro Asn Ser
545                 550                 555                 560
Glu Tyr Gly Phe Gln Gly Gln Trp Asn Val Asn Trp Thr Thr Asp Thr
                565                 570                 575
Ala Thr Asn Thr Lys Glu Ala Thr Ala Thr Trp Thr Lys Thr Gly Phe
            580                 585                 590
Val Pro Ser Pro Glu Arg Lys Ser Ala Leu Val Cys Asn Thr Leu Trp
        595                 600                 605
Gly Val Phe Thr Asp Ile Arg Ser Leu Gln Gln Leu Val Glu Ile Gly
        610                 615                 620
Ala Thr Gly Met Glu His Lys Gln Gly Phe Trp Val Ser Ser Met Thr
625                 630                 635                 640
Asn Phe Leu His Lys Thr Gly Asp Glu Asn Arg Lys Gly Phe Arg His
                645                 650                 655
Thr Ser Gly Gly Tyr Val Ile Gly Gly Ser Ala His Thr Pro Lys Asp
            660                 665                 670
Asp Leu Phe Thr Phe Ala Phe Cys His Leu Phe Ala Arg Asp Lys Asp
        675                 680                 685
Cys Phe Ile Ala His Asn Asn Ser Arg Thr Tyr Gly Gly Thr Leu Phe
        690                 695                 700
Phe Lys His Ser His Thr Leu Gln Pro Gln Asn Tyr Leu Arg Leu Gly
705                 710                 715                 720
Arg Ala Lys Phe Ser Glu Ser Ala Ile Glu Lys Phe Pro Arg Glu Ile
                725                 730                 735
Pro Leu Ala Leu Asp Val Gln Val Ser Phe Ser His Ser Asp Asn Arg
            740                 745                 750
Met Glu Thr His Tyr Thr Ser Leu Pro Glu Ser Glu Gly Ser Trp Ser
        755                 760                 765
Asn Glu Cys Ile Ala Gly Gly Ile Gly Leu Asp Leu Pro Phe Val Leu
        770                 775                 780
Ser Asn Pro His Pro Leu Phe Lys Thr Phe Ile Pro Gln Met Lys Val
785                 790                 795                 800
Glu Met Val Tyr Val Ser Gln Asn Ser Phe Glu Ser Ser Ser Asp
                805                 810                 815
Gly Arg Gly Phe Ser Ile Gly Arg Leu Leu Asn Leu Ser Ile Pro Val
            820                 825                 830
Gly Ala Lys Phe Val Gln Gly Asp Ile Gly Asp Ser Tyr Thr Tyr Asp
        835                 840                 845
```

| | | | | | | | | | | | | |
|---|---|---|---|---|---|---|---|---|---|---|---|---|
|Leu|Ser|Gly|Phe|Phe|Val|Ser|Asp|Val|Tyr|Arg|Asn|Asn Pro Gln Ser|
| | |850| | | |855| | | |860| | |

Thr Ala Thr Leu Val Met Ser Pro Asp Ser Trp Lys Ile Arg Gly Gly
865           870               875               880

Asn Leu Ser Arg Gln Ala Phe Leu Leu Arg Gly Ser Asn Asn Tyr Val
              885               890               895

Tyr Asn Ser Asn Cys Glu Leu Phe Gly His Tyr Ala Met Glu Leu Arg
              900           905           910

Gly Ser Ser Arg Asn Tyr Asn Val Asp Val Gly Thr Lys Leu Arg Phe
          915           920           925

(2) INFORMATION FOR SEQ ID NO: 3:

(i) SEQUENCE CHARACTERISTICS:
        (A) LENGTH: 2815 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 3:

```
ATGAAATCGC AATTTTCCTG GTTAGTGCTC TCTTCGACAT TGGCATGTTT TACTAGTTGT    60
TCCACTGTTT TTGCTGCAAC TGCTGAAAAT ATAGGCCCCT CTGATAGCTT TGACGGAAGT   120
ACTAACACAG GCACCTATAC TCCTAAAAAT ACGACTACTG AATAGACTA TACTCTGACA    180
GGAGATATAA CTCTGCAAAA CCTTGGGGAT TCGGCAGCTT TAACGAAGGG TTGTTTTTCT   240
GACACTACGG AATCTTTAAG CTTTGCCGGT AAGGGGTACT CACTTTCTTT TTTAAATATT   300
AAGTCTAGTG CTGAAGGCGC AGCACTTTCT GTTACAACTG ATAAAAATCT GTCGCTAACA   360
GGATTTTCGA GTCTTACTTT CTTAGCGGCC CCATCATCGG TAATCACAAC CCCCTCAGGA   420
AAAGGTGCAG TTAAATGTGG AGGGGATCTT ACATTTGATA ACAATGGAAC TATTTTATTT   480
AAACAAGATT ACTGTGAGGA AAATGGCGGA GCCATTTCTA CCAAGAATCT TTCTTTGAAA   540
AACAGCACGG GATCGATTTC TTTTGAAGGG AATAAATCGA GCGCAACAGG AAAAAAGGT    600
GGGGCTATTT GTGCTACTGG TACTGTAGAT ATTACAAATA ATACGGCTCC TACCCTCTTC   660
TCGAACAATA TTGCTGAAGC TGCAGGTGGA GCTATAAATA GCACAGGAAA CTGTACAATT   720
ACAGGGAATA CGTCTCTTGT ATTTTCTGAA AATAGTGTGA CAGCGACCGC AGGAAATGGA   780
GGAGCTCTTT CTGGAGATGC CGATGTTACC ATATCTGGGA ATCAGAGTGT AACTTTCTCA   840
GGAAACCAAG CTGTAGCTAA TGGCGGAGCC ATTTATGCTA AGAAGCTTAC ACTGGCTTCC   900
GGGGGGGGGG GGGGTATCTC CTTTTCTAAC AATATAGTCC AAGGTACCAC TGCAGGTAAT   960
GGTGGAGCCA TTTCTATACT GGCAGCTGGA GAGTGTAGTC TTTCAGCAGA AGCAGGGGAC  1020
ATTACCTTCA ATGGGAATGC CATTGTTGCA ACTACACCAC AAACTACAAA AGAAATTCT   1080
ATTGACATAG GATCTACTGC AAAGATCACG AATTTACGTG CAATATCTGG GCATAGCATC  1140
TTTTTCTACG ATCCGATTAC TGCTAATACG GCTGCGGATT CTACAGATAC TTTAAATCTC  1200
AATAAGGCTG ATGCAGGTAA TAGTACAGAT TATAGTGGGT CGATTGTTTT TTCTGGTGAA  1260
AAGCTCTCTG AAGATGAAGC AAAAGTTGCA GACAACCTCA CTTCTACGCT GAAGCAGCCT  1320
GTAACTCTAA CTGCAGGAAA TTTAGTACTT AAACGTGGTG TCACTCTCGA TACGAAAGGC  1380
TTTACTCAGA CCGCGGGTTC CTCTGTTATT ATGGATGCGG GCACAACGTT AAAAGCAAGT  1440
ACAGAGGAGG TCACTTTAAC AGGTCTTTCC ATTCCTGTAG ACTCTTTAGG CGAGGGTAAG  1500
AAAGTTGTAA TTGCTGCTTC TGCAGCAAGT AAAAAATGTAG CCCTTAGTGG TCCGATTCTT  1560
```

```
CTTTTGGATA ACCAAGGGAA TGCTTATGAA AATCACGACT TAGGAAAAAC TCAAGACTTT    1620

TCATTTGTGC AGCTCTCTGC TCTGGGTACT GCAACAACTA CAGATGTTCC AGCGGTTCCT    1680

ACAGTAGCAA CTCCTACGCA CTATGGGTAT CAAGGTACTT GGGAATGAC TTGGGTTGAT     1740

GATACCGCAA GCACTCCAAA GACTAAGACA GCGACATTAG CTTGGACCAA TACAGGCTAC    1800

CTTCCGAATC CTGAGCGTCA AGGACCTTTA GTTCCTAATA GCCTTTGGGG ATCTTTTTCA    1860

GACATCCAAG CGATTCAAGG TGTCATAGAG AGAAGTGCTT TGACTCTTTG TTCAGATCGA    1920

GGCTTCTGGG CTGCGGGAGT CGCCAATTTC TTAGATAAAG ATAAGAAAGG GGAAAAACGC    1980

AAATACCGTC ATAAATCTGG TGGATATGCT ATCGGAGGTG CAGCGCAAAC TTGTTCTGAA    2040

AACTTAATTA GCTTTGCCTT TGCCAACTC TTTGGTAGCG ATAAAGATTT CTTAGTCGCT     2100

AAAAATCATA CTGATACCTA TGCAGGAGCC TTCTATATCC AACACATTAC AGAATGTAGT    2160

GGGTTCATAG GTTGTCTCTT AGATAAACTT CCTGGCTCTT GGAGTCATAA ACCCCTCGTT    2220

TTAGAAGGGC AGCTCGCTTA TAGCCACGTC AGTAATGATC TGAAGACAAA GTATACTGCG    2280

TATCCTGAGG TGAAAGGTTC TTGGGGGAAT AATGCTTTTA ACATGATGTT GGGAGCTTCT    2340

TCTCATTCTT ATCCTGAATA CCTGCATTGT TTTGATACCT ATGCTCCATA CATCAAACTG    2400

AATCTGACCT ATATACGTCA GGACAGCTTC TCGGAGAAAG GTACAGAAGG AAGATCTTTT    2460

GATGACAGCA ACCTCTTCAA TTTATCTTTG CCTATAGGGG TGAAGTTTGA GAAGTTCTCT    2520

GATTGTAATG ACTTTTCTTA TGATCTGACT TTATCCTATG TTCCTGATCT TATCCGCAAT    2580

GATCCCAAAT GCACTACAGC ACTTGTAATC AGCGGAGCCT CTTGGGAAAC TTATGCCAAT    2640

AACTTAGCAC GACAGGCCTT GCAAGTGCGT GCAGGCAGTC ACTACGCCTT CTCTCCTATG    2700

TTTGAAGTGC TCGGCCAGTT TGTCTTTGAA GTTCGTGGAT CCTCACGGAT TTATAATGTA    2760

GATCTTGGGG GTAAGTTCCA ATTCTAGGAG CGTCTCTCAT GTCTCAGAAA TTCTG         2815
```

(2) INFORMATION FOR SEQ ID NO: 4:

(i) SEQUENCE CHARACTERISTICS:
        (A) LENGTH: 928 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 4:

```
Met Lys Ser Gln Phe Ser Trp Leu Val Leu Ser Ser Thr Leu Ala Cys
 1               5                  10                  15

Phe Thr Ser Cys Ser Thr Val Phe Ala Ala Thr Ala Glu Asn Ile Gly
            20                  25                  30

Pro Ser Asp Ser Phe Asp Gly Ser Thr Asn Thr Gly Thr Tyr Thr Pro
        35                  40                  45

Lys Asn Thr Thr Thr Gly Ile Asp Tyr Thr Leu Thr Gly Asp Ile Thr
    50                  55                  60

Leu Gln Asn Leu Gly Asp Ser Ala Ala Leu Thr Lys Gly Cys Phe Ser
65                  70                  75                  80

Asp Thr Thr Glu Ser Leu Ser Phe Ala Gly Lys Gly Tyr Ser Leu Ser
                85                  90                  95

Phe Leu Asn Ile Lys Ser Ser Ala Glu Gly Ala Ala Leu Ser Val Thr
            100                 105                 110

Thr Asp Lys Asn Leu Ser Leu Thr Gly Phe Ser Ser Leu Thr Phe Leu
        115                 120                 125
```

```
Ala Ala Pro Ser Ser Val Ile Thr Thr Pro Ser Gly Lys Gly Ala Val
    130                 135                 140

Lys Cys Gly Gly Asp Leu Thr Phe Asp Asn Asn Gly Thr Ile Leu Phe
145                 150                 155                 160

Lys Gln Asp Tyr Cys Glu Glu Asn Gly Gly Ala Ile Ser Thr Lys Asn
                165                 170                 175

Leu Ser Leu Lys Asn Ser Thr Gly Ser Ile Ser Phe Glu Gly Asn Lys
                180                 185                 190

Ser Ser Ala Thr Gly Lys Lys Gly Ala Ile Cys Ala Thr Gly Thr
            195                 200                 205

Val Asp Ile Thr Asn Asn Thr Ala Pro Thr Leu Phe Ser Asn Asn Ile
    210                 215                 220

Ala Glu Ala Ala Gly Gly Ala Ile Asn Ser Thr Gly Asn Cys Thr Ile
225                 230                 235                 240

Thr Gly Asn Thr Ser Leu Val Phe Ser Glu Asn Ser Val Thr Ala Thr
                245                 250                 255

Ala Gly Asn Gly Gly Ala Leu Ser Gly Asp Ala Asp Val Thr Ile Ser
            260                 265                 270

Gly Asn Gln Ser Val Thr Phe Ser Gly Asn Gln Ala Val Ala Asn Gly
            275                 280                 285

Gly Ala Ile Tyr Ala Lys Lys Leu Thr Leu Ala Ser Gly Gly Gly Gly
290                 295                 300

Gly Ile Ser Phe Ser Asn Asn Ile Val Gln Gly Thr Thr Ala Gly Asn
305                 310                 315                 320

Gly Gly Ala Ile Ser Ile Leu Ala Ala Gly Glu Cys Ser Leu Ser Ala
                325                 330                 335

Glu Ala Gly Asp Ile Thr Phe Asn Gly Asn Ala Ile Val Ala Thr Thr
                340                 345                 350

Pro Gln Thr Thr Lys Arg Asn Ser Ile Asp Ile Gly Ser Thr Ala Lys
            355                 360                 365

Ile Thr Asn Leu Arg Ala Ile Ser Gly His Ser Ile Phe Phe Tyr Asp
    370                 375                 380

Pro Ile Thr Ala Asn Thr Ala Ala Asp Ser Thr Asp Thr Leu Asn Leu
385                 390                 395                 400

Asn Lys Ala Asp Ala Gly Asn Ser Thr Asp Tyr Ser Gly Ser Ile Val
                405                 410                 415

Phe Ser Gly Glu Lys Leu Ser Glu Asp Glu Ala Lys Val Ala Asp Asn
                420                 425                 430

Leu Thr Ser Thr Leu Lys Gln Pro Val Thr Leu Thr Ala Gly Asn Leu
    435                 440                 445

Val Leu Lys Arg Gly Val Thr Leu Asp Thr Lys Gly Phe Thr Gln Thr
    450                 455                 460

Ala Gly Ser Ser Val Ile Met Asp Ala Gly Thr Thr Leu Lys Ala Ser
465                 470                 475                 480

Thr Glu Glu Val Thr Leu Thr Gly Leu Ser Ile Pro Val Asp Ser Leu
                485                 490                 495

Gly Glu Gly Lys Lys Val Val Ile Ala Ala Ser Ala Ala Ser Lys Asn
            500                 505                 510

Val Ala Leu Ser Gly Pro Ile Leu Leu Leu Asp Asn Gln Gly Asn Ala
    515                 520                 525

Tyr Glu Asn His Asp Leu Gly Lys Thr Gln Asp Phe Ser Phe Val Gln
    530                 535                 540
```

-continued

```
Leu Ser Ala Leu Gly Thr Ala Thr Thr Thr Asp Val Pro Ala Val Pro
545                 550                 555                 560

Thr Val Ala Thr Pro Thr His Tyr Gly Tyr Gln Gly Thr Trp Gly Met
                565                 570                 575

Thr Trp Val Asp Asp Thr Ala Ser Thr Pro Lys Thr Lys Thr Ala Thr
            580                 585                 590

Leu Ala Trp Thr Asn Thr Gly Tyr Leu Pro Asn Pro Glu Arg Gln Gly
        595                 600                 605

Pro Leu Val Pro Asn Ser Leu Trp Gly Ser Phe Ser Asp Ile Gln Ala
        610                 615                 620

Ile Gln Gly Val Ile Glu Arg Ser Ala Leu Thr Leu Cys Ser Asp Arg
625                 630                 635                 640

Gly Phe Trp Ala Ala Gly Val Ala Asn Phe Leu Asp Lys Asp Lys Lys
                645                 650                 655

Gly Glu Lys Arg Lys Tyr Arg His Lys Ser Gly Gly Tyr Ala Ile Gly
            660                 665                 670

Gly Ala Ala Gln Thr Cys Ser Glu Asn Leu Ile Ser Phe Ala Phe Cys
        675                 680                 685

Gln Leu Phe Gly Ser Asp Lys Asp Phe Leu Val Ala Lys Asn His Thr
        690                 695                 700

Asp Thr Tyr Ala Gly Ala Phe Tyr Ile Gln His Ile Thr Glu Cys Ser
705                 710                 715                 720

Gly Phe Ile Gly Cys Leu Leu Asp Lys Leu Pro Gly Ser Trp Ser His
                725                 730                 735

Lys Pro Leu Val Leu Glu Gly Gln Leu Ala Tyr Ser His Val Ser Asn
            740                 745                 750

Asp Leu Lys Thr Lys Tyr Thr Ala Tyr Pro Glu Val Lys Gly Ser Trp
        755                 760                 765

Gly Asn Asn Ala Phe Asn Met Met Leu Gly Ala Ser Ser His Ser Tyr
        770                 775                 780

Pro Glu Tyr Leu His Cys Phe Asp Thr Tyr Ala Pro Tyr Ile Lys Leu
785                 790                 795                 800

Asn Leu Thr Tyr Ile Arg Gln Asp Ser Phe Ser Glu Lys Gly Thr Glu
                805                 810                 815

Gly Arg Ser Phe Asp Asp Ser Asn Leu Phe Asn Leu Ser Leu Pro Ile
            820                 825                 830

Gly Val Lys Phe Glu Lys Phe Ser Asp Cys Asn Asp Phe Ser Tyr Asp
        835                 840                 845

Leu Thr Leu Ser Tyr Val Pro Asp Leu Ile Arg Asn Asp Pro Lys Cys
        850                 855                 860

Thr Thr Ala Leu Val Ile Ser Gly Ala Ser Trp Glu Thr Tyr Ala Asn
865                 870                 875                 880

Asn Leu Ala Arg Gln Ala Leu Gln Val Arg Ala Gly Ser His Tyr Ala
                885                 890                 895

Phe Ser Pro Met Phe Glu Val Leu Gly Gln Phe Val Phe Glu Val Arg
            900                 905                 910

Gly Ser Ser Arg Ile Tyr Asn Val Asp Leu Gly Gly Lys Phe Gln Phe
        915                 920                 925
```

(2) INFORMATION FOR SEQ ID NO: 5:

(i) SEQUENCE CHARACTERISTICS:
        (A) LENGTH: 3052 base pairs
        (B) TYPE: nucleic acid
        (C) STRANDEDNESS: single (D) TOPOLOGY: linear (ii) MOLECULE TYPE: Genomic DNA (xi) SEQUENCE DESCRIPTION: SEQ ID NO: 5:

```
ATGCGATTTT CGCTCTGCGG ATTTCCTCTA GTTTTTTCTT TAACATTGCT CTCAGTCTTC     60

GACACTTCTT TGAGTGCTAC TACGATTTCT TTAACCCCAG AAGATAGTTT TCATGGAGAT    120

AGTCAGAATG CAGAACGTTC TTATAATGTT CAAGCTGGGG ATGTCTATAG CCTTACTGGT    180

GATGTCTCAA TATCTAACGT CGATAACTCT GCATTAAATA AAGCCTGCTT CAATGTGACC    240

TCAGGAAGTG TGACGTTCGC AGGAAATCAT CATGGGTTAT ATTTTAATAA TATTTCCTCA    300

GGAACTACAA AGGAAGGGGC TGTACTTTGT TGCCAAGATC CTCAAGCAAC GGCACGTTTT    360

TCTGGGTTCT CCACGCTCTC TTTTATTCAG AGCCCCGGAG ATATTAAAGA ACAGGGATGT    420

CTCTATTCAA AAAATGCACT TATGCTCTTA ACAATTATG TAGTGCGTTT TGAACAAAAC     480

CAAAGTAAGA CTAAAGGCGG AGCTATTAGT GGGGCGAATG TTACTATAGT AGGCAACTAC    540

GATTCCGTCT CTTTCTATCA GAATGCAGCC ACTTTTGGAG GTGCTATCCA TTCTTCAGGT    600

CCCCTACAGA TTGCAGTAAA TCAGGCAGAG ATAAGATTTG CACAAAATAC TGCCAAGAAT    660

GGTTCTGGAG GGCTTTGTA CTCCGATGGT GATATTGATA TTGATCAGAA TGCTTATGTT     720

CTATTTCGAG AAAATGAGGC ATTGACTACT GCTATAGGTA AGGGAGGGGC TGTCTGTTGT    780

CTTCCCACTT CAGGAAGTAG TACTCCAGTT CCTATTGTGA CTTTCTCTGA CAATAAACAG    840

TTAGTCTTTG AAAGAAACCA TTCCATAATG GGTGGCGGAG CCATTTATGC TAGGAAACTT    900

AGCATCTCTT CAGGAGGTCC TACTCTATTT ATCAATAATA TATCATATGC AAATTCGCAA    960

AATTTAGGTG GAGCTATTGC CATTGATACT GGAGGGGAGA TCAGTTTATC AGCAGAGAAA   1020

GGAACAATTA CATTCCAAGG AAACCGGACG AGCTTACCGT TTTTGAATGG CATCCATCTT   1080

TTACAAAATG CTAAATTCCT GAAATTACAG GCGAGAAATG GATGCTCTAT AGAATTTTAT   1140

GATCCTATTA CTTCTGAAGC AGATGGGTCT ACCCAATTGA ATATCAACGG AGATCCTAAA   1200

AATAAAGAGT ACACAGGGAC CATACTCTTT TCTGGAGAAA AGAGTCTAGC AAACGATCCT   1260

AGGGATTTTA AATCTACAAT CCCTCAGAAC GTCAACCTGT CTGCAGGATA CTTAGTTATT   1320

AAAGAGGGGG CCGAAGTCAC AGTTTCAAAA TTCACGCAGT CTCCAGGATC GCATTTAGTT   1380

TTAGATTTAG GAACCAAACT GATAGCCTCT AAGGAAGACA TTGCCATCAC AGGCCTCGCG   1440

ATAGATATAG ATAGCTTAAG CTCATCCTCA ACAGCAGCTG TTATTAAAGC AAACACCGCA   1500

AATAAACAGA TATCCGTGAC GGACTCTATA GAACTTATCT CGCCTACTGG CAATGCCTAT   1560

GAAGATCTCA GAATGAGAAA TTCACAGACG TTCCCTCTGC TCTCTTTAGA GCCTGGAGCC   1620

GGGGGTAGTG TGACTGTAAC TGCTGGAGAT TTCCTACCGG TAAGTCCCCA TTATGGTTTT   1680

CAAGGCAATT GGAAATTAGC TTGGACAGGA ACTGGAAACA AGTTGGAGA ATTCTTCTGG     1740

GATAAAATAA ATTATAAGCC TAGACCTGAA AAAGAAGGAA ATTTAGTTCC TAATATCTTG   1800

TGGGGGAATG CTGTAAATGT CAGATCCTTA ATGCAGGTTC AAGAGACCCA TGCATCGAGC   1860

TTACAGACAG ATCGAGGGCT GTGGATCGAT GGAATTGGGA ATTTCTTCCA TGTATCTGCC   1920

TCCGAAGACA ATATAAGGTA CCGTCATAAC AGCGGTGGAT ATGTTCTATC TGTAAATAAT   1980

GAGATCACAC CTAAGCACTA TACTTCGATG GCATTTTCCC AACTCTTTAG TAGAGACAAG   2040

GACTATGCGG TTTCCAACAA CGAATACAGA ATGTATTTAG GATCGTATCT CTATCAATAT   2100

ACAACCTCCC TAGGGAATAT TTTCCGTTAT GCTTCGCGTA ACCCTAATGT AAACGTCGGG   2160

ATTCTCTCAA GAAGGTTTCT TCAAAATCCT CTTATGATTT TTCATTTTTT GTGTGCTTAT   2220
```

-continued

```
GGTCATGCCA CCAATGATAT GAAAACAGAC TACGCAAATT TCCCTATGGT GAAAAACAGC    2280

TGGAGAAACA ATTGTTGGGC TATAGAGTGC GGAGGGAGCA TGCCTCTATT GGTATTTGAG    2340

AACGGAAGAC TTTTCCAAGG TGCCATCCCA TTTATGAAAC TACAATTAGT TTATGCTTAT    2400

CAGGGAGATT TCAAAGAGAC GACTGCAGAT GGCCGTAGAT TTAGTAATGG GAGTTTAACA    2460

TCGATTTCTG TACCTCTAGG CATACGCTTT GAGAAGCTGG CACTTTCTCA GGATGTACTC    2520

TATGACTTTA GTTCTCCTA TATTCCTGAT ATTTTCCGTA AGGATCCCTC ATGTGAAGCT     2580

GCTCTGGTGA TTAGCGGAGA CTCCTGGCTT GTTCCGGCAG CACACGTATC AAGACATGCT    2640

TTTGTAGGGA GTGGAACGGG TCGGTATCAC TTTAACGACT ATACTGAGCT CTTATGTCGA    2700

GGAAGTATAG AATGCCGCCC CCATGCTAGG AATTATAATA TAAACTGTGG AAGCAAATTT    2760

CGTTTTTAGA AGGTTTCCAT TGCCTGTGTG GTTCCGGATC TTAACTATAA ATCCTGGACT    2820

ATGGATCATA GGCATTGGGT TTCTCGAACT TGTGTGGAGA ATAACGACAT TTTATATGCA    2880

TAACGGAATA CTCGTATCAC CTCAGCCCCT AGAGACATTC TTTAGGGGTT CTTTATTTGT    2940

CTAAACTTCG TATTTTATCG AGAATCCTTT ACGTTCTTGG TTTGCTTGTC TCCGAGGAGT    3000

TCTCTAACGA ATCATAGGGA TTCCAGGGTT CTGTTCCTTG AGTCCTTTGG CA            3052
```

(2) INFORMATION FOR SEQ ID NO: 6:

(i) SEQUENCE CHARACTERISTICS:
        (A) LENGTH: 922 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 6:

```
Met Arg Phe Ser Leu Cys Gly Phe Pro Leu Val Phe Ser Leu Thr Leu
  1               5                  10                  15

Leu Ser Val Phe Asp Thr Ser Leu Ser Ala Thr Thr Ile Ser Leu Thr
             20                  25                  30

Pro Glu Asp Ser Phe His Gly Asp Ser Gln Asn Ala Glu Arg Ser Tyr
         35                  40                  45

Asn Val Gln Ala Gly Asp Val Tyr Ser Leu Thr Gly Asp Val Ser Ile
     50                  55                  60

Ser Asn Val Asp Asn Ser Ala Leu Asn Lys Ala Cys Phe Asn Val Thr
 65                  70                  75                  80

Ser Gly Ser Val Thr Phe Ala Gly Asn His His Gly Leu Tyr Phe Asn
                 85                  90                  95

Asn Ile Ser Ser Gly Thr Thr Lys Glu Gly Ala Val Leu Cys Cys Gln
            100                 105                 110

Asp Pro Gln Ala Thr Ala Arg Phe Ser Gly Phe Ser Thr Leu Ser Phe
        115                 120                 125

Ile Gln Ser Pro Gly Asp Ile Lys Glu Gln Gly Cys Leu Tyr Ser Lys
    130                 135                 140

Asn Ala Leu Met Leu Leu Asn Asn Tyr Val Val Arg Phe Glu Gln Asn
145                 150                 155                 160

Gln Ser Lys Thr Lys Gly Gly Ala Ile Ser Gly Ala Asn Val Thr Ile
                165                 170                 175

Val Gly Asn Tyr Asp Ser Val Ser Phe Tyr Gln Asn Ala Ala Thr Phe
            180                 185                 190

Gly Gly Ala Ile His Ser Ser Gly Pro Leu Gln Ile Ala Val Asn Gln
```

-continued

```
            195                 200                 205
Ala Glu Ile Arg Phe Ala Gln Asn Thr Ala Lys Asn Gly Ser Gly Gly
            210                 215                 220

Ala Leu Tyr Ser Asp Gly Asp Ile Asp Ile Asp Gln Asn Ala Tyr Val
225                 230                 235                 240

Leu Phe Arg Glu Asn Glu Ala Leu Thr Thr Ala Ile Gly Lys Gly Gly
                245                 250                 255

Ala Val Cys Cys Leu Pro Thr Ser Gly Ser Ser Thr Pro Val Pro Ile
            260                 265                 270

Val Thr Phe Ser Asp Asn Lys Gln Leu Val Phe Glu Arg Asn His Ser
            275                 280                 285

Ile Met Gly Gly Gly Ala Ile Tyr Ala Arg Lys Leu Ser Ile Ser Ser
            290                 295                 300

Gly Gly Pro Thr Leu Phe Ile Asn Asn Ile Ser Tyr Ala Asn Ser Gln
305                 310                 315                 320

Asn Leu Gly Gly Ala Ile Ala Ile Asp Thr Gly Gly Glu Ile Ser Leu
                325                 330                 335

Ser Ala Glu Lys Gly Thr Ile Thr Phe Gln Gly Asn Arg Thr Ser Leu
            340                 345                 350

Pro Phe Leu Asn Gly Ile His Leu Leu Gln Asn Ala Lys Phe Leu Lys
            355                 360                 365

Leu Gln Ala Arg Asn Gly Cys Ser Ile Glu Phe Tyr Asp Pro Ile Thr
370                 375                 380

Ser Glu Ala Asp Gly Ser Thr Gln Leu Asn Ile Asn Gly Asp Pro Lys
385                 390                 395                 400

Asn Lys Glu Tyr Thr Gly Thr Ile Leu Phe Ser Gly Glu Lys Ser Leu
                405                 410                 415

Ala Asn Asp Pro Arg Asp Phe Lys Ser Thr Ile Pro Gln Asn Val Asn
            420                 425                 430

Leu Ser Ala Gly Tyr Leu Val Ile Lys Glu Gly Ala Glu Val Thr Val
            435                 440                 445

Ser Lys Phe Thr Gln Ser Pro Gly Ser His Leu Val Leu Asp Leu Gly
            450                 455                 460

Thr Lys Leu Ile Ala Ser Lys Glu Asp Ile Ala Ile Thr Gly Leu Ala
465                 470                 475                 480

Ile Asp Ile Asp Ser Leu Ser Ser Ser Thr Ala Ala Val Ile Lys
                485                 490                 495

Ala Asn Thr Ala Asn Lys Gln Ile Ser Val Thr Asp Ser Ile Glu Leu
            500                 505                 510

Ile Ser Pro Thr Gly Asn Ala Tyr Glu Asp Leu Arg Met Arg Asn Ser
            515                 520                 525

Gln Thr Phe Pro Leu Leu Ser Leu Glu Pro Gly Ala Gly Gly Ser Val
            530                 535                 540

Thr Val Thr Ala Gly Asp Phe Leu Pro Val Ser Pro His Tyr Gly Phe
545                 550                 555                 560

Gln Gly Asn Trp Lys Leu Ala Trp Thr Gly Thr Gly Asn Lys Val Gly
                565                 570                 575

Glu Phe Phe Trp Asp Lys Ile Asn Tyr Lys Pro Arg Pro Glu Lys Glu
            580                 585                 590

Gly Asn Leu Val Pro Asn Ile Leu Trp Gly Asn Ala Val Asn Val Arg
            595                 600                 605

Ser Leu Met Gln Val Gln Glu Thr His Ala Ser Ser Leu Gln Thr Asp
610                 615                 620
```

```
Arg Gly Leu Trp Ile Asp Gly Ile Gly Asn Phe Phe His Val Ser Ala
625                 630                 635                 640

Ser Glu Asp Asn Ile Arg Tyr Arg His Asn Ser Gly Gly Tyr Val Leu
            645                 650                 655

Ser Val Asn Asn Glu Ile Thr Pro Lys His Tyr Thr Ser Met Ala Phe
            660                 665                 670

Ser Gln Leu Phe Ser Arg Asp Lys Asp Tyr Ala Val Ser Asn Asn Glu
            675                 680                 685

Tyr Arg Met Tyr Leu Gly Ser Tyr Leu Tyr Gln Tyr Thr Thr Ser Leu
690                 695                 700

Gly Asn Ile Phe Arg Tyr Ala Ser Arg Asn Pro Asn Val Asn Val Gly
705                 710                 715                 720

Ile Leu Ser Arg Arg Phe Leu Gln Asn Pro Leu Met Ile Phe His Phe
                725                 730                 735

Leu Cys Ala Tyr Gly His Ala Thr Asn Asp Met Lys Thr Asp Tyr Ala
                740                 745                 750

Asn Phe Pro Met Val Lys Asn Ser Trp Arg Asn Asn Cys Trp Ala Ile
            755                 760                 765

Glu Cys Gly Gly Ser Met Pro Leu Leu Val Phe Glu Asn Gly Arg Leu
770                 775                 780

Phe Gln Gly Ala Ile Pro Phe Met Lys Leu Gln Leu Val Tyr Ala Tyr
785                 790                 795                 800

Gln Gly Asp Phe Lys Glu Thr Thr Ala Asp Gly Arg Arg Phe Ser Asn
                805                 810                 815

Gly Ser Leu Thr Ser Ile Ser Val Pro Leu Gly Ile Arg Phe Glu Lys
            820                 825                 830

Leu Ala Leu Ser Gln Asp Val Leu Tyr Asp Phe Ser Phe Ser Tyr Ile
            835                 840                 845

Pro Asp Ile Phe Arg Lys Asp Pro Ser Cys Glu Ala Ala Leu Val Ile
850                 855                 860

Ser Gly Asp Ser Trp Leu Val Pro Ala Ala His Val Ser Arg His Ala
865                 870                 875                 880

Phe Val Gly Ser Gly Thr Gly Arg Tyr His Phe Asn Asp Tyr Thr Glu
                885                 890                 895

Leu Leu Cys Arg Gly Ser Ile Glu Cys Arg Pro His Ala Arg Asn Tyr
            900                 905                 910

Asn Ile Asn Cys Gly Ser Lys Phe Arg Phe
            915                 920
```

(2) INFORMATION FOR SEQ ID NO: 7:

(i) SEQUENCE CHARACTERISTICS:
        (A) LENGTH: 2526 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 7:

```
ATGAAGATTC CACTCCGCTT TTTATTGATA TCATTAGTAC CTACGCTTTC TATGTCGAAT      60

TTATTAGGAG CTGCTACTAC CGAAGAGCTA TCGGCTAGCA ATAGCTTCGA TGGAACTACA     120

TCAACAACAA GCTTTTCTAG TAAAACATCA TCGGCTACAG ATGGCACCAA TTATGTTTTT     180

AAAGATTCTG TAGTTATAGA AAATGTACCC AAAACAGGGG AAACTCAGTC TACTAGTTGT     240
```

-continued

| | |
|---|---|
| TTTAAAAATG ACGCTGCAGC TGGAGATCTA AATTTCTTAG GAGGGGGATT TTCTTTCACA | 300 |
| TTTAGCAATA TCGATGCAAC CACGGCTTCT GGAGCTGCTA TTGGAAGTGA AGCAGCTAAT | 360 |
| AAGACAGTCA CGTTATCAGG ATTTTCGGCA CTTTCTTTTC TTAAATCCCC AGCAAGTACA | 420 |
| GTGACTAATG GATTGGGAGC TATCAATGTT AAAGGGAATT TAAGCCTATT GGATAATGAT | 480 |
| AAGGTATTGA TTCAGGACAA TTTCTCAACA GGAGATGGCG GAGCAATTAA TTGTGCAGGC | 540 |
| TCCTTGAAGA TCGCAAACAA TAAGTCCCTT TCTTTTATTG GAAATAGTTC TTCAACACGT | 600 |
| GGCGGAGCGA TTCATACCAA AAACCTCACA CTATCTTCTG GTGGGGAAAC TCTATTTCAG | 660 |
| GGGAATACAG CGCCTACGGC TGCTGGTAAA GGAGGTGCTA TCGCGATTGC AGACTCTGGC | 720 |
| ACCCTATCCA TTTCTGGAGA CAGTGGCGAC ATTATCTTTG AAGGCAATAC GATAGGAGCT | 780 |
| ACAGGAACCG TCTCTCATAG TGCTATTGAT TTAGGAACTA GCGCTAAGAT AACTGCGTTA | 840 |
| CGTGCTGCGC AAGGACATAC GATATACTTT TATGATCCGA TTACTGTAAC AGGATCGACA | 900 |
| TCTGTTGCTG ATGCTCTCAA TATTAATAGC CCTGATACTG GAGATAACAA AGAGTATACG | 960 |
| GGAACCATAG TCTTTTCTGG AGAGAAGCTC ACGGAGGCAG AAGCTAAAGA TGAGAAGAAC | 1020 |
| CGCACTTCTA AATTACTTCA AAATGTTGCT TTTAAAAATG GGACTGTAGT TTTAAAAGGT | 1080 |
| GATGTCGTTT TAAGTGCGAA CGGTTTCTCT CAGGATGCAA ACTCTAAGTT GATTATGGAT | 1140 |
| TTAGGGACGT CGTTGGTTGC AAACACCGAA AGTATCGAGT TAACGAATTT GGAAATTAAT | 1200 |
| ATAGACTCTC TCAGGAACGG GAAAAAGATA AAACTCAGTG CTGCCACAGC TCAGAAAGAT | 1260 |
| ATTCGTATAG ATCGTCCTGT TGTACTGGCA ATTAGCGATG AGAGTTTTTA TCAAAATGGC | 1320 |
| TTTTTGAATG AGGACCATTC CTATGATGGG ATTCTTGAGT TAGATGCTGG GAAAGACATC | 1380 |
| GTGATTTCTG CAGATTCTCG CAGTATAAAT GCTGTACAAT CTCCGTATGG CTATCAGGGA | 1440 |
| AAGTGGACAA TCAATTGGTC TACTGATGAT AAGAAAGCTA CGGTTTCTTG GGCAAAGCAA | 1500 |
| AGTTTTAATC CCACTGCTGA GCAGGAGGCT CCGTTAGTTC CTAATCTTCT TTGGGGTTCT | 1560 |
| TTTATAGATG TTCGTCCCTT CCAAAATTTT ATAGAGCTAG GTACTGAAGG TGCTCCTTAC | 1620 |
| GAAAAGAGAT TTTGGGTTGC AGGCATTTCC AATGTTTTGC ATAGGAGCGG TCGTGAAAAT | 1680 |
| CAAAGGAAAT TCCGTCATGT GAGTGGAGGT GCTGTAGTAG GTGCTAGCAC GAGGATGCCG | 1740 |
| GGTGGTGATA CCTTGTCTCT GGGTTTTGCT CAGCTCTTTG CGCGTGACAA AGACTACTTT | 1800 |
| ATGAATACCA ATTTCGCAAA GACCTACGCA GGATCTTTAC GTTTGCAGCA CGATGCTTCC | 1860 |
| CTATACTCTG TGGTGAGTAT CCTTTTAGGA GAGGGAGGAC TCCGCGAGAT CCTGTTGCCT | 1920 |
| TATGTTTCCA AGACTCTGCC GTGCTCTTTC TATGGGCAGC TTAGCTACGG CCATACGGAT | 1980 |
| CATCGCATGA AGACCGAGTC TCTACCCCCC CCCCCCCGA CGCTCTCGAC GGATCATACT | 2040 |
| TCTTGGGGAG GATATGTCTG GGCTGGAGAG CTGGAACTC GAGTTGCTGT TGAAAATACC | 2100 |
| AGCGGCAGAG GATTTTTCCG AGAGTACACT CCATTTGTAA AAGTCCAAGC TGTTTACTCG | 2160 |
| CGCCAAGATA GCTTTGTTGA ACTAGGAGCT ATCAGTCGTG ATTTTAGTGA TTCGCATCTT | 2220 |
| TATAACCTTG CGATTCCTCT TGGAATCAAG TTAGAGAAAC GGTTTGCAGA GCAATATTAT | 2280 |
| CATGTTGTAG CGATGTATTC TCCAGATGTT TGTCGTAGTA ACCCCAAATG TACGACTACC | 2340 |
| CTACTTTCCA ACCAAGGGAG TTGGAAGACC AAAGGTTCGA ACTTAGCAAG ACAGGCTGGT | 2400 |
| ATTGTTCAGG CCTCAGGTTT TCGATCTTTG GGAGCTGCAG CAGAGCTTTT CGGGAACTTT | 2460 |
| GGCTTTGAAT GGCGGGGATC TTCTCGTAGC TATAATGTAG ATGCGGGTAG CAAAATCAAA | 2520 |
| TTTTAG | 2526 |

(2) INFORMATION FOR SEQ ID NO: 8:

(i) SEQUENCE CHARACTERISTICS:
  (A) LENGTH: 841 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO: 8:

```
Met Lys Ile Pro Leu Arg Phe Leu Leu Ile Ser Leu Val Pro Thr Leu
 1               5                  10                  15

Ser Met Ser Asn Leu Leu Gly Ala Ala Thr Thr Glu Glu Leu Ser Ala
             20                  25                  30

Ser Asn Ser Phe Asp Gly Thr Thr Ser Thr Thr Ser Phe Ser Ser Lys
         35                  40                  45

Thr Ser Ser Ala Thr Asp Gly Thr Asn Tyr Val Phe Lys Asp Ser Val
     50                  55                  60

Val Ile Glu Asn Val Pro Lys Thr Gly Glu Thr Gln Ser Thr Ser Cys
 65                  70                  75                  80

Phe Lys Asn Asp Ala Ala Ala Gly Asp Leu Asn Phe Leu Gly Gly Gly
                 85                  90                  95

Phe Ser Phe Thr Phe Ser Asn Ile Asp Ala Thr Thr Ala Ser Gly Ala
            100                 105                 110

Ala Ile Gly Ser Glu Ala Ala Asn Lys Thr Val Thr Leu Ser Gly Phe
        115                 120                 125

Ser Ala Leu Ser Phe Leu Lys Ser Pro Ala Ser Thr Val Thr Asn Gly
    130                 135                 140

Leu Gly Ala Ile Asn Val Lys Gly Asn Leu Ser Leu Leu Asp Asn Asp
145                 150                 155                 160

Lys Val Leu Ile Gln Asp Asn Phe Ser Thr Gly Asp Gly Gly Ala Ile
                165                 170                 175

Asn Cys Ala Gly Ser Leu Lys Ile Ala Asn Asn Lys Ser Leu Ser Phe
            180                 185                 190

Ile Gly Asn Ser Ser Ser Thr Arg Gly Gly Ala Ile His Thr Lys Asn
        195                 200                 205

Leu Thr Leu Ser Ser Gly Gly Glu Thr Leu Phe Gln Gly Asn Thr Ala
    210                 215                 220

Pro Thr Ala Ala Gly Lys Gly Gly Ala Ile Ala Ile Ala Asp Ser Gly
225                 230                 235                 240

Thr Leu Ser Ile Ser Gly Asp Ser Gly Asp Ile Ile Phe Glu Gly Asn
                245                 250                 255

Thr Ile Gly Ala Thr Gly Thr Val Ser His Ser Ala Ile Asp Leu Gly
            260                 265                 270

Thr Ser Ala Lys Ile Thr Ala Leu Arg Ala Ala Gln Gly His Thr Ile
        275                 280                 285

Tyr Phe Tyr Asp Pro Ile Thr Val Thr Gly Ser Thr Ser Val Ala Asp
    290                 295                 300

Ala Leu Asn Ile Asn Ser Pro Asp Thr Gly Asp Asn Lys Glu Tyr Thr
305                 310                 315                 320

Gly Thr Ile Val Phe Ser Gly Glu Lys Leu Thr Glu Ala Glu Ala Lys
                325                 330                 335

Asp Glu Lys Asn Arg Thr Ser Lys Leu Leu Gln Asn Val Ala Phe Lys
            340                 345                 350

Asn Gly Thr Val Val Leu Lys Gly Asp Val Val Leu Ser Ala Asn Gly
```

-continued

```
               355                 360                 365
Phe Ser Gln Asp Ala Asn Ser Lys Leu Ile Met Asp Leu Gly Thr Ser
    370                 375                 380
Leu Val Ala Asn Thr Glu Ser Ile Glu Leu Thr Asn Leu Glu Ile Asn
385                 390                 395                 400
Ile Asp Ser Leu Arg Asn Gly Lys Lys Ile Lys Leu Ser Ala Ala Thr
                405                 410                 415
Ala Gln Lys Asp Ile Arg Ile Asp Arg Pro Val Val Leu Ala Ile Ser
                420                 425                 430
Asp Glu Ser Phe Tyr Gln Asn Gly Phe Leu Asn Glu Asp His Ser Tyr
                435                 440                 445
Asp Gly Ile Leu Glu Leu Asp Ala Gly Lys Asp Ile Val Ile Ser Ala
            450                 455                 460
Asp Ser Arg Ser Ile Asn Ala Val Gln Ser Pro Tyr Gly Tyr Gln Gly
465                 470                 475                 480
Lys Trp Thr Ile Asn Trp Ser Thr Asp Lys Lys Ala Thr Val Ser
                    485                 490                 495
Trp Ala Lys Gln Ser Phe Asn Pro Thr Ala Glu Gln Glu Ala Pro Leu
            500                 505                 510
Val Pro Asn Leu Leu Trp Gly Ser Phe Ile Asp Val Arg Pro Phe Gln
            515                 520                 525
Asn Phe Ile Glu Leu Gly Thr Glu Gly Ala Pro Tyr Glu Lys Arg Phe
        530                 535                 540
Trp Val Ala Gly Ile Ser Asn Val Leu His Arg Ser Gly Arg Glu Asn
545                 550                 555                 560
Gln Arg Lys Phe Arg His Val Ser Gly Gly Ala Val Val Gly Ala Ser
                565                 570                 575
Thr Arg Met Pro Gly Asp Thr Leu Ser Leu Gly Phe Ala Gln Leu
                580                 585                 590
Phe Ala Arg Asp Lys Asp Tyr Phe Met Asn Thr Asn Phe Ala Lys Thr
            595                 600                 605
Tyr Ala Gly Ser Leu Arg Leu Gln His Asp Ala Ser Leu Tyr Ser Val
    610                 615                 620
Val Ser Ile Leu Leu Gly Glu Gly Gly Leu Arg Glu Ile Leu Leu Pro
625                 630                 635                 640
Tyr Val Ser Lys Thr Leu Pro Cys Ser Phe Tyr Gly Gln Leu Ser Tyr
                645                 650                 655
Gly His Thr Asp His Arg Met Lys Thr Glu Ser Leu Pro Pro Pro
                660                 665                 670
Pro Thr Leu Ser Thr Asp His Thr Ser Trp Gly Gly Tyr Val Trp Ala
                675                 680                 685
Gly Glu Leu Gly Thr Arg Val Ala Val Glu Asn Thr Ser Gly Arg Gly
    690                 695                 700
Phe Phe Arg Glu Tyr Thr Pro Phe Val Lys Val Gln Ala Val Tyr Ser
705                 710                 715                 720
Arg Gln Asp Ser Phe Val Glu Leu Gly Ala Ile Ser Arg Asp Phe Ser
                725                 730                 735
Asp Ser His Leu Tyr Asn Leu Ala Ile Pro Leu Gly Ile Lys Leu Glu
            740                 745                 750
Lys Arg Phe Ala Glu Gln Tyr Tyr His Val Val Ala Met Tyr Ser Pro
            755                 760                 765
Asp Val Cys Arg Ser Asn Pro Lys Cys Thr Thr Thr Leu Leu Ser Asn
770                 775                 780
```

```
Gln Gly Ser Trp Lys Thr Lys Gly Ser Asn Leu Ala Arg Gln Ala Gly
785                 790                 795                 800

Ile Val Gln Ala Ser Gly Phe Arg Ser Leu Gly Ala Ala Ala Glu Leu
                805                 810                 815

Phe Gly Asn Phe Gly Phe Glu Trp Arg Gly Ser Ser Arg Ser Tyr Asn
                820                 825                 830

Val Asp Ala Gly Ser Lys Ile Lys Phe
            835                 840

(2) INFORMATION FOR SEQ ID NO: 9:

(i) SEQUENCE CHARACTERISTICS:
        (A) LENGTH: 2787 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 9:

ATGAAGTCTT CTTTCCCCAA GTTTGTATTT TCTACATTTG CTATTTTCCC TTTGTCTATG      60

ATTGCTACCG AGACAGTTTT GGATTCAAGT GCGAGTTTCG ATGGGAATAA AAATGGTAAT     120

TTTTCAGTTC GTGAGAGTCA GGAAGATGCT GGAACTACCT ACCTATTTAA GGGAAATGTC     180

ACTCTAGAAA ATATTCCTGG AACAGGCACA GCAATCACAA AAAGCTGTTT TAACAACACT     240

AAGGGCGATT TGACTTTCAC AGGTAACGGG AACTCTCTAT TGTTCCAAAC GGTGGATGCA     300

GGGACTGTAG CAGGGGCTGC TGTTAACAGC AGCGTGGTAG ATAAATCTAC CACGTTTATA     360

GGGTTTTCTT CGCTATCTTT TATTGCGTCT CCTGGAAGTT CGATAACTAC CGGCAAAGGA     420

GCCGTTAGCT GCTCTACGGG TAGCTTGAAG TTTGACAAAA ATGTCAGTTT GCTCTTCAGC     480

AAAAACTTTT CAACGGATAA TGGCGGTGCT ATCACCGCAA AAACTCTTTC ATTAACAGGG     540

ACTACAATGT CAGCTCTGTT TTCTGAAAAT ACCTCCTCAA AGAAAGGCGG AGCCATTCAG     600

ACTTCCGATG CCCTTACCAT TACTGGAAAC CAAGGGGAAG TCTCTTTTTC TGACAATACT     660

TCTTCGGATT CTGGAGCTGC AATTTTTACA GAAGCCTCGG TGACTATTTC TAATAATGCT     720

AAAGTTTCCT TTATTGACAA TAAGGTCACA GGAGCGAGCT CCTCAACAAC GGGGGATATG     780

TCAGGAGGTG CTATCTGTGC TTATAAAACT AGTACAGATA CTAAGGTCAC CCTCACTGGA     840

AATCAGATGT TACTCTTCAG CAACAATACA TCGACAACAG CGGGAGGAGC TATCTATGTG     900

AAAAAGCTCG AACTGGCTTC CGGAGGACTT ACCCTATTCA GTAGAAATAG TGTCAATGGA     960

GGTACAGCTC CTAAAGGTGG AGCCATAGCT ATCGAAGATA GTGGGGAATT GAGTTTATCC    1020

GCCGATAGTG GTGACATTGT CTTTTTAGGG AATACAGTCA CTTCTACTAC TCCTGGGACG    1080

AATAGAAGTA GTATCGACTT AGGAACGAGT GCAAAGATGA CAGCTTTGCG TTCTGCTGCT    1140

GGTAGAGCCA TCTACTTCTA TGATCCCATA ACTACAGGAT CTTCCACAAC AGTTACAGAT    1200

GTCTTAAAAG TTAATGAGAC TCCGGCAGAT TCTGCACTAC AATATACAGG GAACATCATC    1260

TTCACAGGAG AAAAGTTATC AGAGACAGAG GCCGCAGATT CTAAAAATCT TACTTCGAAG    1320

CTACTACAGC CTGTAACTCT TTCAGGAGGT ACTCTATCTT TAAAACATGG AGTGACTCTG    1380

CAGACTCAGG CATTCACTCA ACAGGCAGAT TCTCGTCTCG AAATGACGT AGGAACTACT     1440

CTAGAACCTG CTGATACTAG CACCATAAAC AATTTGGTCA TTAACATCAG TTCTATAGAC    1500

GGTGCAAAGA AGGCAAAAAT AGAAACCAAA GCTACGTCAA AAAATCTGAC TTTATCTGGA    1560

ACCATCACTT TATTGGACCC GACGGGCACG TTTTATGAAA ATCATAGTTT AAGAAATCCT    1620
```

-continued

```
CAGTCCTACG ACATCTTAGA GCTCAAAGCT TCTGGAACTG TAACAAGCAC CGCAGTGACT    1680

CCAGATCCTA TAATGGGTGA GAAATTCCAT TACGGCTATC AGGGAACTTG GGGCCCAATT    1740

GTTTGGGGGA CAGGGGCTTC TACGACTGCA ACCTTCAACT GGACTAAAAC TGGCTATATT    1800

CCTAATCCCG AGCGTATCGG CTCTTTAGTC CCTAATAGCT TATGGAATGC ATTTATAGAT    1860

ATTAGCTCTC TCCATTATCT TATGGAGACT GCAAACGAAG GGTTGCAGGG AGACCGTGCT    1920

TTTTGGTGTG CTGGATTATC TAACTTCTTC CATAAGGATA GTACAAAAAC ACGACGCGGG    1980

TTTCGCCATT TGAGTGGCGG TTATGTCATA GGAGGAAACC TACATACTTG TTCAGATAAG    2040

ATTCTTAGTG CTGCATTTTG TCAGCTCTTT GGAAGAGATA GAGACTACTT TGTAGCTAAG    2100

AATCAAGGTA CAGTCTACGG AGGAACTCTC TATTACCAGC ACAACGAAAC CTATATCTCT    2160

CTTCCTTGCA AACTACGGCC TTGTTCGTTG TCTTATGTTC CTACAGAGAT TCCTGTTCTC    2220

TTTTCAGGAA ACCTTAGCTA CACCCATACG GATAACGATC TGAAAACCAA GTATACAACA    2280

TATCCTACTG TTAAAGGAAG CTGGGGGAAT GATAGTTTCG CTTTAGAATT CGGTGGAAGA    2340

GCTCCGATTT GCTTAGATGA AAGTGCTCTA TTTGAGCAGT ACATGCCCTT CATGAAATTG    2400

CAGTTTGTCT ATGCACATCA GGAAGGTTTT AAAGAACAGG GAACAGAAGC TCGTGAATTT    2460

GGAAGTAGCC GTCTTGTGAA TCTTGCCTTA CCTATCGGGA TCCGATTTGA TAAGGAATCA    2520

GACTGCCAAG ATGCAACGTA CAATCTAACT CTTGGTTATA CTGTGGATCT TGTTCGTAGT    2580

AACCCCGACT GTACGACAAC ACTGCGAATT AGCGGTGATT CTTGGAAAAC CTTCGGTACG    2640

AATTTGGCAA GACAAGCTTT AGTCCTTCGT GCAGGGAACC ATTTTTGCTT TAACTCAAAT    2700

TTTGAAGCCT TTAGCCAATT TTCTTTTGAA TTGCGTGGGT CATCTCGCAA TTACAATGTA    2760

GACTTAGGAG CAAAATACCA ATTCTAA                                        2787
```

(2) INFORMATION FOR SEQ ID NO: 10:

(i) SEQUENCE CHARACTERISTICS:
        (A) LENGTH: 928 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 10:

```
Met Lys Ser Ser Phe Pro Lys Phe Val Phe Ser Thr Phe Ala Ile Phe
 1               5                  10                  15

Pro Leu Ser Met Ile Ala Thr Glu Thr Val Leu Asp Ser Ser Ala Ser
            20                  25                  30

Phe Asp Gly Asn Lys Asn Gly Asn Phe Ser Val Arg Glu Ser Gln Glu
        35                  40                  45

Asp Ala Gly Thr Thr Tyr Leu Phe Lys Gly Asn Val Thr Leu Glu Asn
    50                  55                  60

Ile Pro Gly Thr Gly Thr Ala Ile Thr Lys Ser Cys Phe Asn Asn Thr
65                  70                  75                  80

Lys Gly Asp Leu Thr Phe Thr Gly Asn Gly Asn Ser Leu Leu Phe Gln
                85                  90                  95

Thr Val Asp Ala Gly Thr Val Ala Gly Ala Val Asn Ser Ser Val
            100                 105                 110

Val Asp Lys Ser Thr Thr Phe Ile Gly Phe Ser Ser Leu Ser Phe Ile
        115                 120                 125

Ala Ser Pro Gly Ser Ser Ile Thr Thr Gly Lys Gly Ala Val Ser Cys
```

-continued

```
            130                 135                 140
Ser Thr Gly Ser Leu Lys Phe Asp Lys Asn Val Ser Leu Leu Phe Ser
145                 150                 155                 160

Lys Asn Phe Ser Thr Asp Asn Gly Gly Ala Ile Thr Ala Lys Thr Leu
                165                 170                 175

Ser Leu Thr Gly Thr Thr Met Ser Ala Leu Phe Ser Glu Asn Thr Ser
                180                 185                 190

Ser Lys Lys Gly Gly Ala Ile Gln Thr Ser Asp Ala Leu Thr Ile Thr
                195                 200                 205

Gly Asn Gln Gly Glu Val Ser Phe Ser Asp Asn Thr Ser Ser Asp Ser
210                 215                 220

Gly Ala Ala Ile Phe Thr Glu Ala Ser Val Thr Ile Ser Asn Asn Ala
225                 230                 235                 240

Lys Val Ser Phe Ile Asp Asn Lys Val Thr Gly Ala Ser Ser Ser Thr
                245                 250                 255

Thr Gly Asp Met Ser Gly Gly Ala Ile Cys Ala Tyr Lys Thr Ser Thr
                260                 265                 270

Asp Thr Lys Val Thr Leu Thr Gly Asn Gln Met Leu Leu Phe Ser Asn
        275                 280                 285

Asn Thr Ser Thr Thr Ala Gly Gly Ala Ile Tyr Val Lys Lys Leu Glu
        290                 295                 300

Leu Ala Ser Gly Gly Leu Thr Leu Phe Ser Arg Asn Ser Val Asn Gly
305                 310                 315                 320

Gly Thr Ala Pro Lys Gly Gly Ala Ile Ala Ile Glu Asp Ser Gly Glu
                325                 330                 335

Leu Ser Leu Ser Ala Asp Ser Gly Asp Ile Val Phe Leu Gly Asn Thr
                340                 345                 350

Val Thr Ser Thr Thr Pro Gly Thr Asn Arg Ser Ser Ile Asp Leu Gly
                355                 360                 365

Thr Ser Ala Lys Met Thr Ala Leu Arg Ser Ala Ala Gly Arg Ala Ile
                370                 375                 380

Tyr Phe Tyr Asp Pro Ile Thr Thr Gly Ser Ser Thr Thr Val Thr Asp
385                 390                 395                 400

Val Leu Lys Val Asn Glu Thr Pro Ala Asp Ser Ala Leu Gln Tyr Thr
                405                 410                 415

Gly Asn Ile Ile Phe Thr Gly Glu Lys Leu Ser Glu Thr Glu Ala Ala
                420                 425                 430

Asp Ser Lys Asn Leu Thr Ser Lys Leu Leu Gln Pro Val Thr Leu Ser
                435                 440                 445

Gly Gly Thr Leu Ser Leu Lys His Gly Val Thr Leu Gln Thr Gln Ala
450                 455                 460

Phe Thr Gln Gln Ala Asp Ser Arg Leu Glu Met Asp Val Gly Thr Thr
465                 470                 475                 480

Leu Glu Pro Ala Asp Thr Ser Thr Ile Asn Asn Leu Val Ile Asn Ile
                485                 490                 495

Ser Ser Ile Asp Gly Ala Lys Lys Ala Lys Ile Glu Thr Lys Ala Thr
                500                 505                 510

Ser Lys Asn Leu Thr Leu Ser Gly Thr Ile Thr Leu Leu Asp Pro Thr
                515                 520                 525

Gly Thr Phe Tyr Glu Asn His Ser Leu Arg Asn Pro Gln Ser Tyr Asp
                530                 535                 540

Ile Leu Glu Leu Lys Ala Ser Gly Thr Val Thr Ser Thr Ala Val Thr
545                 550                 555                 560
```

```
Pro Asp Pro Ile Met Gly Glu Lys Phe His Tyr Gly Tyr Gln Gly Thr
            565                 570                 575

Trp Gly Pro Ile Val Trp Gly Thr Gly Ala Ser Thr Thr Ala Thr Phe
            580                 585                 590

Asn Trp Thr Lys Thr Gly Tyr Ile Pro Asn Pro Glu Arg Ile Gly Ser
            595                 600                 605

Leu Val Pro Asn Ser Leu Trp Asn Ala Phe Ile Asp Ile Ser Ser Leu
            610                 615                 620

His Tyr Leu Met Glu Thr Ala Asn Glu Gly Leu Gln Gly Asp Arg Ala
625                 630                 635                 640

Phe Trp Cys Ala Gly Leu Ser Asn Phe Phe His Lys Asp Ser Thr Lys
            645                 650                 655

Thr Arg Arg Gly Phe Arg His Leu Ser Gly Gly Tyr Val Ile Gly Gly
            660                 665                 670

Asn Leu His Thr Cys Ser Asp Lys Ile Leu Ser Ala Ala Phe Cys Gln
            675                 680                 685

Leu Phe Gly Arg Asp Arg Asp Tyr Phe Val Ala Lys Asn Gln Gly Thr
            690                 695                 700

Val Tyr Gly Gly Thr Leu Tyr Tyr Gln His Asn Glu Thr Tyr Ile Ser
705                 710                 715                 720

Leu Pro Cys Lys Leu Arg Pro Cys Ser Leu Ser Tyr Val Pro Thr Glu
            725                 730                 735

Ile Pro Val Leu Phe Ser Gly Asn Leu Ser Tyr Thr His Thr Asp Asn
            740                 745                 750

Asp Leu Lys Thr Lys Tyr Thr Thr Tyr Pro Thr Val Lys Gly Ser Trp
            755                 760                 765

Gly Asn Asp Ser Phe Ala Leu Glu Phe Gly Gly Arg Ala Pro Ile Cys
            770                 775                 780

Leu Asp Glu Ser Ala Leu Phe Glu Gln Tyr Met Pro Phe Met Lys Leu
785                 790                 795                 800

Gln Phe Val Tyr Ala His Gln Glu Gly Phe Lys Glu Gln Gly Thr Glu
            805                 810                 815

Ala Arg Glu Phe Gly Ser Ser Arg Leu Val Asn Leu Ala Leu Pro Ile
            820                 825                 830

Gly Ile Arg Phe Asp Lys Glu Ser Asp Cys Gln Asp Ala Thr Tyr Asn
            835                 840                 845

Leu Thr Leu Gly Tyr Thr Val Asp Leu Val Arg Ser Asn Pro Asp Cys
            850                 855                 860

Thr Thr Thr Leu Arg Ile Ser Gly Asp Ser Trp Lys Thr Phe Gly Thr
865                 870                 875                 880

Asn Leu Ala Arg Gln Ala Leu Val Leu Arg Ala Gly Asn His Phe Cys
            885                 890                 895

Phe Asn Ser Asn Phe Glu Ala Phe Ser Gln Phe Ser Phe Glu Leu Arg
            900                 905                 910

Gly Ser Ser Arg Asn Tyr Asn Val Asp Leu Gly Ala Lys Tyr Gln Phe
            915                 920                 925
```

(2) INFORMATION FOR SEQ ID NO: 11:

(i) SEQUENCE CHARACTERISTICS:
        (A) LENGTH: 2757 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 11:

```
ATGAGATCGT CTTTTTCCTT GTTATTAATA TCTTCATCTC TAGCCTTTCC TCTCTTAATG      60
AGTGTTTCTG CAGATGCTGC CGATCTCACA TTAGGGAGTC GTGACAGTTA TAATGGTGAT     120
ACAAGCACCA CAGAATTTAC TCCTAAAGCG GCAACTTCTG ATGCTAGTGG CACGACCTAT     180
ATTCTCGATG GGGATGTCTC GATAAGCCAA GCAGGGAAAC AAACGAGCTT AACCACAAGT     240
TGTTTTTCTA ACACTGCAGG AAATCTTACC TTCTTAGGGA ACGGATTTTC TCTTCATTTT     300
GACAATATTA TTTCGTCTAC TGTTGCAGGT GTTGTTGTTA GCAATACAGC AGCTTCTGGG     360
ATTACGAAAT TCTCAGGATT TTCAACTCTT CGGATGCTTG CAGCTCCTAG GACCACAGGT     420
AAAGGAGCCA TTAAAATTAC CGATGGTCTG GTGTTTGAGA GTATAGGGAA TCTTGACCAA     480
AATGAAAATG CCTCTAGTGA AAATGGGGGA GCCATCAATA CGAAGACTTT GTCTTTGACT     540
GGGAGTACGC GGTTTGTAGC GTTCCTTGGC AATAGCTCGT CGCAACAAGG GGGAGCGATC     600
TATGCTTCTG GTGACTCTGT GATTTCTGAG AATGCAGGAA TCTTGAGCTT CGGAAACAAC     660
AGTGCGACAA CATCAGGAGG CGCGATCTCT GCTGAAGGGA ACCTTGTGAT CTCCAATAAC     720
CAAAATATCT TTTTCGATGG CTGCAAAGCA ACTACAAATG GCGGAGCTAT TGATTGTAAC     780
AAAGCAGGGG CGAACCCAGA CCCTATCTTG ACTCTTTCAG GAAATGAGAG CCTGCATTTT     840
CTGAATAACA CAGCAGGAAA TAGTGGAGGT GCGATTTATA CCAAAAAATT GGTGTTATCC     900
TCAGGACGAG GAGGAGTGTT ATTTTCTAAC AACAAAGCTG CGAATGCTAC TCCTAAAGGA     960
GGGGCAATTG CGATTCTAGA TTCTGGAGAG ATTAGCATTT CTGCAGATCT CGGCAATATC    1020
ATTTTCGAGG GCAATACTAC GAGCACTACA GGAAGTCCTG CGAGTGTGAC CAGAAATGCT    1080
ATAGATCTTG CATCGAATGC AAAATTTTTA AATCTCCGAG CGACTCGGGG AAATAAAGTT    1140
ATTTTCTATG ATCCTATCAC GAGCTCAGGA GCTACTGATA AGCTCTCTTT GAATAAAGCT    1200
GACGCAGGAT CTGGAAATAC CTATGAAGGC TACATCGTTT TCTCTGGAGA GAAACTCTCA    1260
GAAGAGGAAC TTAAGAAACC TGACAATCTG AAGTCTACAT TTACACAGGC TGTAGAGCTT    1320
GCTGCAGGTG CCTTAGTATT GAAAGATGGA GTGACTGTAG TTGCAAATAC TATAACGCAG    1380
GTCGAGGGAT CGAAAGTCGT TATGGATGGA GGGACTACTT TGAGGCAAG CGCTGAGGGG    1440
GTCACTCTCA ATGGCCTAGC CATTAATATA GATTCCTTAG ATGGGACAAA TAAAGCTATC    1500
ATTAAGGCGA CGGCAGCAAG TAAGGATGTT GCCTTATCAG GCCTATCAT GCTTGTAGAT    1560
GCTCAGGGGA ACTATTATGA GCATCATAAT CTCAGTCAAC AGCAGGTCTT TCCTTTAATA    1620
GAGCTTTCTG CACAAGGAAC GATGACTACT ACAGATATCC CCGATACCCC AATTCTAAAT    1680
ACTACGAATC ACTATGGGTA TCAAGGAACT GGAATAATTG TTTGGGTCGA CGATGCAACT    1740
GCAAAAACAA AAAATGCTAC CTTAACTTGG ACTAAAACAG GATACAAGCC GAATCCAGAA    1800
CGTCAGGGAC CTTTGGTTCC TAATAGCCTG TGGGGTTCTT TTGTCGATGT CCGCTCCATT    1860
CAGAGCCTCA TGGACCGGAG CACAAGTTCG TTATCTTCGT CAACAAATTT GTGGGTATCA    1920
GGAATCGCGG ACTTTTTGCA TGAAGATCAG AAAGGAAACC AACGTAGTTA TCGTCATTCT    1980
AGCGCGGGTT ATGCATTAGG AGGAGGATTC TTCACGGCTT CTGAAAATTT CTTTAATTTT    2040
GCTTTTTGTC AGCTTTTTGG CTACGACAAG GACCATCTTG TGGCTAAGAA CCATACCCAT    2100
GTATATGCAG GGGCAATGAG TTACCGACAC CTCGGAGAGT CTAAGACCCT CGCTAAGATT    2160
TTGTCAGGAA ATTCTGACTC CCTACCTTTT GTCTTCAATG CTCGGTTTGC TTATGGCCAT    2220
ACCGACAATA ACATGACCAC AAAGTACACT GGCTATTCTC CTGTTAAGGG AAGCTGGGGA    2280
```

```
AATGATGCCT TCGGTATAGA ATGTGGAGGA GCTATCCCGG TAGTTGCTTC AGGACGTCGG    2340

TCTTGGGTGG ATACCCACAC GCCATTTCTA AACCTAGAGA TGATCTATGC ACATCAGAAT    2400

GACTTTAAGG AAAACGGCAC AGAAGGCCGT TCTTTCCAAA GTGAAGACCT CTTCAATCTA    2460

GCGGTTCCTG TAGGGATAAA ATTTGAGAAA TTCTCCGATA AGTCTACGTA TGATCTCTCC    2520

ATAGCTTACG TTCCCGATGT GATTCGTAAT GATCCAGGCT GCACGACAAC TCTTATGGTT    2580

TCTGGGGATT CTTGGTCGAC ATGTGGTACA AGCTTGTCTA GACAAGCTCT TCTTGTACGT    2640

GCTGGAAATC ATCATGCCTT TGCTTCAAAC TTTGAAGTTT TCAGTCAGTT TGAAGTCGAG    2700

TTGCGAGGTT CTTCTCGTAG CTATGCTATC GATCTTGGAG GAAGATTCGG ATTTTAA      2757
```

(2) INFORMATION FOR SEQ ID NO: 12:

(i) SEQUENCE CHARACTERISTICS:
        (A) LENGTH: 918 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 12:

```
Met Arg Ser Ser Phe Ser Leu Leu Ile Ser Ser Leu Ala Phe
 1               5                  10                  15

Pro Leu Leu Met Ser Val Ser Ala Asp Ala Ala Asp Leu Thr Leu Gly
                20                  25                  30

Ser Arg Asp Ser Tyr Asn Gly Asp Thr Ser Thr Thr Glu Phe Thr Pro
            35                  40                  45

Lys Ala Ala Thr Ser Asp Ala Ser Gly Thr Thr Tyr Ile Leu Asp Gly
 50                  55                  60

Asp Val Ser Ile Ser Gln Ala Gly Lys Gln Thr Ser Leu Thr Thr Ser
 65                  70                  75                  80

Cys Phe Ser Asn Thr Ala Gly Asn Leu Thr Phe Leu Gly Asn Gly Phe
                85                  90                  95

Ser Leu His Phe Asp Asn Ile Ile Ser Ser Thr Val Ala Gly Val Val
                100                 105                 110

Val Ser Asn Thr Ala Ala Ser Gly Ile Thr Lys Phe Ser Gly Phe Ser
            115                 120                 125

Thr Leu Arg Met Leu Ala Ala Pro Arg Thr Thr Gly Lys Gly Ala Ile
130                 135                 140

Lys Ile Thr Asp Gly Leu Val Phe Glu Ser Ile Gly Asn Leu Asp Gln
145                 150                 155                 160

Asn Glu Asn Ala Ser Ser Glu Asn Gly Gly Ala Ile Asn Thr Lys Thr
                165                 170                 175

Leu Ser Leu Thr Gly Ser Thr Arg Phe Val Ala Phe Leu Gly Asn Ser
            180                 185                 190

Ser Ser Gln Gln Gly Gly Ala Ile Tyr Ala Ser Gly Asp Ser Val Ile
        195                 200                 205

Ser Glu Asn Ala Gly Ile Leu Ser Phe Gly Asn Asn Ser Ala Thr Thr
210                 215                 220

Ser Gly Gly Ala Ile Ser Ala Glu Gly Asn Leu Val Ile Ser Asn Asn
225                 230                 235                 240

Gln Asn Ile Phe Phe Asp Gly Cys Lys Ala Thr Thr Asn Gly Gly Ala
                245                 250                 255

Ile Asp Cys Asn Lys Ala Gly Ala Asn Pro Asp Pro Ile Leu Thr Leu
```

-continued

```
                260                 265                 270
Ser Gly Asn Glu Ser Leu His Phe Leu Asn Asn Thr Ala Gly Asn Ser
            275                 280                 285
Gly Gly Ala Ile Tyr Thr Lys Lys Leu Val Leu Ser Ser Gly Arg Gly
        290                 295                 300
Gly Val Leu Phe Ser Asn Asn Lys Ala Ala Asn Ala Thr Pro Lys Gly
305                 310                 315                 320
Gly Ala Ile Ala Ile Leu Asp Ser Gly Glu Ile Ser Ile Ser Ala Asp
                325                 330                 335
Leu Gly Asn Ile Ile Phe Glu Gly Asn Thr Thr Ser Thr Thr Gly Ser
            340                 345                 350
Pro Ala Ser Val Thr Arg Asn Ala Ile Asp Leu Ala Ser Asn Ala Lys
        355                 360                 365
Phe Leu Asn Leu Arg Ala Thr Arg Gly Asn Lys Val Ile Phe Tyr Asp
    370                 375                 380
Pro Ile Thr Ser Ser Gly Ala Thr Asp Lys Leu Ser Leu Asn Lys Ala
385                 390                 395                 400
Asp Ala Gly Ser Gly Asn Thr Tyr Glu Gly Tyr Ile Val Phe Ser Gly
                405                 410                 415
Glu Lys Leu Ser Glu Glu Leu Lys Lys Pro Asp Asn Leu Lys Ser
            420                 425                 430
Thr Phe Thr Gln Ala Val Glu Leu Ala Ala Gly Ala Leu Val Leu Lys
        435                 440                 445
Asp Gly Val Thr Val Ala Asn Thr Ile Thr Gln Val Glu Gly Ser
    450                 455                 460
Lys Val Val Met Asp Gly Gly Thr Thr Phe Glu Ala Ser Ala Glu Gly
465                 470                 475                 480
Val Thr Leu Asn Gly Leu Ala Ile Asn Ile Asp Ser Leu Asp Gly Thr
                485                 490                 495
Asn Lys Ala Ile Ile Lys Ala Thr Ala Ser Lys Asp Val Ala Leu
            500                 505                 510
Ser Gly Pro Ile Met Leu Val Asp Ala Gln Gly Asn Tyr Tyr Glu His
        515                 520                 525
His Asn Leu Ser Gln Gln Val Phe Pro Leu Ile Glu Leu Ser Ala
    530                 535                 540
Gln Gly Thr Met Thr Thr Thr Asp Ile Pro Asp Thr Pro Ile Leu Asn
545                 550                 555                 560
Thr Thr Asn His Tyr Gly Tyr Gln Gly Thr Gly Ile Ile Val Trp Val
                565                 570                 575
Asp Asp Ala Thr Ala Lys Thr Lys Asn Ala Thr Leu Thr Trp Thr Lys
            580                 585                 590
Thr Gly Tyr Lys Pro Asn Pro Glu Arg Gln Gly Pro Leu Val Pro Asn
        595                 600                 605
Ser Leu Trp Gly Ser Phe Val Asp Val Arg Ser Ile Gln Ser Leu Met
    610                 615                 620
Asp Arg Ser Thr Ser Ser Leu Ser Ser Ser Thr Asn Leu Trp Val Ser
625                 630                 635                 640
Gly Ile Ala Asp Phe Leu His Glu Asp Gln Lys Gly Asn Gln Arg Ser
                645                 650                 655
Tyr Arg His Ser Ser Ala Gly Tyr Ala Leu Gly Gly Phe Phe Thr
            660                 665                 670
Ala Ser Glu Asn Phe Phe Asn Phe Ala Phe Cys Gln Leu Phe Gly Tyr
        675                 680                 685
```

```
Asp Lys Asp His Leu Val Ala Lys Asn His Thr His Val Tyr Ala Gly
        690                 695                 700
Ala Met Ser Tyr Arg His Leu Gly Glu Ser Lys Thr Leu Ala Lys Ile
705                 710                 715                 720
Leu Ser Gly Asn Ser Asp Ser Leu Pro Phe Val Phe Asn Ala Arg Phe
                725                 730                 735
Ala Tyr Gly His Thr Asp Asn Asn Met Thr Thr Lys Tyr Thr Gly Tyr
            740                 745                 750
Ser Pro Val Lys Gly Ser Trp Gly Asn Asp Ala Phe Gly Ile Glu Cys
        755                 760                 765
Gly Gly Ala Ile Pro Val Val Ala Ser Gly Arg Arg Ser Trp Val Asp
    770                 775                 780
Thr His Thr Pro Phe Leu Asn Leu Glu Met Ile Tyr Ala His Gln Asn
785                 790                 795                 800
Asp Phe Lys Glu Asn Gly Thr Glu Gly Arg Ser Phe Gln Ser Glu Asp
                805                 810                 815
Leu Phe Asn Leu Ala Val Pro Val Gly Ile Lys Phe Glu Lys Phe Ser
            820                 825                 830
Asp Lys Ser Thr Tyr Asp Leu Ser Ile Ala Tyr Val Pro Asp Val Ile
        835                 840                 845
Arg Asn Asp Pro Gly Cys Thr Thr Thr Leu Met Val Ser Gly Asp Ser
    850                 855                 860
Trp Ser Thr Cys Gly Thr Ser Leu Ser Arg Gln Ala Leu Leu Val Arg
865                 870                 875                 880
Ala Gly Asn His His Ala Phe Ala Ser Asn Phe Glu Val Phe Ser Gln
                885                 890                 895
Phe Glu Val Glu Leu Arg Gly Ser Ser Arg Ser Tyr Ala Ile Asp Leu
            900                 905                 910
Gly Gly Arg Phe Gly Phe
    915

(2) INFORMATION FOR SEQ ID NO: 13:

(i) SEQUENCE CHARACTERISTICS:
        (A) LENGTH: 2787 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 13:

ATGAAATCCT CTCTTCATTG GTTTGTAATC TCGTCATCTT TAGCACTTCC CTTGTCACTA      60

AATTTCTCTG CGTTTGCTGC TGTTGTTGAA ATCAATCTAG GACCTACCAA TAGCTTCTCT     120

GGACCAGGAA CCTACACTCC TCCAGCCCAA ACAACAAATG CAGATGGAAC TATCTATAAT     180

CTAACAGGGG ATGTCTCAAT CACCAATGCA GGATCTCCGA CAGCTCTAAC CGCTTCCTGC     240

TTTAAAGAAA CTACTGGGAA TCTTTCTTTC CAAGGCCACG GCTACCAATT TCTCCTACAA     300

AATATCGATG CGGGAGCGAA CTGTACCTTT ACCAATACAG CTGCAAATAA GCTTCTCTCC     360

TTTTCAGGAT TCTCCTATTT GTCACTAATA CAAACCACGA ATGCTACCAC AGGAACAGGA     420

GCCATCAAGT CCACAGGAGC TTGTTCTATT CAGTCGAACT ATAGTTGCTA CTTTGGCCAA     480

AACTTTTCTA ATGACAATGG AGGCGCCCTC CAAGGCAGCT CTATCAGTCT ATCGCTAAAC     540

CCCAACCTAA CGTTTGCCAA AAACAAAGCA ACGCAAAAAG GGGGTGCCCT CTATTCCACG     600
```

```
GGAGGGATTA CAATTAACAA TACGTTAAAC TCAGCATCAT TTTCTGAAAA TACCGCGGCG      660

AACAATGGCG GAGCCATTTA CACGGAAGCT AGCAGTTTTA TTAGCAGCAA CAAAGCAATT      720

AGCTTTATAA ACAATAGTGT GACCGCAACC TCAGCTACAG GGGGAGCCAT TTACTGTAGT      780

AGTACATCAG CCCCCAAACC AGTCTTAACT CTATCAGACA ACGGGGAACT GAACTTTATA      840

GGAAATACAG CAATTACTAG TGGTGGGGCG ATTTATACTG ACAATCTAGT TCTTTCTTCT      900

GGAGGACCTA CGCTTTTTAA AAACAACTCT GCTATAGATA CTGCAGCTCC CTTAGGAGGA      960

GCAATTGCGA TTGCTGACTC TGGATCTTTG AGTCTTTCGG CTCTTGGTGG AGACATCACT     1020

TTTGAAGGAA ACACAGTAGT CAAAGGAGCT TCTTCGAGTC AGACCACTAC CAGAAATTCT     1080

ATTAACATCG GAAACACCAA TGCTAAGATT GTACAGCTGC GAGCCTCTCA AGGCAATACT     1140

ATCTACTTCT ATGATCCTAT AACAACTAAC CATACTGCAG CTCTCTCAGA TGCTCTAAAC     1200

TTAAATGGTC CTGACCTTGC AGGGAATCCT GCATATCAAG GAACCATCGT ATTTTCTGGA     1260

GAGAAGCTCT CGGAAGCAGA AGCTGCAGAA GCTGATAATC TCAAATCTAC AATTCAGCAA     1320

CCTCTAACTC TTGCGGGAGG GCAACTCTCT CTTAAATCAG GAGTCACTCT AGTTGCTAAG     1380

TCCTTTTCGC AATCTCCGGG CTCTACCCTC TCATGGATG CAGGGACCAC ATTAGAAACC     1440

GCTGATGGGA TCACTATCAA TAATCTTGTT CTCAATGTAG ATTCCTTAAA AGAGACCAAG     1500

AAGGCTACGC TAAAAGCAAC ACAAGCAAGT CAGACAGTCA CTTTATCTGG ATCGCTCTCT     1560

CTTGTAGATC CTTCTGGAAA TGTCTACGAA GATGTCTCTT GGAATAACCC TCAAGTCTTT     1620

TCTTGTCTCA CTCTTACTGC TGACGACCCC GCGAATATTC ACATCACAGA CTTAGCTGCT     1680

GATCCCCTAG AAAAAAATCC TATCCATTGG GGATACCAAG GGAATTGGGC ATTATCTTGG     1740

CAAGAGGATA CTGCGACTAA ATCCAAAGCA GCGACTCTTA CCTGGACAAA AACAGGATAC     1800

AATCCGAATC CTGAGCGTCG TGGAACCTTA GTTGCTAACA CGCTATGGGG ATCCTTTGTT     1860

GATGTGCGCT CCATACAACA GCTTGTAGCC ACTAAAGTAC GCCAATCTCA AGAAACTCGC     1920

GGCATCTGGT GTGAAGGGAT CTCGAACTTC TTCCATAAAG ATAGCACGAA GATAAATAAA     1980

GGTTTTCGCC ACATAAGTGC AGGTTATGTT GTAGGAGCGA CTACAACATT AGCTTCTGAT     2040

AATCTTATCA CTGCAGCCTT CTGCCAATTA TTCGGGAAAG ATAGAGATCA CTTTATAAAT     2100

AAAAATAGAG CTTCTGCCTA TGCAGCTTCT CTCCATCTCC AGCATCTAGC GACCTTGTCT     2160

TCTCCAAGCT TGTTACGCTA CCTTCCTGGA TCTGAAAGTG AGCAGCCTGT CCTCTTTGAT     2220

GCTCAGATCA GCTATATCTA TAGTAAAAAT ACTATGAAAA CCTATTACAC CCAAGCACCA     2280

AAGGGAGAGA GCTCGTGGTA TAATGACGGT TGCGCTCTGG AACTTGCGAG CTCCCTACCA     2340

CACACTGCTT TAAGCCATGA GGGTCTCTTC CACGCGTATT TTCCTTTCAT CAAAGTAGAA     2400

GCTTCGTACA TACACCAAGA TAGCTTCAAA GAACGTAATA CTACCTTGGT ACGATCTTTC     2460

GATAGCGGTG ATTTAATTAA CGTCTCTGTG CCTATTGGAA TTACCTTCGA GAGATTCTCG     2520

AGAAACGAGC GTGCGTCTTA CGAAGCTACT GTCATCTACG TTGCCGATGT CTATCGTAAG     2580

AATCCTGACT GCACGACAGC TCTCCTAATC AACAATACCT CGTGGAAAAC TACAGGAACG     2640

AATCTCTCAA GACAAGCTGG TATCGGAAGA GCAGGGATCT TTTATGCCTT CTCTCCAAAT     2700

CTTGAGGTCA CAAGTAACCT ATCTATGGAA ATTCGTGGAT CTTCACGCAG CTACAATGCA     2760

GATCTTGGAG GTAAGTTCCA GTTCTAA                                         2787
```

(2) INFORMATION FOR SEQ ID NO: 14:

(i) SEQUENCE CHARACTERISTICS:
        (A) LENGTH: 928 amino acids (B) TYPE: amino acid
(C) STRANDEDNESS: single
(D) TOPOLOGY: linear (ii) MOLECULE TYPE: peptide (xi) SEQUENCE DESCRIPTION: SEQ ID NO: 14:

```
Met Lys Ser Ser Leu His Trp Phe Val Ile Ser Ser Leu Ala Leu
  1               5                  10                  15

Pro Leu Ser Leu Asn Phe Ser Ala Phe Ala Val Val Glu Ile Asn
             20                  25                  30

Leu Gly Pro Thr Asn Ser Phe Ser Gly Pro Gly Thr Tyr Thr Pro Pro
             35                  40                  45

Ala Gln Thr Thr Asn Ala Asp Gly Thr Ile Tyr Asn Leu Thr Gly Asp
         50                  55                  60

Val Ser Ile Thr Asn Ala Gly Ser Pro Thr Ala Leu Thr Ala Ser Cys
 65                  70                  75                  80

Phe Lys Glu Thr Thr Gly Asn Leu Ser Phe Gln Gly His Gly Tyr Gln
                 85                  90                  95

Phe Leu Leu Gln Asn Ile Asp Ala Gly Ala Asn Cys Thr Phe Thr Asn
                100                 105                 110

Thr Ala Ala Asn Lys Leu Leu Ser Phe Ser Gly Phe Ser Tyr Leu Ser
            115                 120                 125

Leu Ile Gln Thr Thr Asn Ala Thr Gly Thr Gly Ala Ile Lys Ser
        130                 135                 140

Thr Gly Ala Cys Ser Ile Gln Ser Asn Tyr Ser Cys Tyr Phe Gly Gln
145                 150                 155                 160

Asn Phe Ser Asn Asp Asn Gly Gly Ala Leu Gln Gly Ser Ser Ile Ser
                165                 170                 175

Leu Ser Leu Asn Pro Asn Leu Thr Phe Ala Lys Asn Lys Ala Thr Gln
                180                 185                 190

Lys Gly Gly Ala Leu Tyr Ser Thr Gly Gly Ile Thr Ile Asn Asn Thr
            195                 200                 205

Leu Asn Ser Ala Ser Phe Ser Glu Asn Thr Ala Ala Asn Asn Gly Gly
        210                 215                 220

Ala Ile Tyr Thr Glu Ala Ser Ser Phe Ile Ser Ser Asn Lys Ala Ile
225                 230                 235                 240

Ser Phe Ile Asn Asn Ser Val Thr Ala Thr Ser Ala Thr Gly Gly Ala
                245                 250                 255

Ile Tyr Cys Ser Ser Thr Ser Ala Pro Lys Pro Val Leu Thr Leu Ser
            260                 265                 270

Asp Asn Gly Glu Leu Asn Phe Ile Gly Asn Thr Ala Ile Thr Ser Gly
        275                 280                 285

Gly Ala Ile Tyr Thr Asp Asn Leu Val Leu Ser Ser Gly Gly Pro Thr
    290                 295                 300

Leu Phe Lys Asn Asn Ser Ala Ile Asp Thr Ala Ala Pro Leu Gly Gly
305                 310                 315                 320

Ala Ile Ala Ile Ala Asp Ser Gly Ser Leu Ser Leu Ser Ala Leu Gly
                325                 330                 335

Gly Asp Ile Thr Phe Glu Gly Asn Thr Val Val Lys Gly Ala Ser Ser
            340                 345                 350

Ser Gln Thr Thr Thr Arg Asn Ser Ile Asn Ile Gly Asn Thr Asn Ala
        355                 360                 365

Lys Ile Val Gln Leu Arg Ala Ser Gln Gly Asn Thr Ile Tyr Phe Tyr
    370                 375                 380
```

-continued

```
Asp Pro Ile Thr Thr Asn His Thr Ala Ala Leu Ser Asp Ala Leu Asn
385                 390                 395                 400

Leu Asn Gly Pro Asp Leu Ala Gly Asn Pro Ala Tyr Gln Gly Thr Ile
            405                 410                 415

Val Phe Ser Gly Glu Lys Leu Ser Glu Ala Glu Ala Ala Glu Ala Asp
            420                 425                 430

Asn Leu Lys Ser Thr Ile Gln Gln Pro Leu Thr Leu Ala Gly Gly Gln
            435                 440                 445

Leu Ser Leu Lys Ser Gly Val Thr Leu Val Ala Lys Ser Phe Ser Gln
    450                 455                 460

Ser Pro Gly Ser Thr Leu Leu Met Asp Ala Gly Thr Thr Leu Glu Thr
465                 470                 475                 480

Ala Asp Gly Ile Thr Ile Asn Asn Leu Val Leu Asn Val Asp Ser Leu
                485                 490                 495

Lys Glu Thr Lys Lys Ala Thr Leu Lys Ala Thr Gln Ala Ser Gln Thr
            500                 505                 510

Val Thr Leu Ser Gly Ser Leu Ser Leu Val Asp Pro Ser Gly Asn Val
            515                 520                 525

Tyr Glu Asp Val Ser Trp Asn Asn Pro Gln Val Phe Ser Cys Leu Thr
    530                 535                 540

Leu Thr Ala Asp Pro Ala Asn Ile His Ile Thr Asp Leu Ala Ala
545                 550                 555                 560

Asp Pro Leu Glu Lys Asn Pro Ile His Trp Gly Tyr Gln Gly Asn Trp
            565                 570                 575

Ala Leu Ser Trp Gln Glu Asp Thr Ala Thr Lys Ser Lys Ala Ala Thr
            580                 585                 590

Leu Thr Trp Thr Lys Thr Gly Tyr Asn Pro Asn Pro Glu Arg Arg Gly
            595                 600                 605

Thr Leu Val Ala Asn Thr Leu Trp Gly Ser Phe Val Asp Val Arg Ser
            610                 615                 620

Ile Gln Gln Leu Val Ala Thr Lys Val Arg Gln Ser Gln Glu Thr Arg
625                 630                 635                 640

Gly Ile Trp Cys Glu Gly Ile Ser Asn Phe Phe His Lys Asp Ser Thr
                645                 650                 655

Lys Ile Asn Lys Gly Phe Arg His Ile Ser Ala Gly Tyr Val Val Gly
            660                 665                 670

Ala Thr Thr Thr Leu Ala Ser Asp Asn Leu Ile Thr Ala Ala Phe Cys
            675                 680                 685

Gln Leu Phe Gly Lys Asp Arg Asp His Phe Ile Asn Lys Asn Arg Ala
            690                 695                 700

Ser Ala Tyr Ala Ala Ser Leu His Leu Gln His Leu Ala Thr Leu Ser
705                 710                 715                 720

Ser Pro Ser Leu Leu Arg Tyr Leu Pro Gly Ser Glu Ser Glu Gln Pro
            725                 730                 735

Val Leu Phe Asp Ala Gln Ile Ser Tyr Ile Tyr Ser Lys Asn Thr Met
            740                 745                 750

Lys Thr Tyr Tyr Thr Gln Ala Pro Lys Gly Glu Ser Ser Trp Tyr Asn
            755                 760                 765

Asp Gly Cys Ala Leu Glu Leu Ala Ser Ser Leu Pro His Thr Ala Leu
            770                 775                 780

Ser His Glu Gly Leu Phe His Ala Tyr Phe Pro Phe Ile Lys Val Glu
785                 790                 795                 800
```

Ala Ser Tyr Ile His Gln Asp Ser Phe Lys Glu Arg Asn Thr Thr Leu
            805                 810                 815

Val Arg Ser Phe Asp Ser Gly Asp Leu Ile Asn Val Ser Val Pro Ile
            820                 825                 830

Gly Ile Thr Phe Glu Arg Phe Ser Arg Asn Glu Arg Ala Ser Tyr Glu
            835                 840                 845

Ala Thr Val Ile Tyr Val Ala Asp Val Tyr Arg Lys Asn Pro Asp Cys
850                 855                 860

Thr Thr Ala Leu Leu Ile Asn Asn Thr Ser Trp Lys Thr Thr Gly Thr
865                 870                 875                 880

Asn Leu Ser Arg Gln Ala Gly Ile Gly Arg Ala Gly Ile Phe Tyr Ala
            885                 890                 895

Phe Ser Pro Asn Leu Glu Val Thr Ser Asn Leu Ser Met Glu Ile Arg
            900                 905                 910

Gly Ser Ser Arg Ser Tyr Asn Ala Asp Leu Gly Gly Lys Phe Gln Phe
            915                 920                 925

(2) INFORMATION FOR SEQ ID NO: 15:

(i) SEQUENCE CHARACTERISTICS:
        (A) LENGTH: 2793 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 15:

```
ATGAAAATAC CCTTGCACAA ACTCCTGATC TCTTCGACTC TTGTCACTCC CATTCTATTG      60

AGCATTGCAA CTTACGGAGC AGATGCTTCT TTATCCCCTA CAGATAGCTT TGATGGAGCG     120

GGCGGCTCTA CATTTACTCC AAAATCTACA GCAGATGCCA ATGGAACGAA CTATGTCTTA     180

TCAGGAAATG TCTATATAAA CGATGCTGGG AAAGGCACAG CATTAACAGG CTGCTGCTTT     240

ACAGAAACTA CGGGTGATCT GACATTTACT GGAAAGGGAT ACTCATTTTC ATTCAACACG     300

GTAGATGCGG GTTCGAATGC AGGAGCTGCG GCAAGCACAA CTGCTGATAA AGCCCTAACA     360

TTCACAGGAT TTTCTAACCT TTCCTTCATT GCAGCTCCTG AACTACAGT TGCTTCAGGA      420

AAAAGTACTT TAAGTTCTGC AGGAGCCTTA AATCTTACCG ATAATGGAAC GATTCTCTTT     480

AGCCAAAACG TCTCCAATGA AGCTAATAAC AATGGCGGAG CGATCACCAC AAAAACTCTT     540

TCTATTTCTG GGAATACCTC TTCTATAACC TTCACTAGTA ATAGCGCAAA AAAATTAGGT     600

GGAGCGATCT ATAGCTCTGC GGCTGCAAGT ATTTCAGGAA ACACCGGCCA GTTAGTCTTT     660

ATGAATAATA AAGGAGAAAC TGGGGGCGGG GCTCTGGGCT TTGAAGCCAG CTCCTCGATT     720

ACTCAAAATA GCTCCCTTTT CTTCTCTGGA AACACTGCAA CAGATGCTGC AGGCAAGGGC     780

GGGGCCATTT ATTGTGAAAA AACAGGAGAG ACTCCTACTC TTACTATCTC TGGAAATAAA     840

AGTCTGACCT TCGCCGAGAA CTCTTCAGTA ACTCAAGGCG GAGCAATCTG TGCCCATGGT     900

CTAGATCTTT CCGCTGCTGG CCCTACCCTA TTTTCAAATA ATAGATGCGG GAACACAGCT     960

GCAGGCAAGG GCGGCGCTAT TGCAATTGCC GACTCTGGAT CTTTAAGTCT CTCTGCAAAT    1020

CAAGGAGACA TCACGTTCCT TGGCAACACT CTAACCTCAA CCTCCGCGCC AACATCGACA    1080

CGGAATGCTA TCTACCTGGG ATCGTCAGCA AAAATTACGA ACTTAAGGGC AGCCCAAGGC    1140

CAATCTATCT ATTTCTATGA TCCGATTGCA CTAACACCA CAGGAGCTTC AGACGTTCTG     1200

ACCATCAACC AACCGGATAG CAACTCGCCT TTAGATTATT CAGGAACGAT TGTATTTTCT    1260
```

-continued

```
GGGGAAAAGC TCTCTGCAGA TGAAGCGAAA GCTGCTGATA ACTTCACATC TATATTAAAG    1320

CAACCATTGG CTCTAGCCTC TGGAACCTTA GCACTCAAAG GAAATGTCGA GTTAGATGTC    1380

AATGGTTTCA CACAGACTGA AGGCTCTACA CTCCTCATGC AACCAGGAAC AAAGCTCAAA    1440

GCAGATACTG AAGCTATCAG TCTTACCAAA CTTGTCGTTG ATCTTTCTGC CTTAGAGGGA    1500

AATAAGAGTG TGTCCATTGA AACAGCAGGA GCCAACAAAA CTATAACTCT AACCTCTCCT    1560

CTTGTTTTCC AAGATAGTAG CGGCAATTTT TATGAAAGCC ATACGATAAA CCAAGCCTTC    1620

ACGCAGCCTT TGGTGGTATT CACTGCTGCT ACTGCTGCTA GCGATATTTA TATCGATGCG    1680

CTTCTCACTT CTCCAGTACA AACTCCAGAA CCTCATTACG GGTATCAGGG ACATTGGGAA    1740

GCCACTTGGG CAGACACATC AACTGCAAAA TCAGGAACTA TGACTTGGGT AACTACGGGC    1800

TACAACCCTA ATCCTGAGCG TAGAGCTTCC GTAGTTCCCG ATTCATTATG GGCATCCTTT    1860

ACTGACATTC GCACTCTACA GCAGATCATG ACATCTCAAG CGAATAGTAT CTATCAGCAA    1920

CGAGGACTCT GGGCATCAGG AACTGCGAAT TCTTCCATA AGGATAAATC AGGAACTAAC     1980

CAAGCATTCC GACATAAAAG CTACGGCTAT ATTGTTGGAG GAAGTGCTGA AGATTTTTCT    2040

GAAAATATCT TCAGTGTAGC TTTCTGCCAG CTCTTCGGTA AAGATAAAGA CCTGTTTATA    2100

GTTGAAAATA CCTCTCATAA CTATTTAGCG TCGCTATACC TGCAACATCG AGCATTCCTA    2160

GGAGGACTTC CCATGCCCTC ATTTGGAAGT ATCACCGACA TGCTGAAAGA TATTCCTCTC    2220

ATTTTGAATG CCCAGCTAAG CTACAGCTAC ACTAAAAATG ATATGGATAC TCGCTATACT    2280

TCCTATCCTG AAGCTCAAGG TTCTTGGACC AATAATTCTG GGGCTCTAGA GCTCGGAGGA    2340

TCTCTGGCTC TATATCTCCC TAAAGAAGCA CCGTTCTTCC AGGGATATTT CCCCTTCTTA    2400

AAGTTCCAGG CAGTCTACAG CCGCCAACAA AACTTTAAAG AGAGTGGCGC TGAAGCCCGT    2460

GCTTTTGATG ATGGAGACCT AGTGAACTGC TCTATCCCTG TCGGCATTCG GTTAGAAAAA    2520

ATCTCCGAAG ATGAAAAAAA TAATTTCGAG ATTTCTCTAG CCAACATTGG TGATGTGTAT    2580

CGTAAAAATC CCCGTTCGCG TACTTCTCTA ATGGTCAGTG GAGCCTCTTG GACTTCGCTA    2640

TGTAAAAACC TCGCACGACA AGCCTTCTTA GCAAGTGCTG GAAGCCATCT GACTCTCTCC    2700

CCTCATGTAG AACTCTCTGG GGAAGCTGCT TATGAGCTTC GTGGCTCAGC ACACATCTAC    2760

AATGTAGATT GTGGGCTAAG ATACTCATTC TAG                                2793
```

(2) INFORMATION FOR SEQ ID NO: 16:

(i) SEQUENCE CHARACTERISTICS:
        (A) LENGTH: 930 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 16:

```
Met Lys Ile Pro Leu His Lys Leu Leu Ile Ser Ser Thr Leu Val Thr
 1               5                  10                  15

Pro Ile Leu Leu Ser Ile Ala Thr Tyr Gly Ala Asp Ala Ser Leu Ser
             20                  25                  30

Pro Thr Asp Ser Phe Asp Gly Ala Gly Gly Ser Thr Phe Thr Pro Lys
         35                  40                  45

Ser Thr Ala Asp Ala Asn Gly Thr Asn Tyr Val Leu Ser Gly Asn Val
     50                  55                  60

Tyr Ile Asn Asp Ala Gly Lys Gly Thr Ala Leu Thr Gly Cys Cys Phe
 65                  70                  75                  80
```

```
Thr Glu Thr Thr Gly Asp Leu Thr Phe Thr Gly Lys Gly Tyr Ser Phe
                85                  90                  95

Ser Phe Asn Thr Val Asp Ala Gly Ser Asn Ala Gly Ala Ala Ala Ser
            100                 105                 110

Thr Thr Ala Asp Lys Ala Leu Thr Phe Thr Gly Phe Ser Asn Leu Ser
            115                 120                 125

Phe Ile Ala Ala Pro Gly Thr Thr Val Ala Ser Gly Lys Ser Thr Leu
    130                 135                 140

Ser Ser Ala Gly Ala Leu Asn Leu Thr Asp Asn Gly Thr Ile Leu Phe
145                 150                 155                 160

Ser Gln Asn Val Ser Asn Glu Ala Asn Asn Asn Gly Gly Ala Ile Thr
                165                 170                 175

Thr Lys Thr Leu Ser Ile Ser Gly Asn Thr Ser Ser Ile Thr Phe Thr
            180                 185                 190

Ser Asn Ser Ala Lys Lys Leu Gly Gly Ala Ile Tyr Ser Ser Ala Ala
            195                 200                 205

Ala Ser Ile Ser Gly Asn Thr Gly Gln Leu Val Phe Met Asn Asn Lys
    210                 215                 220

Gly Glu Thr Gly Gly Gly Ala Leu Gly Phe Glu Ala Ser Ser Ser Ile
225                 230                 235                 240

Thr Gln Asn Ser Ser Leu Phe Phe Ser Gly Asn Thr Ala Thr Asp Ala
                245                 250                 255

Ala Gly Lys Gly Gly Ala Ile Tyr Cys Glu Lys Thr Gly Glu Thr Pro
            260                 265                 270

Thr Leu Thr Ile Ser Gly Asn Lys Ser Leu Thr Phe Ala Glu Asn Ser
    275                 280                 285

Ser Val Thr Gln Gly Gly Ala Ile Cys Ala His Gly Leu Asp Leu Ser
            290                 295                 300

Ala Ala Gly Pro Thr Leu Phe Ser Asn Asn Arg Cys Gly Asn Thr Ala
305                 310                 315                 320

Ala Gly Lys Gly Gly Ala Ile Ala Ile Ala Asp Ser Gly Ser Leu Ser
                325                 330                 335

Leu Ser Ala Asn Gln Gly Asp Ile Thr Phe Leu Gly Asn Thr Leu Thr
            340                 345                 350

Ser Thr Ser Ala Pro Thr Ser Thr Arg Asn Ala Ile Tyr Leu Gly Ser
            355                 360                 365

Ser Ala Lys Ile Thr Asn Leu Arg Ala Ala Gln Gly Gln Ser Ile Tyr
    370                 375                 380

Phe Tyr Asp Pro Ile Ala Ser Asn Thr Thr Gly Ala Ser Asp Val Leu
385                 390                 395                 400

Thr Ile Asn Gln Pro Asp Ser Asn Ser Pro Leu Asp Tyr Ser Gly Thr
                405                 410                 415

Ile Val Phe Ser Gly Glu Lys Leu Ser Ala Asp Glu Ala Lys Ala Ala
            420                 425                 430

Asp Asn Phe Thr Ser Ile Leu Lys Gln Pro Leu Ala Leu Ala Ser Gly
            435                 440                 445

Thr Leu Ala Leu Lys Gly Asn Val Glu Leu Asp Val Asn Gly Phe Thr
    450                 455                 460

Gln Thr Glu Gly Ser Thr Leu Leu Met Gln Pro Gly Thr Lys Leu Lys
465                 470                 475                 480

Ala Asp Thr Glu Ala Ile Ser Leu Thr Lys Leu Val Val Asp Leu Ser
                485                 490                 495
```

```
Ala Leu Glu Gly Asn Lys Ser Val Ser Ile Glu Thr Ala Gly Ala Asn
            500                 505                 510

Lys Thr Ile Thr Leu Thr Ser Pro Leu Val Phe Gln Asp Ser Ser Gly
        515                 520                 525

Asn Phe Tyr Glu Ser His Thr Ile Asn Gln Ala Phe Thr Gln Pro Leu
    530                 535                 540

Val Val Phe Thr Ala Ala Thr Ala Ala Ser Asp Ile Tyr Ile Asp Ala
545                 550                 555                 560

Leu Leu Thr Ser Pro Val Gln Thr Pro Glu Pro His Tyr Gly Tyr Gln
            565                 570                 575

Gly His Trp Glu Ala Thr Trp Ala Asp Thr Ser Thr Ala Lys Ser Gly
            580                 585                 590

Thr Met Thr Trp Val Thr Thr Gly Tyr Asn Pro Asn Pro Glu Arg Arg
        595                 600                 605

Ala Ser Val Val Pro Asp Ser Leu Trp Ala Ser Phe Thr Asp Ile Arg
    610                 615                 620

Thr Leu Gln Gln Ile Met Thr Ser Gln Ala Asn Ser Ile Tyr Gln Gln
625                 630                 635                 640

Arg Gly Leu Trp Ala Ser Gly Thr Ala Asn Phe Phe His Lys Asp Lys
            645                 650                 655

Ser Gly Thr Asn Gln Ala Phe Arg His Lys Ser Tyr Gly Tyr Ile Val
            660                 665                 670

Gly Gly Ser Ala Glu Asp Phe Ser Glu Asn Ile Phe Ser Val Ala Phe
        675                 680                 685

Cys Gln Leu Phe Gly Lys Asp Lys Asp Leu Phe Ile Val Glu Asn Thr
    690                 695                 700

Ser His Asn Tyr Leu Ala Ser Leu Tyr Leu Gln His Arg Ala Phe Leu
705                 710                 715                 720

Gly Gly Leu Pro Met Pro Ser Phe Gly Ser Ile Thr Asp Met Leu Lys
            725                 730                 735

Asp Ile Pro Leu Ile Leu Asn Ala Gln Leu Ser Tyr Ser Tyr Thr Lys
            740                 745                 750

Asn Asp Met Asp Thr Arg Tyr Thr Ser Tyr Pro Glu Ala Gln Gly Ser
        755                 760                 765

Trp Thr Asn Asn Ser Gly Ala Leu Glu Leu Gly Gly Ser Leu Ala Leu
    770                 775                 780

Tyr Leu Pro Lys Glu Ala Pro Phe Phe Gln Gly Tyr Phe Pro Phe Leu
785                 790                 795                 800

Lys Phe Gln Ala Val Tyr Ser Arg Gln Gln Asn Phe Lys Glu Ser Gly
            805                 810                 815

Ala Glu Ala Arg Ala Phe Asp Asp Gly Asp Leu Val Asn Cys Ser Ile
            820                 825                 830

Pro Val Gly Ile Arg Leu Glu Lys Ile Ser Glu Asp Glu Lys Asn Asn
        835                 840                 845

Phe Glu Ile Ser Leu Ala Asn Ile Gly Asp Val Tyr Arg Lys Asn Pro
    850                 855                 860

Arg Ser Arg Thr Ser Leu Met Val Ser Gly Ala Ser Trp Thr Ser Leu
865                 870                 875                 880

Cys Lys Asn Leu Ala Arg Gln Ala Phe Leu Ala Ser Ala Gly Ser His
            885                 890                 895

Leu Thr Leu Ser Pro His Val Glu Leu Ser Gly Glu Ala Ala Tyr Glu
            900                 905                 910

Leu Arg Gly Ser Ala His Ile Tyr Asn Val Asp Cys Gly Leu Arg Tyr
```

(2) INFORMATION FOR SEQ ID NO: 17:

(i) SEQUENCE CHARACTERISTICS:
(A) LENGTH: 840 base pairs
(B) TYPE: nucleic acid
(C) STRANDEDNESS: single
(D) TOPOLOGY: linear (ii) MOLECULE TYPE: Genomic DNA (xi) SEQUENCE DESCRIPTION: SEQ ID NO: 17:

```
GAAGACAATA TAAGGTACCG TCATAACAGC GGGGGTTATG CACTAGGGAT CACAGCAACA    60
ACTCCTGCCG AGGATCAGCT TACTTTTGCC TTCTGCCAGC TCTTTGCTAG AGATCGCAAT   120
CATATTACAG GTAAGAACCA CGGAGATACT TACGGTGCCT CTTTGTATTT CCACCATACA   180
GAAGGGCTCT TCGACATCGC CAATTTCCTC TGGGGAAAAG CAACCCGAGC TCCCTGGGTG   240
CTCTCTGAGA TCTCCCAGAT CATTCCTTTA TCGTTCGATG CTAAATTCAG TTATCTCCAT   300
ACAGACAACC ACATGAAGAC ATATTATACC GATAACTCTA TCATCAAGGG TTCTTGGAGA   360
AACGATGCCT TCTGTGCAGA TCTTGGAGCT AGCCTGCCTT TTGTTATTTC CGTTCCGTAT   420
CTTCTGAAAG AAGTCGAACC TTTTGTCAAA GTACAGTATA TCTATGCGCA TCAGCAAGAC   480
TTCTACGAGC GTCATGCTGA AGGACGCGCT TTCAATAAAA GCGAGCTTAT CAACGTAGAG   540
ATTCCTATAG GCGTCACCTT CGAAAGAGAC TCAAAATCAG AAAAGGGAAC TTACGATCTT   600
ACTCTTATGT ATATACTCGA TGCTTACCGA CGCAATCCTA AATGTCAAAC TTCCCTAATA   660
GCTAGCGATG CTAACTGGAT GGCCTATGGT ACCAACCTCG CACGACAAGG TTTTTCTGTT   720
CGTGCTGCGA ACCATTTCCA AGTGAACCCC CACATGGAAA TCTTCGGTCA ATTCGCTTTT   780
GAAGTACGAA GTTCTTCACG AAATTATAAT ACAAACCTAG GCTCTAAGTT TTGTTTCTAG   840
```

(2) INFORMATION FOR SEQ ID NO: 18:

(i) SEQUENCE CHARACTERISTICS:
(A) LENGTH: 279 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 18:

```
Glu Asp Asn Ile Arg Tyr Arg His Asn Ser Gly Gly Tyr Ala Leu Gly
  1               5                  10                  15
Ile Thr Ala Thr Thr Pro Ala Glu Asp Gln Leu Thr Phe Ala Phe Cys
                 20                  25                  30
Gln Leu Phe Ala Arg Asp Arg Asn His Ile Thr Gly Lys Asn His Gly
             35                  40                  45
Asp Thr Tyr Gly Ala Ser Leu Tyr Phe His His Thr Glu Gly Leu Phe
         50                  55                  60
Asp Ile Ala Asn Phe Leu Trp Gly Lys Ala Thr Arg Ala Pro Trp Val
 65                  70                  75                  80
Leu Ser Glu Ile Ser Gln Ile Ile Pro Leu Ser Phe Asp Ala Lys Phe
                 85                  90                  95
Ser Tyr Leu His Thr Asp Asn His Met Lys Thr Tyr Tyr Thr Asp Asn
            100                 105                 110
```

Ser Ile Ile Lys Gly Ser Trp Arg Asn Asp Ala Phe Cys Ala Asp Leu
        115                 120                 125

Gly Ala Ser Leu Pro Phe Val Ile Ser Val Pro Tyr Leu Leu Lys Glu
130                 135                 140

Val Glu Pro Phe Val Lys Val Gln Tyr Ile Tyr Ala His Gln Gln Asp
145                 150                 155                 160

Phe Tyr Glu Arg His Ala Glu Gly Arg Ala Phe Asn Lys Ser Glu Leu
            165                 170                 175

Ile Asn Val Glu Ile Pro Ile Gly Val Thr Phe Glu Arg Asp Ser Lys
        180                 185                 190

Ser Glu Lys Gly Thr Tyr Asp Leu Thr Leu Met Tyr Ile Leu Asp Ala
        195                 200                 205

Tyr Arg Arg Asn Pro Lys Cys Gln Thr Ser Leu Ile Ala Ser Asp Ala
210                 215                 220

Asn Trp Met Ala Tyr Gly Thr Asn Leu Ala Arg Gln Gly Phe Ser Val
225                 230                 235                 240

Arg Ala Ala Asn His Phe Gln Val Asn Pro His Met Glu Ile Phe Gly
            245                 250                 255

Gln Phe Ala Phe Glu Val Arg Ser Ser Ser Arg Asn Tyr Asn Thr Asn
            260                 265                 270

Leu Gly Ser Lys Phe Cys Phe
        275

(2) INFORMATION FOR SEQ ID NO: 19:

(i) SEQUENCE CHARACTERISTICS:
        (A) LENGTH: 1545 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 19:

| | |
|---|---|
| ATGACCATAC TTCGAAATTT TCTTACCTGC TCGGCTTTAT TCCTCGCTCT CCCTGCAGCA | 60 |
| GCACAAGTTG TATATCTTCA TGAAAGTGAT GGTTATAACG GTGCTATCAA TAATAAAAGC | 120 |
| TTAGAACCTA AAATTACCTG TTATCCAGAA GGAACTTCTT ACATCTTTCT AGATGACGTG | 180 |
| AGGATTTCCA ACGTTAAGCA TGATCAAGAA GATGCTGGGG TTTTTATAAA TCGATCTGGG | 240 |
| AATCTTTTTT TCATGGGCAA CCGTTGCAAC TTCACTTTTC ACAACCTTAT GACCGAGGGT | 300 |
| TTTGGCGCTG CCATTTCGAA CCGCGTTGGA GACACCACTC TCACTCTCTC TAATTTTTCT | 360 |
| TACTTAACGT TCACCTCAGC ACCTCTACTA CCTCAAGGAC AAGGAGCGAT TTATAGTCTT | 420 |
| GGTTCCGTGA TGATCGAAAA TAGTGAGGAA GTGACTTTCT GTGGGAACTA CTCTTCGTGG | 480 |
| AGTGGAGCTG CGATTTATAC TCCCTACCTT TTAGGTTCTA AGGCGAGTCG TCCTTCAGTA | 540 |
| AATCTCAGCG GGAACCGCTA CCTGGTGTTT AGAGACTATG TGAGCCAAGG TTATGGCGGC | 600 |
| GCCGTATCTA CCCACAATCT CACACTCACG ACTCGAGGAC CTTCGTGTTT TGAAAATAAT | 660 |
| CATGCTTATC ATGACGTGAA TAGTAATGGA GGAGCCATTG CCATTGCTCC TGGAGGATCG | 720 |
| ATCTCTATAT CCGTGAAAAG CGGAGATCTC ATCTTCAAAG GAAATACAGC ATCACAAGAC | 780 |
| GGAAATACAA TACACAACTC CATCCATCTG CAATCTGGAG CACAGTTTAA GAACCTACGT | 840 |
| GCTGTTTCAG AATCCGGAGT TTATTTCTAT GATCCTATAA GCCATAGCGA GTCGCATAAA | 900 |
| ATTACAGATC TTGTAATCAA TGCTCCTGAA GGAAAGGAAA CTTATGAAGG AACAATTAGC | 960 |

-continued

```
TTCTCAGGAC TATGCCTGGA TGATCATGAA GTTTGTGCGG AAAATCTTAC TTCCACAATC    1020

CTACAAGATG TCACATTAGC AGGAGGAACT CTCTCTCTAT CGGATGGGGT TACCTTGCAA    1080

CTGCATTCTT TTAAGCAGGA AGCAAGCTCT ACGCTTACTA TGTCTCCAGG AACCACTCTG    1140

CTCTGCTCAG GAGATGCTCG GGTTCAGAAT CTGCACATCC TGATTGAAGA TACCGACAAC    1200

TTTGTTCCTG TAAGGATTCG CGCCGAGGAC AAGGATGCTC TTGTCTCATT AGAAAAACTT    1260

AAAGTTGCCT TTGAGGCTTA TTGGTCCGTC TATGACTTTC CTCAATTTAA GGAAGCCTTT    1320

ACGATTCCTC TTCTTGAACT TCTAGGGCCT TCTTTTGACA GTCTTCTCCT AGGGGAGACC    1380

ACTTTGGAGA GAACCCAAGT CACAACAGAG AATGACGCCG TTCGAGGTTT CTGGTCCCTA    1440

AGCTGGGAAG AGTACCCCCC TTCTCTGGAT AAAGACAGAA GGATCACACC AACTAAGAAA    1500

ACTGTTTTCC TCACTTGGAA TCCTGAGATC ACTTCTACGC CATAA                    1545
```

(2) INFORMATION FOR SEQ ID NO: 20:

(i) SEQUENCE CHARACTERISTICS:
        (A) LENGTH: 514 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 20:

```
Met Thr Ile Leu Arg Asn Phe Leu Thr Cys Ser Ala Leu Phe Leu Ala
 1               5                  10                  15

Leu Pro Ala Ala Ala Gln Val Val Tyr Leu His Glu Ser Asp Gly Tyr
            20                  25                  30

Asn Gly Ala Ile Asn Asn Lys Ser Leu Glu Pro Lys Ile Thr Cys Tyr
        35                  40                  45

Pro Glu Gly Thr Ser Tyr Ile Phe Leu Asp Asp Val Arg Ile Ser Asn
    50                  55                  60

Val Lys His Asp Gln Glu Asp Ala Gly Val Phe Ile Asn Arg Ser Gly
65                  70                  75                  80

Asn Leu Phe Phe Met Gly Asn Arg Cys Asn Phe Thr Phe His Asn Leu
                85                  90                  95

Met Thr Glu Gly Phe Gly Ala Ala Ile Ser Asn Arg Val Gly Asp Thr
            100                 105                 110

Thr Leu Thr Leu Ser Asn Phe Ser Tyr Leu Thr Phe Thr Ser Ala Pro
        115                 120                 125

Leu Leu Pro Gln Gly Gln Gly Ala Ile Tyr Ser Leu Gly Ser Val Met
    130                 135                 140

Ile Glu Asn Ser Glu Glu Val Thr Phe Cys Gly Asn Tyr Ser Ser Trp
145                 150                 155                 160

Ser Gly Ala Ala Ile Tyr Thr Pro Tyr Leu Leu Gly Ser Lys Ala Ser
                165                 170                 175

Arg Pro Ser Val Asn Leu Ser Gly Asn Arg Tyr Leu Val Phe Arg Asp
            180                 185                 190

Tyr Val Ser Gln Gly Tyr Gly Gly Ala Val Ser Thr His Asn Leu Thr
        195                 200                 205

Leu Thr Thr Arg Gly Pro Ser Cys Phe Glu Asn Asn His Ala Tyr His
    210                 215                 220

Asp Val Asn Ser Asn Gly Gly Ala Ile Ala Ile Ala Pro Gly Gly Ser
225                 230                 235                 240

Ile Ser Ile Ser Val Lys Ser Gly Asp Leu Ile Phe Lys Gly Asn Thr
```

```
                    245                 250                 255
Ala Ser Gln Asp Gly Asn Thr Ile His Asn Ser Ile His Leu Gln Ser
            260                 265                 270

Gly Ala Gln Phe Lys Asn Leu Arg Ala Val Ser Glu Ser Gly Val Tyr
            275                 280                 285

Phe Tyr Asp Pro Ile Ser His Ser Glu Ser His Lys Ile Thr Asp Leu
            290                 295                 300

Val Ile Asn Ala Pro Glu Gly Lys Glu Thr Tyr Glu Gly Thr Ile Ser
305                 310                 315                 320

Phe Ser Gly Leu Cys Leu Asp Asp His Glu Val Cys Ala Glu Asn Leu
                325                 330                 335

Thr Ser Thr Ile Leu Gln Asp Val Thr Leu Ala Gly Gly Thr Leu Ser
            340                 345                 350

Leu Ser Asp Gly Val Thr Leu Gln Leu His Ser Phe Lys Gln Glu Ala
            355                 360                 365

Ser Ser Thr Leu Thr Met Ser Pro Gly Thr Thr Leu Leu Cys Ser Gly
            370                 375                 380

Asp Ala Arg Val Gln Asn Leu His Ile Leu Ile Glu Asp Thr Asp Asn
385                 390                 395                 400

Phe Val Pro Val Arg Ile Arg Ala Glu Asp Lys Asp Ala Leu Val Ser
                405                 410                 415

Leu Glu Lys Leu Lys Val Ala Phe Glu Ala Tyr Trp Ser Val Tyr Asp
            420                 425                 430

Phe Pro Gln Phe Lys Glu Ala Phe Thr Ile Pro Leu Leu Glu Leu Leu
            435                 440                 445

Gly Pro Ser Phe Asp Ser Leu Leu Leu Gly Glu Thr Thr Leu Glu Arg
450                 455                 460

Thr Gln Val Thr Thr Glu Asn Asp Ala Val Arg Gly Phe Trp Ser Leu
465                 470                 475                 480

Ser Trp Glu Glu Tyr Pro Pro Ser Leu Asp Lys Asp Arg Arg Ile Thr
                485                 490                 495

Pro Thr Lys Lys Thr Val Phe Leu Thr Trp Asn Pro Glu Ile Thr Ser
            500                 505                 510

Thr Pro (2) INFORMATION FOR SEQ ID NO: 21:

(i) SEQUENCE CHARACTERISTICS:
        (A) LENGTH: 787 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 21:

ATGAAAACGT CTATTCGTAA GTTCTTAATT TCTACCACAC TGGCGCCATG TTTTGCTTCA    60

ACAGCGTTTA CTGTAGAAGT TATCATGCCT TCCGAGAACT TGATGGATC GAGTGGGAAG   120

ATTTTTCCTT ACACAACACT TTCTGATCCT AGAGGGACAC TCTGTATTTT TTCAGGGGAT   180

CTCTACATTG CGAATCTTGA TAATGCCATA TCCAGAACCT CTTCCAGTTG CTTTAGCAAT   240

AGGGCGGGAG CACTACAAAT CTTAGGAAAA GGTGGGGTTT TCTCCTTCTT AAATATCCGT   300

TCTTCAGCTG ACGGAGCCGC GATTAGTAGT GTAATCACCC AAAATCCTGA ACTATGTCCC   360

TTGAGTTTTT CAGGATTTAG TCAGATGATC TTCGATAACT GTGAATCTTT GACTTCAGAT   420
```

```
ACCTCAGCGA GTAATGTCAT ACCTCACGCA TCGGCGATTT ACGCTACAAC GCCCATGCTC      480

TTTACAAACA ATGACTCCAT ACTATTCCAA TACAACCGTT CTGCAGGATT TGGAGCTGCC      540

ATTCGAGGCA CAAGCATCAC AATAGAAAAT ACGAAAAAGA GCCTTCTCTT TAATGGTAAT      600

GGATCCATCT CTAATGGAGG GGCCCTCACG GGATCTGCAG CGATCAACCT CATCAACAAT      660

AGCGCTCCTG TGATTTTCTC AACGAATGCT ACAGGGATCT ATGGTGGGGC TATTTACCTT      720

ACCGGAGGAT CTATGCTCAC CTCTGGGAAC CTCTCAGGAG TCTTGTTCGT TTATAATAGC      780

TCGCGCT                                                                787
```

(2) INFORMATION FOR SEQ ID NO: 22:

(i) SEQUENCE CHARACTERISTICS:
        (A) LENGTH: 262 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 22:

```
Met Lys Thr Ser Ile Arg Lys Phe Leu Ile Ser Thr Thr Leu Ala Pro
  1               5                  10                  15

Cys Phe Ala Ser Thr Ala Phe Thr Val Glu Val Ile Met Pro Ser Glu
                 20                  25                  30

Asn Phe Asp Gly Ser Ser Gly Lys Ile Phe Pro Tyr Thr Thr Leu Ser
             35                  40                  45

Asp Pro Arg Gly Thr Leu Cys Ile Phe Ser Gly Asp Leu Tyr Ile Ala
         50                  55                  60

Asn Leu Asp Asn Ala Ile Ser Arg Thr Ser Ser Ser Cys Phe Ser Asn
 65                  70                  75                  80

Arg Ala Gly Ala Leu Gln Ile Leu Gly Lys Gly Gly Val Phe Ser Phe
                 85                  90                  95

Leu Asn Ile Arg Ser Ser Ala Asp Gly Ala Ala Ile Ser Ser Val Ile
                100                 105                 110

Thr Gln Asn Pro Glu Leu Cys Pro Leu Ser Phe Ser Gly Phe Ser Gln
            115                 120                 125

Met Ile Phe Asp Asn Cys Glu Ser Leu Thr Ser Asp Thr Ser Ala Ser
        130                 135                 140

Asn Val Ile Pro His Ala Ser Ala Ile Tyr Ala Thr Thr Pro Met Leu
145                 150                 155                 160

Phe Thr Asn Asn Asp Ser Ile Leu Phe Gln Tyr Asn Arg Ser Ala Gly
                165                 170                 175

Phe Gly Ala Ala Ile Arg Gly Thr Ser Ile Thr Ile Glu Asn Thr Lys
                180                 185                 190

Lys Ser Leu Leu Phe Asn Gly Asn Gly Ser Ile Ser Asn Gly Gly Ala
            195                 200                 205

Leu Thr Gly Ser Ala Ala Ile Asn Leu Ile Asn Asn Ser Ala Pro Val
        210                 215                 220

Ile Phe Ser Thr Asn Ala Thr Gly Ile Tyr Gly Ala Ile Tyr Leu
225                 230                 235                 240

Thr Gly Gly Ser Met Leu Thr Ser Gly Asn Leu Ser Gly Val Leu Phe
                245                 250                 255

Val Tyr Asn Ser Ser Arg
            260
```

(2) INFORMATION FOR SEQ ID NO: 23:

(i) SEQUENCE CHARACTERISTICS:
        (A) LENGTH: 2838 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 23:

```
ATGAAGACTT CAGTTTCTAT GTTGTTGGCC CTGCTTTGCT CGGGGGCTAG CTCTATTGTA      60
CTCCATGCCG CAACCACTCC ACTAAATCCT GAAGATGGGT TTATTGGGGA GGGCAATACA     120
AATACTTTTT CTCCGAAATC TACAACGGAT GCTGCAGGAA CTACCTACTC TCTCACAGGA     180
GAGGTTCTGT TTATAGATCC GGGGAAAGGT GGTTCAATTA CAGGAACTTG CTTTGTAGAA     240
ACTGCTGGCG ATCTTACATT TTTAGGTAAT GGAAATACCC TAAAGTTCCT GTCGGTAGAT     300
GCAGGTGCTA ATATCGCGGT TGCTCATGTA CAAGGAAGTA AGAATTTAAG CTTCACAGAT     360
TTCCTTTCTC TGGTGATCAC AGAATCTCCA AAATCCGCTG TTAGTACAGG AAAAGGTAGC     420
CTAGTCAGTT CAGGTGCAGT CCAACTGCAA GATATAAACA CTCTAGTTCT TACAAGCAAT     480
GCCTCTGTCG AAGATGGTGG CGTGATTAAA GGAAACTCCT GCTTGATTCA GGGAATCAAA     540
AATAGTGCGA TTTTTGGACA AAATACATCT TCGAAAAAAG GAGGGCGAT CTCCACGACT      600
CAAGGACTCA CCATAGAGAA TAACTTAGGG ACGCTAAAGT TCAATGAAAA CAAAGCAGTG     660
ACCTCAGGAG GCGCCTTAGA TTTAGGAGCC GCGTCTACAT TCACTGCGAA CCATGAGTTG     720
ATATTTTCAC AAAATAAGAC TTCTGGGAAT GCTGCAAATG GCGGAGCCAT AAATTGCTCA     780
GGCGACCTAA CATTTACTGA TAACACTTCT TTGTTACTTC AAGAAAATAG CACAATGCAG     840
GATGGTGGAG CTTTGTGTAG CACAGGAACC ATAAGCATTA CCGGTAGTGA TTCTATCAAT     900
GTGATAGGAA ATACTTCAGG ACAAAAAGGA GGAGCGATTT CTGCAGCTTC TCTCAAGATT     960
TTGGGAGGGC AGGGAGGCGC TCTCTTTTCT AATAACGTAG TGACTCATGC CACCCCTCTA    1020
GGAGGTGCCA TTTTTATCAA CACAGGAGGA TCCTTGCAGC TCTTCACTCA AGGAGGGGAT    1080
ATCGTATTCG AGGGGAATCA GGTCACTACA ACAGCTCCAA ATGCTACCAC TAAGAGAAAT    1140
GTAATTCACC TCGAGAGCAC CGCGAAGTGG ACGGGACTTG CTGCAAGTCA AGGTAACGCT    1200
ATCTATTTCT ATGATCCCAT TACCACCAAC GATACGGGAG CAAGCGATAA CTTACGTATC    1260
AATGAGGTCA GTGCAAATCA AAAGCTCTCG GGATCTATAG TATTTTCTGG AGAGAGATTG    1320
TCGACAGCAG AAGCTATAGC TGAAAATCTT ACTTCGAGGA TCAACCAGCC TGTCACTTTA    1380
GTAGAGGGA GCTTAGAACT TAAACAGGGA GTGACCTTGA TCACACAAGG ATTCTCGCAG     1440
GAGCCAGAAT CCACGCTTCT TTTGGATTTG GGGACCTCAT TACAAGCTTC TACAGAAGAT    1500
ATCGTCATCA CAAATTCATC TATAAATGCC GATACCATTT ACGGAAAGAA TCCAATCAAT    1560
ATTGTAGCTT CAGCAGCGAA TAAGAACATT ACCCTAACAG GAACCTTAGC ACTTGTAAAT    1620
GCAGATGGAG CTTTGTATGA GAACCATACC TTGCAAGACT CTCAAGATTA TAGCTTTGTA    1680
AAGTTATCTC CAGGAGCGGG AGGGACTATA ATTACTCAAG ATGCTTCTCA GAAGCTTCTT    1740
GAAGTAGCTC CTTCTAGACC ACATTATGGC TATCAAGGAC ATTGGAATGT GCAAGTCATC    1800
CCAGGAACGG GAACTCAACC GAGCCAGGCA AATTTAGAAT GGGTGCGGAC AGGATACCTT    1860
CCGAATCCCG AACGGCAAGG ATTTTTAGTT CCCAATAGCC TGTGGGGTTC TTTTGTTGAT    1920
CAGCGTGCTA TCCAAGAAAT CATGGTAAAT AGTAGCCAAA TCTTATGTCA GGAACGGGGA    1980
GTCTGGGGAG CTGGAATTGC TAATTTCCTA CATAGAGATA AAATTAATGA GCACGGCTAT    2040
```

```
CGCCATAGCG GTGTCGGTTA TCTTGTGGGA GTTGGCACTC ATGCTTTTTC TGATGCTACG    2100

ATAAATGCGG CTTTTTGCCA GCTCTTCAGT AGAGATAAAG ACTACGTAGT ATCCAAAAAT    2160

CATGGAACTA GCTACTCAGG GGTCGTATTT CTTGAGGATA CCCTAGAGTT TAGAAGTCCA    2220

CAGGGATTCT ATACTGATAG CTCCTCAGAA GCTTGCTGTA ACCAAGTCGT CACTATAGAT    2280

ATGCAGTTGT CTTACAGCCA TAGAAATAAT GATATGAAAA CCAAATACAC GACATATCCA    2340

GAAGCTCAGG GATCTTGGGC AAATGATGTT TTTGGTCTTG AGTTTGGAGC GACTACATAC    2400

TACTACCCTA ACAGTACTTT TTTATTTGAT TACTACTCTC CGTTTCTCAG GCTGCAGTGC    2460

ACCTATGCTC ACCAGGAAGA CTTCAAAGAG ACAGGAGGTG AGGTTCGTCA CTTTACTAGC    2520

GGAGATCTTT TCAATTTAGC AGTTCCTATT GGCGTGAAGT TTGAGAGATT TTCAGACTGT    2580

AAAAGGGGAT CTTATGAACT TACCCTTGCT TATGTTCCTG ATGTGATTCG CAAAGATCCC    2640

AAGAGCACGG CAACATTGGC TAGTGGAGCT ACGTGGAGCA CCCACGGAAA CAATCTCTCC    2700

AGACAAGGAT TACAACTGCG TTTAGGGAAC CACTGTCTCA TAAATCCTGG AATTGAGGTG    2760

TTCAGTCACG GAGCTATTGA ATTGCGGGGA TCCTCTCGTA ATTATAACAT CAATCTCGGG    2820

GGTAAATACC GATTTTAA                                                 2838
```

(2) INFORMATION FOR SEQ ID NO: 24:

(i) SEQUENCE CHARACTERISTICS:
        (A) LENGTH: 945 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 24:

```
Met Lys Thr Ser Val Ser Met Leu Leu Ala Leu Leu Cys Ser Gly Ala
 1               5                  10                  15

Ser Ser Ile Val Leu His Ala Ala Thr Thr Pro Leu Asn Pro Glu Asp
            20                  25                  30

Gly Phe Ile Gly Glu Gly Asn Thr Asn Thr Phe Ser Pro Lys Ser Thr
         35                  40                  45

Thr Asp Ala Ala Gly Thr Thr Tyr Ser Leu Thr Gly Glu Val Leu Phe
 50                  55                  60

Ile Asp Pro Gly Lys Gly Gly Ser Ile Thr Gly Thr Cys Phe Val Glu
 65                  70                  75                  80

Thr Ala Gly Asp Leu Thr Phe Leu Gly Asn Gly Asn Thr Leu Lys Phe
                 85                  90                  95

Leu Ser Val Asp Ala Gly Ala Asn Ile Ala Val Ala His Val Gln Gly
                100                 105                 110

Ser Lys Asn Leu Ser Phe Thr Asp Phe Leu Ser Leu Val Ile Thr Glu
            115                 120                 125

Ser Pro Lys Ser Ala Val Ser Thr Gly Lys Gly Ser Leu Val Ser Ser
        130                 135                 140

Gly Ala Val Gln Leu Gln Asp Ile Asn Thr Leu Val Leu Thr Ser Asn
145                 150                 155                 160

Ala Ser Val Glu Asp Gly Gly Val Ile Lys Gly Asn Ser Cys Leu Ile
                165                 170                 175

Gln Gly Ile Lys Asn Ser Ala Ile Phe Gly Gln Asn Thr Ser Ser Lys
            180                 185                 190

Lys Gly Gly Ala Ile Ser Thr Thr Gln Gly Leu Thr Ile Glu Asn Asn
```

```
                195                 200                 205
Leu Gly Thr Leu Lys Phe Asn Glu Asn Lys Ala Val Thr Ser Gly Gly
    210                 215                 220

Ala Leu Asp Leu Gly Ala Ala Ser Thr Phe Thr Ala Asn His Glu Leu
225                 230                 235                 240

Ile Phe Ser Gln Asn Lys Thr Ser Gly Asn Ala Ala Asn Gly Gly Ala
                245                 250                 255

Ile Asn Cys Ser Gly Asp Leu Thr Phe Thr Asp Asn Thr Ser Leu Leu
            260                 265                 270

Leu Gln Glu Asn Ser Thr Met Gln Asp Gly Gly Ala Leu Cys Ser Thr
        275                 280                 285

Gly Thr Ile Ser Ile Thr Gly Ser Asp Ser Ile Asn Val Ile Gly Asn
    290                 295                 300

Thr Ser Gly Gln Lys Gly Gly Ala Ile Ser Ala Ala Ser Leu Lys Ile
305                 310                 315                 320

Leu Gly Gly Gln Gly Gly Ala Leu Phe Ser Asn Asn Val Val Thr His
                325                 330                 335

Ala Thr Pro Leu Gly Gly Ala Ile Phe Ile Asn Thr Gly Gly Ser Leu
            340                 345                 350

Gln Leu Phe Thr Gln Gly Gly Asp Ile Val Phe Glu Gly Asn Gln Val
        355                 360                 365

Thr Thr Thr Ala Pro Asn Ala Thr Lys Arg Asn Val Ile His Leu
    370                 375                 380

Glu Ser Thr Ala Lys Trp Thr Gly Leu Ala Ala Ser Gln Gly Asn Ala
385                 390                 395                 400

Ile Tyr Phe Tyr Asp Pro Ile Thr Thr Asn Asp Thr Gly Ala Ser Asp
                405                 410                 415

Asn Leu Arg Ile Asn Glu Val Ser Ala Asn Gln Lys Leu Ser Gly Ser
            420                 425                 430

Ile Val Phe Ser Gly Glu Arg Leu Ser Thr Ala Glu Ala Ile Ala Glu
        435                 440                 445

Asn Leu Thr Ser Arg Ile Asn Gln Pro Val Thr Leu Val Glu Gly Ser
    450                 455                 460

Leu Glu Leu Lys Gln Gly Val Thr Leu Ile Thr Gln Gly Phe Ser Gln
465                 470                 475                 480

Glu Pro Glu Ser Thr Leu Leu Leu Asp Leu Gly Thr Ser Leu Gln Ala
                485                 490                 495

Ser Thr Glu Asp Ile Val Ile Thr Asn Ser Ser Ile Asn Ala Asp Thr
            500                 505                 510

Ile Tyr Gly Lys Asn Pro Ile Asn Ile Val Ala Ser Ala Ala Asn Lys
        515                 520                 525

Asn Ile Thr Leu Thr Gly Thr Leu Ala Leu Val Asn Ala Asp Gly Ala
    530                 535                 540

Leu Tyr Glu Asn His Thr Leu Gln Asp Ser Gln Asp Tyr Ser Phe Val
545                 550                 555                 560

Lys Leu Ser Pro Gly Ala Gly Thr Ile Ile Thr Gln Asp Ala Ser
                565                 570                 575

Gln Lys Leu Leu Glu Val Ala Pro Ser Arg Pro His Tyr Gly Tyr Gln
            580                 585                 590

Gly His Trp Asn Val Gln Val Ile Pro Gly Thr Gly Thr Gln Pro Ser
        595                 600                 605

Gln Ala Asn Leu Glu Trp Val Arg Thr Gly Tyr Leu Pro Asn Pro Glu
    610                 615                 620
```

```
Arg Gln Gly Phe Leu Val Pro Asn Ser Leu Trp Gly Ser Phe Val Asp
625                 630                 635                 640

Gln Arg Ala Ile Gln Glu Ile Met Val Asn Ser Ser Gln Ile Leu Cys
            645                 650                 655

Gln Glu Arg Gly Val Trp Gly Ala Gly Ile Ala Asn Phe Leu His Arg
        660                 665                 670

Asp Lys Ile Asn Glu His Gly Tyr Arg His Ser Gly Val Gly Tyr Leu
            675                 680                 685

Val Gly Val Gly Thr His Ala Phe Ser Asp Ala Thr Ile Asn Ala Ala
690                 695                 700

Phe Cys Gln Leu Phe Ser Arg Asp Lys Asp Tyr Val Val Ser Lys Asn
705                 710                 715                 720

His Gly Thr Ser Tyr Ser Gly Val Val Phe Leu Glu Asp Thr Leu Glu
                725                 730                 735

Phe Arg Ser Pro Gln Gly Phe Tyr Thr Asp Ser Ser Ser Glu Ala Cys
            740                 745                 750

Cys Asn Gln Val Val Thr Ile Asp Met Gln Leu Ser Tyr Ser His Arg
        755                 760                 765

Asn Asn Asp Met Lys Thr Lys Tyr Thr Thr Tyr Pro Glu Ala Gln Gly
770                 775                 780

Ser Trp Ala Asn Asp Val Phe Gly Leu Glu Phe Gly Ala Thr Thr Tyr
785                 790                 795                 800

Tyr Tyr Pro Asn Ser Thr Phe Leu Phe Asp Tyr Tyr Ser Pro Phe Leu
                805                 810                 815

Arg Leu Gln Cys Thr Tyr Ala His Gln Glu Asp Phe Lys Glu Thr Gly
            820                 825                 830

Gly Glu Val Arg His Phe Thr Ser Gly Asp Leu Phe Asn Leu Ala Val
        835                 840                 845

Pro Ile Gly Val Lys Phe Glu Arg Phe Ser Asp Cys Lys Arg Gly Ser
850                 855                 860

Tyr Glu Leu Thr Leu Ala Tyr Val Pro Asp Val Ile Arg Lys Asp Pro
865                 870                 875                 880

Lys Ser Thr Ala Thr Leu Ala Ser Gly Ala Thr Trp Ser Thr His Gly
                885                 890                 895

Asn Asn Leu Ser Arg Gln Gly Leu Gln Leu Arg Leu Gly Asn His Cys
            900                 905                 910

Leu Ile Asn Pro Gly Ile Glu Val Phe Ser His Gly Ala Ile Glu Leu
        915                 920                 925

Arg Gly Ser Ser Arg Asn Tyr Asn Ile Asn Leu Gly Gly Lys Tyr Arg
930                 935                 940

Phe
945

(2) INFORMATION FOR SEQ ID NO: 25:

(i) SEQUENCE CHARACTERISTICS:
        (A) LENGTH: 3000 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 259...3000
        (D) OTHER INFORMATION:
```

(xi) SEQUENCE DESCRIPTION: SEQ ID NO: 25:

```
ATCAGGTGAT AAAAGTTCCT CGTTAGCTAG TGACTGTAGG TGACATGAGA AAGCTAACAC          60

GGAGGAAACT AAAACCCAAG GAATCGAAGT CTTCATGGTA ATGCTTTTGT TTTTTAGAGA         120

ACTATTCGCA TCAATATAGA AACAAAATAA GTAAATCAAG TTAAAGATGA CAAAACAGCT         180

GTCAAGAATT TTTATCTTGA CTCTCTGAGT TTTCTATTTT ATATGACGCA AGTAAGAATT         240

TAATAATAAA GTGGGTTT ATG AAA TCG CAA TTT TCC TGG TTA GTG CTC TCT           291
                     Met Lys Ser Gln Phe Ser Trp Leu Val Leu Ser
                       1               5                      10

TCG ACA TTG GCA TGT TTT ACT AGT TGT TCC ACT GTT TTT GCT GCA ACT           339
Ser Thr Leu Ala Cys Phe Thr Ser Cys Ser Thr Val Phe Ala Ala Thr
                15                  20                  25

GCT GAA AAT ATA GGC CCC TCT GAT AGC TTT GAC GGA AGT ACT AAC ACA           387
Ala Glu Asn Ile Gly Pro Ser Asp Ser Phe Asp Gly Ser Thr Asn Thr
            30                  35                  40

GGC ACC TAT ACT CCT AAA AAT ACG ACT ACT GGA ATA GAC TAT ACT CTG           435
Gly Thr Tyr Thr Pro Lys Asn Thr Thr Thr Gly Ile Asp Tyr Thr Leu
        45                  50                  55

ACA GGA GAT ATA ACT CTG CAA AAC CTT GGG GAT TCG GCA GCT TTA ACG           483
Thr Gly Asp Ile Thr Leu Gln Asn Leu Gly Asp Ser Ala Ala Leu Thr
 60              65                  70                      75

AAG GGT TGT TTT TCT GAC ACT ACG GAA TCT TTA AGC TTT GCC GGT AAG           531
Lys Gly Cys Phe Ser Asp Thr Thr Glu Ser Leu Ser Phe Ala Gly Lys
                80                  85                  90

GGG TAC TCA CTT TCT TTT TTA AAT ATT AAG TCT AGT GCT GAA GGC GCA           579
Gly Tyr Ser Leu Ser Phe Leu Asn Ile Lys Ser Ser Ala Glu Gly Ala
            95                  100                 105

GCA CTT TCT GTT ACA ACT GAT AAA AAT CTG TCG CTA ACA GGA TTT TCG           627
Ala Leu Ser Val Thr Thr Asp Lys Asn Leu Ser Leu Thr Gly Phe Ser
        110                 115                 120

AGT CTT ACT TTC TTA GCG GCC CCA TCA TCG GTA ATC ACA ACC CCC TCA           675
Ser Leu Thr Phe Leu Ala Ala Pro Ser Ser Val Ile Thr Thr Pro Ser
    125                 130                 135

GGA AAA GGT GCA GTT AAA TGT GGA GGG GAT CTT ACA TTT GAT AAC AAT           723
Gly Lys Gly Ala Val Lys Cys Gly Gly Asp Leu Thr Phe Asp Asn Asn
140                 145                 150                 155

GGA ACT ATT TTA TTT AAA CAA GAT TAC TGT GAG GAA AAT GGC GGA GCC           771
Gly Thr Ile Leu Phe Lys Gln Asp Tyr Cys Glu Glu Asn Gly Gly Ala
                160                 165                 170

ATT TCT ACC AAG AAT CTT TCT TTG AAA AAC AGC ACG GGA TCG ATT TCT           819
Ile Ser Thr Lys Asn Leu Ser Leu Lys Asn Ser Thr Gly Ser Ile Ser
            175                 180                 185

TTT GAA GGG AAT AAA TCG AGC GCA ACA GGG AAA AAA GGT GGG GCT ATT           867
Phe Glu Gly Asn Lys Ser Ser Ala Thr Gly Lys Lys Gly Gly Ala Ile
        190                 195                 200

TGT GCT ACT GGT ACT GTA GAT ATT ACA AAT AAT ACG GCT CCT ACC CTC           915
Cys Ala Thr Gly Thr Val Asp Ile Thr Asn Asn Thr Ala Pro Thr Leu
    205                 210                 215

TTC TCG AAC AAT ATT GCT GAA GCT GCA GGT GGA GCT ATA AAT AGC ACA           963
Phe Ser Asn Asn Ile Ala Glu Ala Ala Gly Gly Ala Ile Asn Ser Thr
220                 225                 230                 235

GGA AAC TGT ACA ATT ACA GGG AAT ACG TCT CTT GTA TTT TCT GAA AAT          1011
Gly Asn Cys Thr Ile Thr Gly Asn Thr Ser Leu Val Phe Ser Glu Asn
                240                 245                 250

AGT GTG ACA GCG ACC GCA GGA AAT GGA GGA GCT CTT TCT GGA GAT GCC          1059
Ser Val Thr Ala Thr Ala Gly Asn Gly Gly Ala Leu Ser Gly Asp Ala
            255                 260                 265
```

```
GAT GTT ACC ATA TCT GGG AAT CAG AGT GTA ACT TTC TCA GGA AAC CAA      1107
Asp Val Thr Ile Ser Gly Asn Gln Ser Val Thr Phe Ser Gly Asn Gln
            270                 275                 280

GCT GTA GCT AAT GGC GGA GCC ATT TAT GCT AAG AAG CTT ACA CTG GCT      1155
Ala Val Ala Asn Gly Gly Ala Ile Tyr Ala Lys Lys Leu Thr Leu Ala
        285                 290                 295

TCC GGG GGG GGG GGG GGT ATC TCC TTT TCT AAC AAT ATA GTC CAA GGT      1203
Ser Gly Gly Gly Gly Gly Ile Ser Phe Ser Asn Asn Ile Val Gln Gly
300                 305                 310                 315

ACC ACT GCA GGT AAT GGT GGA GCC ATT TCT ATA CTG GCA GCT GGA GAG      1251
Thr Thr Ala Gly Asn Gly Gly Ala Ile Ser Ile Leu Ala Ala Gly Glu
            320                 325                 330

TGT AGT CTT TCA GCA GAA GCA GGG GAC ATT ACC TTC AAT GGG AAT GCC      1299
Cys Ser Leu Ser Ala Glu Ala Gly Asp Ile Thr Phe Asn Gly Asn Ala
        335                 340                 345

ATT GTT GCA ACT ACA CCA CAA ACT ACA AAA AGA AAT TCT ATT GAC ATA      1347
Ile Val Ala Thr Thr Pro Gln Thr Thr Lys Arg Asn Ser Ile Asp Ile
            350                 355                 360

GGA TCT ACT GCA AAG ATC ACG AAT TTA CGT GCA ATA TCT GGG CAT AGC      1395
Gly Ser Thr Ala Lys Ile Thr Asn Leu Arg Ala Ile Ser Gly His Ser
        365                 370                 375

ATC TTT TTC TAC GAT CCG ATT ACT GCT AAT ACG GCT GCG GAT TCT ACA      1443
Ile Phe Phe Tyr Asp Pro Ile Thr Ala Asn Thr Ala Ala Asp Ser Thr
380                 385                 390                 395

GAT ACT TTA AAT CTC AAT AAG GCT GAT GCA GGT AAT AGT ACA GAT TAT      1491
Asp Thr Leu Asn Leu Asn Lys Ala Asp Ala Gly Asn Ser Thr Asp Tyr
            400                 405                 410

AGT GGG TCG ATT GTT TTT TCT GGT GAA AAG CTC TCT GAA GAT GAA GCA      1539
Ser Gly Ser Ile Val Phe Ser Gly Glu Lys Leu Ser Glu Asp Glu Ala
        415                 420                 425

AAA GTT GCA GAC AAC CTC ACT TCT ACG CTG AAG CAG CCT GTA ACT CTA      1587
Lys Val Ala Asp Asn Leu Thr Ser Thr Leu Lys Gln Pro Val Thr Leu
            430                 435                 440

ACT GCA GGA AAT TTA GTA CTT AAA CGT GGT GTC ACT CTC GAT ACG AAA      1635
Thr Ala Gly Asn Leu Val Leu Lys Arg Gly Val Thr Leu Asp Thr Lys
        445                 450                 455

GGC TTT ACT CAG ACC GCG GGT TCC TCT GTT ATT ATG GAT GCG GGC ACA      1683
Gly Phe Thr Gln Thr Ala Gly Ser Ser Val Ile Met Asp Ala Gly Thr
460                 465                 470                 475

ACG TTA AAA GCA AGT ACA GAG GAG GTC ACT TTA ACA GGT CTT TCC ATT      1731
Thr Leu Lys Ala Ser Thr Glu Glu Val Thr Leu Thr Gly Leu Ser Ile
            480                 485                 490

CCT GTA GAC TCT TTA GGC GAG GGT AAG AAA GTT GTA ATT GCT GCT TCT      1779
Pro Val Asp Ser Leu Gly Glu Gly Lys Lys Val Val Ile Ala Ala Ser
        495                 500                 505

GCA GCA AGT AAA AAT GTA GCC CTT AGT GGT CCG ATT CTT CTT TTG GAT      1827
Ala Ala Ser Lys Asn Val Ala Leu Ser Gly Pro Ile Leu Leu Leu Asp
            510                 515                 520

AAC CAA GGG AAT GCT TAT GAA AAT CAC GAC TTA GGA AAA ACT CAA GAC      1875
Asn Gln Gly Asn Ala Tyr Glu Asn His Asp Leu Gly Lys Thr Gln Asp
        525                 530                 535

TTT TCA TTT GTG CAG CTC TCT GCT CTG GGT ACT GCA ACA ACT ACA GAT      1923
Phe Ser Phe Val Gln Leu Ser Ala Leu Gly Thr Ala Thr Thr Thr Asp
540                 545                 550                 555

GTT CCA GCG GTT CCT ACA GTA GCA ACT CCT ACG CAC TAT GGG TAT CAA      1971
Val Pro Ala Val Pro Thr Val Ala Thr Pro Thr His Tyr Gly Tyr Gln
            560                 565                 570

GGT ACT TGG GGA ATG ACT TGG GTT GAT GAT ACC GCA AGC ACT CCA AAG      2019
Gly Thr Trp Gly Met Thr Trp Val Asp Asp Thr Ala Ser Thr Pro Lys
        575                 580                 585
```

```
ACT AAG ACA GCG ACA TTA GCT TGG ACC AAT ACA GGC TAC CTT CCG AAT       2067
Thr Lys Thr Ala Thr Leu Ala Trp Thr Asn Thr Gly Tyr Leu Pro Asn
        590                 595                 600

CCT GAG CGT CAA GGA CCT TTA GTT CCT AAT AGC TTG TGG GGA TCT TTT       2115
Pro Glu Arg Gln Gly Pro Leu Val Pro Asn Ser Leu Trp Gly Ser Phe
        605                 610                 615

TCA GAC ATC CAA GCG ATT CAA GGT GTC ATA GAG AGA AGT GCT TTG ACT       2163
Ser Asp Ile Gln Ala Ile Gln Gly Val Ile Glu Arg Ser Ala Leu Thr
620                 625                 630                 635

CTT TGT TCA GAT CGA GGC TTC TGG GCT GCG GGA GTC GCC AAT TTC TTA       2211
Leu Cys Ser Asp Arg Gly Phe Trp Ala Ala Gly Val Ala Asn Phe Leu
                640                 645                 650

GAT AAA GAT AAG AAA GGG GAA AAA CGC AAA TAC CGT CAT AAA TCT GGT       2259
Asp Lys Asp Lys Lys Gly Glu Lys Arg Lys Tyr Arg His Lys Ser Gly
            655                 660                 665

GGA TAT GCT ATC GGA GGT GCA GCG CAA ACT TGT TCT GAA AAC TTA ATT       2307
Gly Tyr Ala Ile Gly Gly Ala Ala Gln Thr Cys Ser Glu Asn Leu Ile
        670                 675                 680

AGC TTT GCC TTT TGC CAA CTC TTT GGT AGC GAT AAA GAT TTC TTA GTC       2355
Ser Phe Ala Phe Cys Gln Leu Phe Gly Ser Asp Lys Asp Phe Leu Val
        685                 690                 695

GCT AAA AAT CAT ACT GAT ACC TAT GCA GGA GCC TTC TAT ATC CAA CAC       2403
Ala Lys Asn His Thr Asp Thr Tyr Ala Gly Ala Phe Tyr Ile Gln His
700                 705                 710                 715

ATT ACA GAA TGT AGT GGG TTC ATA GGT TGT CTC TTA GAT AAA CTT CCT       2451
Ile Thr Glu Cys Ser Gly Phe Ile Gly Cys Leu Leu Asp Lys Leu Pro
                720                 725                 730

GGC TCT TGG AGT CAT AAA CCC CTC GTT TTA GAA GGG CAG CTC GCT TAT       2499
Gly Ser Trp Ser His Lys Pro Leu Val Leu Glu Gly Gln Leu Ala Tyr
            735                 740                 745

AGC CAC GTC AGT AAT GAT CTG AAG ACA AAG TAT ACT GCG TAT CCT GAG       2547
Ser His Val Ser Asn Asp Leu Lys Thr Lys Tyr Thr Ala Tyr Pro Glu
        750                 755                 760

GTG AAA GGT TCT TGG GGG AAT AAT GCT TTT AAC ATG ATG TTG GGA GCT       2595
Val Lys Gly Ser Trp Gly Asn Asn Ala Phe Asn Met Met Leu Gly Ala
765                 770                 775

TCT TCT CAT TCT TAT CCT GAA TAC CTG CAT TGT TTT GAT ACC TAT GCT       2643
Ser Ser His Ser Tyr Pro Glu Tyr Leu His Cys Phe Asp Thr Tyr Ala
780                 785                 790                 795

CCA TAC ATC AAA CTG AAT CTG ACC TAT ATA CGT CAG GAC AGC TTC TCG       2691
Pro Tyr Ile Lys Leu Asn Leu Thr Tyr Ile Arg Gln Asp Ser Phe Ser
                800                 805                 810

GAG AAA GGT ACA GAA GGA AGA TCT TTT GAT GAC AGC AAC CTC TTC AAT       2739
Glu Lys Gly Thr Glu Gly Arg Ser Phe Asp Asp Ser Asn Leu Phe Asn
            815                 820                 825

TTA TCT TTG CCT ATA GGG GTG AAG TTT GAG AAG TTC TCT GAT TGT AAT       2787
Leu Ser Leu Pro Ile Gly Val Lys Phe Glu Lys Phe Ser Asp Cys Asn
        830                 835                 840

GAC TTT TCT TAT GAT CTG ACT TTA TCC TAT GTT CCT GAT CTT ATC CGC       2835
Asp Phe Ser Tyr Asp Leu Thr Leu Ser Tyr Val Pro Asp Leu Ile Arg
        845                 850                 855

AAT GAT CCC AAA TGC ACT ACA GCA CTT GTA ATC AGC GGA GCC TCT TGG       2883
Asn Asp Pro Lys Cys Thr Thr Ala Leu Val Ile Ser Gly Ala Ser Trp
860                 865                 870                 875

GAA ACT TAT GCC AAT AAC TTA GCA CGA CAG GCC TTG CAA GTG CGT GCA       2931
Glu Thr Tyr Ala Asn Asn Leu Ala Arg Gln Ala Leu Gln Val Arg Ala
                880                 885                 890

GGC AGT CAC TAC GCC TTC TCT CCT ATG TTT GAA GTG CTC GGC CAG TTT       2979
Gly Ser His Tyr Ala Phe Ser Pro Met Phe Glu Val Leu Gly Gln Phe
```

-continued

```
                895                 900                 905
GTC TTT GAA GTT CGT GGA TCC                                              3000
Val Phe Glu Val Arg Gly Ser
    910
```

(2) INFORMATION FOR SEQ ID NO: 26:

(i) SEQUENCE CHARACTERISTICS:
        (A) LENGTH: 914 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO: 26:

```
Met Lys Ser Gln Phe Ser Trp Leu Val Leu Ser Ser Thr Leu Ala Cys
 1               5                  10                  15

Phe Thr Ser Cys Ser Thr Val Phe Ala Ala Thr Ala Glu Asn Ile Gly
                20                  25                  30

Pro Ser Asp Ser Phe Asp Gly Ser Thr Asn Thr Gly Thr Tyr Thr Pro
            35                  40                  45

Lys Asn Thr Thr Thr Gly Ile Asp Tyr Thr Leu Thr Gly Asp Ile Thr
        50                  55                  60

Leu Gln Asn Leu Gly Asp Ser Ala Ala Leu Thr Lys Gly Cys Phe Ser
 65                  70                  75                  80

Asp Thr Thr Glu Ser Leu Ser Phe Ala Gly Lys Gly Tyr Ser Leu Ser
                85                  90                  95

Phe Leu Asn Ile Lys Ser Ser Ala Glu Gly Ala Ala Leu Ser Val Thr
            100                 105                 110

Thr Asp Lys Asn Leu Ser Leu Thr Gly Phe Ser Ser Leu Thr Phe Leu
        115                 120                 125

Ala Ala Pro Ser Ser Val Ile Thr Thr Pro Ser Gly Lys Gly Ala Val
130                 135                 140

Lys Cys Gly Gly Asp Leu Thr Phe Asp Asn Asn Gly Thr Ile Leu Phe
145                 150                 155                 160

Lys Gln Asp Tyr Cys Glu Glu Asn Gly Gly Ala Ile Ser Thr Lys Asn
                165                 170                 175

Leu Ser Leu Lys Asn Ser Thr Gly Ser Ile Ser Phe Glu Gly Asn Lys
            180                 185                 190

Ser Ser Ala Thr Gly Lys Lys Gly Ala Ile Cys Ala Thr Gly Thr
        195                 200                 205

Val Asp Ile Thr Asn Asn Thr Ala Pro Thr Leu Phe Ser Asn Asn Ile
    210                 215                 220

Ala Glu Ala Ala Gly Gly Ala Ile Asn Ser Thr Gly Asn Cys Thr Ile
225                 230                 235                 240

Thr Gly Asn Thr Ser Leu Val Phe Ser Glu Asn Ser Val Thr Ala Thr
                245                 250                 255

Ala Gly Asn Gly Gly Ala Leu Ser Gly Asp Ala Asp Val Thr Ile Ser
            260                 265                 270

Gly Asn Gln Ser Val Thr Phe Ser Gly Asn Gln Ala Val Ala Asn Gly
        275                 280                 285

Gly Ala Ile Tyr Ala Lys Lys Leu Thr Leu Ala Ser Gly Gly Gly Gly
    290                 295                 300

Gly Ile Ser Phe Ser Asn Asn Ile Val Gln Gly Thr Thr Ala Gly Asn
```

-continued

```
            305                 310                 315                 320
Gly Gly Ala Ile Ser Ile Leu Ala Ala Gly Glu Cys Ser Leu Ser Ala
                325                 330                 335

Glu Ala Gly Asp Ile Thr Phe Asn Gly Asn Ala Ile Val Ala Thr Thr
                340                 345                 350

Pro Gln Thr Thr Lys Arg Asn Ser Ile Asp Ile Gly Ser Thr Ala Lys
                355                 360                 365

Ile Thr Asn Leu Arg Ala Ile Ser Gly His Ser Ile Phe Phe Tyr Asp
            370                 375                 380

Pro Ile Thr Ala Asn Thr Ala Ala Asp Ser Thr Asp Thr Leu Asn Leu
385                 390                 395                 400

Asn Lys Ala Asp Ala Gly Asn Ser Thr Asp Tyr Ser Gly Ser Ile Val
                405                 410                 415

Phe Ser Gly Glu Lys Leu Ser Glu Asp Glu Ala Lys Val Ala Asp Asn
                420                 425                 430

Leu Thr Ser Thr Leu Lys Gln Pro Val Thr Leu Thr Ala Gly Asn Leu
            435                 440                 445

Val Leu Lys Arg Gly Val Thr Leu Asp Thr Lys Gly Phe Thr Gln Thr
        450                 455                 460

Ala Gly Ser Ser Val Ile Met Asp Ala Gly Thr Thr Leu Lys Ala Ser
465                 470                 475                 480

Thr Glu Glu Val Thr Leu Thr Gly Leu Ser Ile Pro Val Asp Ser Leu
                485                 490                 495

Gly Glu Gly Lys Lys Val Val Ile Ala Ala Ser Ala Ala Ser Lys Asn
                500                 505                 510

Val Ala Leu Ser Gly Pro Ile Leu Leu Leu Asp Asn Gln Gly Asn Ala
            515                 520                 525

Tyr Glu Asn His Asp Leu Gly Lys Thr Gln Asp Phe Ser Phe Val Gln
        530                 535                 540

Leu Ser Ala Leu Gly Thr Ala Thr Thr Thr Asp Val Pro Ala Val Pro
545                 550                 555                 560

Thr Val Ala Thr Pro Thr His Tyr Gly Tyr Gln Gly Thr Trp Gly Met
                565                 570                 575

Thr Trp Val Asp Asp Thr Ala Ser Thr Pro Lys Thr Lys Thr Ala Thr
            580                 585                 590

Leu Ala Trp Thr Asn Thr Gly Tyr Leu Pro Asn Pro Glu Arg Gln Gly
        595                 600                 605

Pro Leu Val Pro Asn Ser Leu Trp Gly Ser Phe Ser Asp Ile Gln Ala
        610                 615                 620

Ile Gln Gly Val Ile Glu Arg Ser Ala Leu Thr Leu Cys Ser Asp Arg
625                 630                 635                 640

Gly Phe Trp Ala Ala Gly Val Ala Asn Phe Leu Asp Lys Asp Lys Lys
                645                 650                 655

Gly Glu Lys Arg Lys Tyr Arg His Lys Ser Gly Gly Tyr Ala Ile Gly
                660                 665                 670

Gly Ala Ala Gln Thr Cys Ser Glu Asn Leu Ile Ser Phe Ala Phe Cys
            675                 680                 685

Gln Leu Phe Gly Ser Asp Lys Asp Phe Leu Val Ala Lys Asn His Thr
        690                 695                 700

Asp Thr Tyr Ala Gly Ala Phe Tyr Ile Gln His Ile Thr Glu Cys Ser
705                 710                 715                 720

Gly Phe Ile Gly Cys Leu Leu Asp Lys Leu Pro Gly Ser Trp Ser His
                725                 730                 735
```

```
Lys Pro Leu Val Leu Glu Gly Gln Leu Ala Tyr Ser His Val Ser Asn
                740                 745                 750

Asp Leu Lys Thr Lys Tyr Thr Ala Tyr Pro Glu Val Lys Gly Ser Trp
                755                 760                 765

Gly Asn Asn Ala Phe Asn Met Met Leu Gly Ala Ser Ser His Ser Tyr
                770                 775                 780

Pro Glu Tyr Leu His Cys Phe Asp Thr Tyr Ala Pro Tyr Ile Lys Leu
785                 790                 795                 800

Asn Leu Thr Tyr Ile Arg Gln Asp Ser Phe Ser Glu Lys Gly Thr Glu
                805                 810                 815

Gly Arg Ser Phe Asp Asp Ser Asn Leu Phe Asn Leu Ser Leu Pro Ile
                820                 825                 830

Gly Val Lys Phe Glu Lys Phe Ser Asp Cys Asn Asp Phe Ser Tyr Asp
                835                 840                 845

Leu Thr Leu Ser Tyr Val Pro Asp Leu Ile Arg Asn Asp Pro Lys Cys
850                 855                 860

Thr Thr Ala Leu Val Ile Ser Gly Ala Ser Trp Glu Thr Tyr Ala Asn
865                 870                 875                 880

Asn Leu Ala Arg Gln Ala Leu Gln Val Arg Ala Gly Ser His Tyr Ala
                885                 890                 895

Phe Ser Pro Met Phe Glu Val Leu Gly Gln Phe Val Phe Glu Val Arg
                900                 905                 910

Gly Ser (2) INFORMATION FOR SEQ ID NO: 27:

(i) SEQUENCE CHARACTERISTICS:
        (A) LENGTH: 1200 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 1...1200
        (D) OTHER INFORMATION:

(xi) SEQUENCE DESCRIPTION: SEQ ID NO: 27:

GAT CCT AAA AAT AAA GAG TAC ACA GGG ACC ATA CTC TTT TCT GGA GAA     48
Asp Pro Lys Asn Lys Glu Tyr Thr Gly Thr Ile Leu Phe Ser Gly Glu
1               5                   10                  15

AAG AGT CTA GCA AAC GAT CCT AGG GAT TTT AAA TCT ACA ATC CCT CAG     96
Lys Ser Leu Ala Asn Asp Pro Arg Asp Phe Lys Ser Thr Ile Pro Gln
                20                  25                  30

AAC GTC AAC CTG TCT GCA GGA TAC TTA GTT ATT AAA GAG GGG GCC GAA    144
Asn Val Asn Leu Ser Ala Gly Tyr Leu Val Ile Lys Glu Gly Ala Glu
            35                  40                  45

GTC ACA GTT TCA AAA TTC ACG CAG TCT CCA GGA TCG CAT TTA GTT TTA    192
Val Thr Val Ser Lys Phe Thr Gln Ser Pro Gly Ser His Leu Val Leu
        50                  55                  60

GAT TTA GGA ACC AAA CTG ATA GCC TCT AAG GAA GAC ATT GCC ATC ACA    240
Asp Leu Gly Thr Lys Leu Ile Ala Ser Lys Glu Asp Ile Ala Ile Thr
65              70                  75                  80

GGC CTC GCG ATA GAT ATA GAT AGC TTA AGC TCA TCC TCA ACA GCA GCT    288
Gly Leu Ala Ile Asp Ile Asp Ser Leu Ser Ser Ser Ser Thr Ala Ala
                85                  90                  95

GTT ATT AAA GCA AAC ACC GCA AAT AAA CAG ATA TCC GTG ACG GAC TCT    336
```

```
Val Ile Lys Ala Asn Thr Ala Asn Lys Gln Ile Ser Val Thr Asp Ser
            100                 105                 110

ATA GAA CTT ATC TCG CCT ACT GGC AAT GCC TAT GAA GAT CTC AGA ATG    384
Ile Glu Leu Ile Ser Pro Thr Gly Asn Ala Tyr Glu Asp Leu Arg Met
            115                 120                 125

AGA AAT TCA CAG ACG TTC CCT CTG CTC TCT TTA GAG CCT GGA GCC GGG    432
Arg Asn Ser Gln Thr Phe Pro Leu Leu Ser Leu Glu Pro Gly Ala Gly
130             135                 140

GGT AGT GTG ACT GTA ACT GCT GGA GAT TTC CTA CCG GTA AGT CCC CAT    480
Gly Ser Val Thr Val Thr Ala Gly Asp Phe Leu Pro Val Ser Pro His
145                 150                 155                 160

TAT GGT TTT CAA GGC AAT TGG AAA TTA GCT TGG ACA GGA ACT GGA AAC    528
Tyr Gly Phe Gln Gly Asn Trp Lys Leu Ala Trp Thr Gly Thr Gly Asn
                165                 170                 175

AAA GTT GGA GAA TTC TTC TGG GAT AAA ATA AAT TAT AAG CCT AGA CCT    576
Lys Val Gly Glu Phe Phe Trp Asp Lys Ile Asn Tyr Lys Pro Arg Pro
            180                 185                 190

GAA AAA GAA GGA AAT TTA GTT CCT AAT ATC TTG TGG GGG AAT GCT GTA    624
Glu Lys Glu Gly Asn Leu Val Pro Asn Ile Leu Trp Gly Asn Ala Val
        195                 200                 205

AAT GTC AGA TCC TTA ATG CAG GTT CAA GAG ACC CAT GCA TCG AGC TTA    672
Asn Val Arg Ser Leu Met Gln Val Gln Glu Thr His Ala Ser Ser Leu
210                 215                 220

CAG ACA GAT CGA GGG CTG TGG ATC GAT GGA ATT GGG AAT TTC TTC CAT    720
Gln Thr Asp Arg Gly Leu Trp Ile Asp Gly Ile Gly Asn Phe Phe His
225                 230                 235                 240

GTA TCT GCC TCC GAA GAC AAT ATA AGG TAC CGT CAT AAC AGC GGT GGA    768
Val Ser Ala Ser Glu Asp Asn Ile Arg Tyr Arg His Asn Ser Gly Gly
                245                 250                 255

TAT GTT CTA TCT GTA AAT AAT GAG ATC ACA CCT AAG CAC TAT ACT TCG    816
Tyr Val Leu Ser Val Asn Asn Glu Ile Thr Pro Lys His Tyr Thr Ser
            260                 265                 270

ATG GCA TTT TCC CAA CTC TTT AGT AGA GAC AAA GAC TAT GCG GTT TCC    864
Met Ala Phe Ser Gln Leu Phe Ser Arg Asp Lys Asp Tyr Ala Val Ser
        275                 280                 285

AAC AAC GAA TAC AGA ATG TAT TTA GGA TCG TAT CTC TAT CAA TAT ACA    912
Asn Asn Glu Tyr Arg Met Tyr Leu Gly Ser Tyr Leu Tyr Gln Tyr Thr
290                 295                 300

ACC TCC CTA GGG AAT ATT TTC CGT TAT GCT TCG CGT AAC CCT AAT GTA    960
Thr Ser Leu Gly Asn Ile Phe Arg Tyr Ala Ser Arg Asn Pro Asn Val
305                 310                 315                 320

AAC GTC GGG ATT CTC TCA AGA AGG TTT CTT CAA AAT CCT CTT ATG ATT    1008
Asn Val Gly Ile Leu Ser Arg Arg Phe Leu Gln Asn Pro Leu Met Ile
                325                 330                 335

TTT CAT TTT TTG TGT GCT TAT GGT CAT GCC ACC AAT GAT ATG AAA ACA    1056
Phe His Phe Leu Cys Ala Tyr Gly His Ala Thr Asn Asp Met Lys Thr
            340                 345                 350

GAC TAC GCA AAT TTC CCT ATG GTG AAA AAC AGC TGG AGA AAC AAT TGT    1104
Asp Tyr Ala Asn Phe Pro Met Val Lys Asn Ser Trp Arg Asn Asn Cys
        355                 360                 365

TGG GCT ATA AAA TGC GGA GGG AGC ATG CCT CTA TTG GTA TTT GAA AAC    1152
Trp Ala Ile Lys Cys Gly Gly Ser Met Pro Leu Leu Val Phe Glu Asn
370                 375                 380

GGA AAA CTT TTC CAA GGT GCC ATC CCA TTT ATG AAA CTA CAA TTA GTT    1200
Gly Lys Leu Phe Gln Gly Ala Ile Pro Phe Met Lys Leu Gln Leu Val
385                 390                 395                 400
```

(2) INFORMATION FOR SEQ ID NO: 28:

(i) SEQUENCE CHARACTERISTICS:

(A) LENGTH: 400 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO: 28:

Asp Pro Lys Asn Lys Glu Tyr Thr Gly Thr Ile Leu Phe Ser Gly Glu
 1               5                  10                  15

Lys Ser Leu Ala Asn Asp Pro Arg Asp Phe Lys Ser Thr Ile Pro Gln
            20                  25                  30

Asn Val Asn Leu Ser Ala Gly Tyr Leu Val Ile Lys Glu Gly Ala Glu
        35                  40                  45

Val Thr Val Ser Lys Phe Thr Gln Ser Pro Gly Ser His Leu Val Leu
    50                  55                  60

Asp Leu Gly Thr Lys Leu Ile Ala Ser Lys Glu Asp Ile Ala Ile Thr
65                  70                  75                  80

Gly Leu Ala Ile Asp Ile Asp Ser Leu Ser Ser Ser Thr Ala Ala
                85                  90                  95

Val Ile Lys Ala Asn Thr Ala Asn Lys Gln Ile Ser Val Thr Asp Ser
                100                 105                 110

Ile Glu Leu Ile Ser Pro Thr Gly Asn Ala Tyr Glu Asp Leu Arg Met
            115                 120                 125

Arg Asn Ser Gln Thr Phe Pro Leu Leu Ser Leu Glu Pro Gly Ala Gly
130                 135                 140

Gly Ser Val Thr Val Thr Ala Gly Asp Phe Leu Pro Val Ser Pro His
145                 150                 155                 160

Tyr Gly Phe Gln Gly Asn Trp Lys Leu Ala Trp Thr Gly Thr Gly Asn
                165                 170                 175

Lys Val Gly Glu Phe Phe Trp Asp Lys Ile Asn Tyr Lys Pro Arg Pro
            180                 185                 190

Glu Lys Glu Gly Asn Leu Val Pro Asn Ile Leu Trp Gly Asn Ala Val
        195                 200                 205

Asn Val Arg Ser Leu Met Gln Val Gln Glu Thr His Ala Ser Ser Leu
    210                 215                 220

Gln Thr Asp Arg Gly Leu Trp Ile Asp Gly Ile Gly Asn Phe Phe His
225                 230                 235                 240

Val Ser Ala Ser Glu Asp Asn Ile Arg Tyr Arg His Asn Ser Gly Gly
                245                 250                 255

Tyr Val Leu Ser Val Asn Asn Glu Ile Thr Pro Lys His Tyr Thr Ser
            260                 265                 270

Met Ala Phe Ser Gln Leu Phe Ser Arg Asp Lys Asp Tyr Ala Val Ser
        275                 280                 285

Asn Asn Glu Tyr Arg Met Tyr Leu Gly Ser Tyr Leu Tyr Gln Tyr Thr
    290                 295                 300

Thr Ser Leu Gly Asn Ile Phe Arg Tyr Ala Ser Arg Asn Pro Asn Val
305                 310                 315                 320

Asn Val Gly Ile Leu Ser Arg Arg Phe Leu Gln Asn Pro Leu Met Ile
                325                 330                 335

Phe His Phe Leu Cys Ala Tyr Gly His Ala Thr Asn Asp Met Lys Thr
            340                 345                 350

Asp Tyr Ala Asn Phe Pro Met Val Lys Asn Ser Trp Arg Asn Asn Cys
        355                 360                 365

```
Trp Ala Ile Lys Cys Gly Gly Ser Met Pro Leu Leu Val Phe Glu Asn
    370             375             380

Gly Lys Leu Phe Gln Gly Ala Ile Pro Phe Met Lys Leu Gln Leu Val
385             390             395                 400
```

(2) INFORMATION FOR SEQ ID NO: 29:

(i) SEQUENCE CHARACTERISTICS:
        (A) LENGTH: 1830 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 1...1830
        (D) OTHER INFORMATION:

(xi) SEQUENCE DESCRIPTION: SEQ ID NO: 29:

```
GAT CTC ACA TTA GGG AGT CGT GAC AGT TAT AAT GGT GAT ACA AGC ACC        48
Asp Leu Thr Leu Gly Ser Arg Asp Ser Tyr Asn Gly Asp Thr Ser Thr
 1               5                  10                  15

ACA GAA TTT ACT CCT AAA GCG GCA ACT TCT GAT GCT AGT GGC ACG ACC        96
Thr Glu Phe Thr Pro Lys Ala Ala Thr Ser Asp Ala Ser Gly Thr Thr
            20                  25                  30

TAT ATT CTC GAT GGG GAT GTC TCG ATA AGC CAA GCA GGG AAA CAA ACG       144
Tyr Ile Leu Asp Gly Asp Val Ser Ile Ser Gln Ala Gly Lys Gln Thr
        35                  40                  45

AGC TTA ACC ACA AGT TGT TTT TCT AAC ACT GCA GGA AAT CTT ACC TTC       192
Ser Leu Thr Thr Ser Cys Phe Ser Asn Thr Ala Gly Asn Leu Thr Phe
 50                  55                  60

TTA GGG AAC GGA TTT TCT CTT CAT TTT GAC AAT ATT ATT TCG TCT ACT       240
Leu Gly Asn Gly Phe Ser Leu His Phe Asp Asn Ile Ile Ser Ser Thr
 65                  70                  75                  80

GTT GCA GGT GTT GTT GTT AGC AAT ACA GCA GCT TCT GGG ATT ACG AAA       288
Val Ala Gly Val Val Val Ser Asn Thr Ala Ala Ser Gly Ile Thr Lys
                 85                  90                  95

TTC TCA GGA TTT TCA ACT CTT CGG ATG CTT GCA GCT CCT AGG ACC ACA       336
Phe Ser Gly Phe Ser Thr Leu Arg Met Leu Ala Ala Pro Arg Thr Thr
            100                 105                 110

GGT AAA GGA GCC ATT AAA ATT ACC GAT GGT CTG GTG TTT GAG AGT ATA       384
Gly Lys Gly Ala Ile Lys Ile Thr Asp Gly Leu Val Phe Glu Ser Ile
        115                 120                 125

GGG AAT CTT GAT CCG ATT ACT GTA ACA GGA TCG ACA TCT GTT GCT GAT       432
Gly Asn Leu Asp Pro Ile Thr Val Thr Gly Ser Thr Ser Val Ala Asp
130                 135                 140

GCT CTC AAT ATT AAT AGC CCT GAT ACT GGA GAT AAC AAA GAG TAT ACG       480
Ala Leu Asn Ile Asn Ser Pro Asp Thr Gly Asp Asn Lys Glu Tyr Thr
145                 150                 155                 160

GGA ACC ATA GTC TTT TCT GGA GAG AAG CTC ACG GAG GCA GAA GCT AAA       528
Gly Thr Ile Val Phe Ser Gly Glu Lys Leu Thr Glu Ala Glu Ala Lys
                165                 170                 175

GAT GAG AAG AAC CGC ACT TCT AAA TTA CTT CAA AAT GTT GCT TTT AAA       576
Asp Glu Lys Asn Arg Thr Ser Lys Leu Leu Gln Asn Val Ala Phe Lys
            180                 185                 190

AAT GGG ACT GTA GTT TTA AAA GGT GAT GTC GTT TTA AGT GCG AAC GGT       624
Asn Gly Thr Val Val Leu Lys Gly Asp Val Val Leu Ser Ala Asn Gly
        195                 200                 205

TTC TCT CAG GAT GCA AAC TCT AAG TTG ATT ATG GAT TTA GGG ACG TCG       672
Phe Ser Gln Asp Ala Asn Ser Lys Leu Ile Met Asp Leu Gly Thr Ser
```

```
              210                 215                 220
TTG GTT GCA AAC ACC GAA AGT ATC GAG TTA ACG AAT TTG GAA ATT AAT         720
Leu Val Ala Asn Thr Glu Ser Ile Glu Leu Thr Asn Leu Glu Ile Asn
225                 230                 235                 240

ATA GAC TCT CTC AGG AAC GGG AAA AAG ATA AAA CTC AGT GCT GCC ACA         768
Ile Asp Ser Leu Arg Asn Gly Lys Lys Ile Lys Leu Ser Ala Ala Thr
                245                 250                 255

GCT CAG AAA GAT ATT CGT ATA GAT CGT CCT GTT GTA CTG GCA ATT AGC         816
Ala Gln Lys Asp Ile Arg Ile Asp Arg Pro Val Val Leu Ala Ile Ser
                260                 265                 270

GAT GAG AGT TTT TAT CAA AAT GGC TTT TTG AAT GAG GAC CAT TCC TAT         864
Asp Glu Ser Phe Tyr Gln Asn Gly Phe Leu Asn Glu Asp His Ser Tyr
                275                 280                 285

GAT GGG ATT CTT GAG TTA GAT GCT GGG AAA GAC ATC GTG ATT TCT GCA         912
Asp Gly Ile Leu Glu Leu Asp Ala Gly Lys Asp Ile Val Ile Ser Ala
                290                 295                 300

GAT TCT CGC AGT ATA GAT GCT GTA CAA TCT CCG TAT GGC TAT CAG GGA         960
Asp Ser Arg Ser Ile Asp Ala Val Gln Ser Pro Tyr Gly Tyr Gln Gly
305                 310                 315                 320

AAG TGG ACG ATC AAT TGG TCT ACT GAT GAT AAG AAA GCT ACG GTT TCT        1008
Lys Trp Thr Ile Asn Trp Ser Thr Asp Asp Lys Lys Ala Thr Val Ser
                325                 330                 335

TGG GCG AAG CAG AGT TTT AAT CCC ACT GCT GAG CAG GAG GCT CCG TTA        1056
Trp Ala Lys Gln Ser Phe Asn Pro Thr Ala Glu Gln Glu Ala Pro Leu
                340                 345                 350

GTT CCT AAT CTT CTT TGG GGT TCT TTT ATA GAT GTT CGT TCC TTC CAG        1104
Val Pro Asn Leu Leu Trp Gly Ser Phe Ile Asp Val Arg Ser Phe Gln
                355                 360                 365

AAT TTT ATA GAG CTA GGT ACT GAA GGT GCT CCT TAC GAA AAG AGA TTT        1152
Asn Phe Ile Glu Leu Gly Thr Glu Gly Ala Pro Tyr Glu Lys Arg Phe
370                 375                 380

TGG GTT GCA GGC ATT TCC AAT GTT TTG CAT AGG AGC GGT CGT GAA AAT        1200
Trp Val Ala Gly Ile Ser Asn Val Leu His Arg Ser Gly Arg Glu Asn
385                 390                 395                 400

CAA AGG AAA TTC CGT CAT GTG AGT GGA GGT GCT GTA GTA GGT GCT AGC        1248
Gln Arg Lys Phe Arg His Val Ser Gly Gly Ala Val Val Gly Ala Ser
                405                 410                 415

ACG AGG ATG CCG GGT GGT GAT ACC TTG TCT CTG GGT TTT GCT CAG CTC        1296
Thr Arg Met Pro Gly Gly Asp Thr Leu Ser Leu Gly Phe Ala Gln Leu
                420                 425                 430

TTT GCG CGT GAC AAA GAC TAC TTT ATG AAT ACC AAT TTC GCA AAG ACC        1344
Phe Ala Arg Asp Lys Asp Tyr Phe Met Asn Thr Asn Phe Ala Lys Thr
                435                 440                 445

TAC GCA GGA TCT TTA CGT TTG CAG CAC GAT GCT TCC CTA TAC TCT GTG        1392
Tyr Ala Gly Ser Leu Arg Leu Gln His Asp Ala Ser Leu Tyr Ser Val
450                 455                 460

GTG AGT ATC CTT TTA GGA GAG GGA GGA CTC CGC GAG ATC CTG TTG CCT        1440
Val Ser Ile Leu Leu Gly Glu Gly Gly Leu Arg Glu Ile Leu Leu Pro
465                 470                 475                 480

TAT GTT TCC AAT ACT CTG CCG TGC TCT TTC TAT GGG CAG CTT AGC TAC        1488
Tyr Val Ser Asn Thr Leu Pro Cys Ser Phe Tyr Gly Gln Leu Ser Tyr
                485                 490                 495

GGC CAT ACG GAT CAT CGC ATG AAG ACC GAG TCT CTA CCC CCC CCC CCC        1536
Gly His Thr Asp His Arg Met Lys Thr Glu Ser Leu Pro Pro Pro Pro
                500                 505                 510

CCG ACG CTC TCG ACG GAT CAT ACT TCT TGG GGA GGA TAT GTC TGG GCT        1584
Pro Thr Leu Ser Thr Asp His Thr Ser Trp Gly Gly Tyr Val Trp Ala
                515                 520                 525

GGA GAG CTG GGA ACT CGA GTT GCT GTT GAA AAT ACC AGC GGC AGA GGA        1632
Gly Glu Leu Gly Thr Arg Val Ala Val Glu Asn Thr Ser Gly Arg Gly
```

-continued

```
Gly Glu Leu Gly Thr Arg Val Ala Val Glu Asn Thr Ser Gly Arg Gly
        530                 535                 540

TTT TTC CGA GAG TAC ACT CCA TTT GTA AAA GTC CAA GCT GTT TAC TCG       1680
Phe Phe Arg Glu Tyr Thr Pro Phe Val Lys Val Gln Ala Val Tyr Ser
545                 550                 555                 560

CGC CAA GAT AGC TTT GTT GAA CTA GGA GCT ATC AGT CGT GAT TTT AGT       1728
Arg Gln Asp Ser Phe Val Glu Leu Gly Ala Ile Ser Arg Asp Phe Ser
                565                 570                 575

GAT TCG CAT CTT TAT AAC CTT GCG ATT CCT CTT GGA ATC AAG TTA GAG       1776
Asp Ser His Leu Tyr Asn Leu Ala Ile Pro Leu Gly Ile Lys Leu Glu
            580                 585                 590

AAA CGG TTT GCA GAG CAA TAT TAT CAT GTT GTT GCG ATG TAT TCT CCA       1824
Lys Arg Phe Ala Glu Gln Tyr Tyr His Val Val Ala Met Tyr Ser Pro
        595                 600                 605

GAT GTT                                                                1830
Asp Val
610
```

(2) INFORMATION FOR SEQ ID NO: 30:

(i) SEQUENCE CHARACTERISTICS:
        (A) LENGTH: 610 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO: 30:

```
Asp Leu Thr Leu Gly Ser Arg Asp Ser Tyr Asn Gly Asp Thr Ser Thr
1               5                   10                  15

Thr Glu Phe Thr Pro Lys Ala Ala Thr Ser Asp Ala Ser Gly Thr Thr
                20                  25                  30

Tyr Ile Leu Asp Gly Asp Val Ser Ile Ser Gln Ala Gly Lys Gln Thr
            35                  40                  45

Ser Leu Thr Thr Ser Cys Phe Ser Asn Thr Ala Gly Asn Leu Thr Phe
    50                  55                  60

Leu Gly Asn Gly Phe Ser Leu His Phe Asp Asn Ile Ile Ser Ser Thr
65                  70                  75                  80

Val Ala Gly Val Val Val Ser Asn Thr Ala Ala Ser Gly Ile Thr Lys
                85                  90                  95

Phe Ser Gly Phe Ser Thr Leu Arg Met Leu Ala Ala Pro Arg Thr Thr
            100                 105                 110

Gly Lys Gly Ala Ile Lys Ile Thr Asp Gly Leu Val Phe Glu Ser Ile
        115                 120                 125

Gly Asn Leu Asp Pro Ile Thr Val Thr Gly Ser Thr Ser Val Ala Asp
    130                 135                 140

Ala Leu Asn Ile Asn Ser Pro Asp Thr Gly Asp Asn Lys Glu Tyr Thr
145                 150                 155                 160

Gly Thr Ile Val Phe Ser Gly Glu Lys Leu Thr Glu Ala Glu Ala Lys
                165                 170                 175

Asp Glu Lys Asn Arg Thr Ser Lys Leu Leu Gln Asn Val Ala Phe Lys
            180                 185                 190

Asn Gly Thr Val Val Leu Lys Gly Asp Val Val Leu Ser Ala Asn Gly
        195                 200                 205

Phe Ser Gln Asp Ala Asn Ser Lys Leu Ile Met Asp Leu Gly Thr Ser
    210                 215                 220
```

```
Leu Val Ala Asn Thr Glu Ser Ile Glu Leu Thr Asn Leu Glu Ile Asn
225                 230                 235                 240

Ile Asp Ser Leu Arg Asn Gly Lys Lys Ile Lys Leu Ser Ala Ala Thr
                245                 250                 255

Ala Gln Lys Asp Ile Arg Ile Asp Arg Pro Val Val Leu Ala Ile Ser
                260                 265                 270

Asp Glu Ser Phe Tyr Gln Asn Gly Phe Leu Asn Glu Asp His Ser Tyr
                275                 280                 285

Asp Gly Ile Leu Glu Leu Asp Ala Gly Lys Asp Ile Val Ile Ser Ala
                290                 295                 300

Asp Ser Arg Ser Ile Asp Ala Val Gln Ser Pro Tyr Gly Tyr Gln Gly
305                 310                 315                 320

Lys Trp Thr Ile Asn Trp Ser Thr Asp Asp Lys Lys Ala Thr Val Ser
                325                 330                 335

Trp Ala Lys Gln Ser Phe Asn Pro Thr Ala Glu Gln Glu Ala Pro Leu
                340                 345                 350

Val Pro Asn Leu Leu Trp Gly Ser Phe Ile Asp Val Arg Ser Phe Gln
                355                 360                 365

Asn Phe Ile Glu Leu Gly Thr Glu Gly Ala Pro Tyr Glu Lys Arg Phe
                370                 375                 380

Trp Val Ala Gly Ile Ser Asn Val Leu His Arg Ser Gly Arg Glu Asn
385                 390                 395                 400

Gln Arg Lys Phe Arg His Val Ser Gly Gly Ala Val Val Gly Ala Ser
                405                 410                 415

Thr Arg Met Pro Gly Gly Asp Thr Leu Ser Leu Gly Phe Ala Gln Leu
                420                 425                 430

Phe Ala Arg Asp Lys Asp Tyr Phe Met Asn Thr Asn Phe Ala Lys Thr
                435                 440                 445

Tyr Ala Gly Ser Leu Arg Leu Gln His Asp Ala Ser Leu Tyr Ser Val
                450                 455                 460

Val Ser Ile Leu Leu Gly Glu Gly Gly Leu Arg Glu Ile Leu Leu Pro
465                 470                 475                 480

Tyr Val Ser Asn Thr Leu Pro Cys Ser Phe Tyr Gly Gln Leu Ser Tyr
                485                 490                 495

Gly His Thr Asp His Arg Met Lys Thr Glu Ser Leu Pro Pro Pro Pro
                500                 505                 510

Pro Thr Leu Ser Thr Asp His Thr Ser Trp Gly Gly Tyr Val Trp Ala
                515                 520                 525

Gly Glu Leu Gly Thr Arg Val Ala Val Glu Asn Thr Ser Gly Arg Gly
                530                 535                 540

Phe Phe Arg Glu Tyr Thr Pro Phe Val Lys Val Gln Ala Val Tyr Ser
545                 550                 555                 560

Arg Gln Asp Ser Phe Val Glu Leu Gly Ala Ile Ser Arg Asp Phe Ser
                565                 570                 575

Asp Ser His Leu Tyr Asn Leu Ala Ile Pro Leu Gly Ile Lys Leu Glu
                580                 585                 590

Lys Arg Phe Ala Glu Gln Tyr Tyr His Val Val Ala Met Tyr Ser Pro
                595                 600                 605

Asp Val
610
```